(12) United States Patent
Lindsey et al.

(10) Patent No.: US 8,207,329 B2
(45) Date of Patent: Jun. 26, 2012

(54) SYNTHESIS OF CHLORINS AND PHORBINES WITH ENHANCED RED SPECTRAL FEATURES

(75) Inventors: Jonathan S. Lindsey, Raleigh, NC (US); Joydev K. Laha, Charlestown, MA (US); Muthiah Chinnasamy, Greensboro, NC (US); K. Eszter Borbas, Stockholm (SE)

(73) Assignee: North Carolina State University, Raleigh, NC (US)

( * ) Notice: Subject to any disclaimer, the term of this patent is extended or adjusted under 35 U.S.C. 154(b) by 757 days.

(21) Appl. No.: 12/095,435

(22) PCT Filed: Nov. 30, 2006

(86) PCT No.: PCT/US2006/045928
§ 371 (c)(1),
(2), (4) Date: Jan. 30, 2009

(87) PCT Pub. No.: WO2007/064842
PCT Pub. Date: Jun. 7, 2007

(65) Prior Publication Data
US 2009/0227553 A1    Sep. 10, 2009

Related U.S. Application Data

(60) Provisional application No. 60/740,924, filed on Nov. 30, 2005.

(51) Int. Cl.
*C07D 487/00* (2006.01)
*C07B 47/00* (2006.01)

(52) U.S. Cl. ...................................... 540/145
(58) Field of Classification Search ............ 540/145
See application file for complete search history.

(56) References Cited

U.S. PATENT DOCUMENTS

| | | | |
|---|---|---|---|
| 5,173,504 A * | 12/1992 | Dougherty .................. | 514/410 |
| 6,212,093 B1 | 4/2001 | Lindsey | |
| 6,272,038 B1 | 8/2001 | Clausen et al. | |
| 6,559,374 B2 * | 5/2003 | Lindsey et al. ............... | 136/263 |
| 6,596,935 B2 | 7/2003 | Lindsey et al. | |
| 6,777,402 B2 | 8/2004 | Nifantiev et al. | |
| 6,867,310 B1 * | 3/2005 | Buchwald et al. ............ | 549/453 |
| 6,916,982 B2 | 7/2005 | Loewe et al. | |
| 2004/0044197 A1 | 3/2004 | Pandey et al. | |
| 2004/0110731 A1 | 6/2004 | Chan et al. | |
| 2004/0202612 A1 | 10/2004 | Adair | |
| 2005/0137180 A1 | 6/2005 | Robinson et al. | |
| 2005/0277770 A1 | 12/2005 | Balakumar et al. | |
| 2007/0108438 A1 | 5/2007 | Lindsey et al. | |

FOREIGN PATENT DOCUMENTS

| | | |
|---|---|---|
| WO | WO 2007047925 A2 | 4/2007 |
| WO | WO 2007064841 A2 | 6/2007 |

OTHER PUBLICATIONS

Eisner et al, (Jnal of the Chem Society (1964).*
Caughy et al., J'nal of Org. Chem (1966).*
Lemberg et al., (Biochemical J'nal (951), 49, 674-83.*
Bamfield et al., (J'nal Chem. Soc. C. Org. (1966), (6), 1436-1443.*
International Search Report and Written Opinion, PCT/US06/45928, Oct. 17, 2007.
Kim HJ. De novo synthesis of stable bacteriochlorins, North Carolina State University—Thesis, Ph.D. [online]. Mar. 2005 [retrieved on May 29, 2008], pp. 1-149 www.lib.ncsu.edu/theses/available/etd-03242005-180313/unrestricted/etd.pdf.
Borbas K E et al. Bioconjugatable porphyrins bearing a compact swallowtail motif for water solubility (2006), vol. 17, pp. 638-653.
Borbas K E et al. A compact water-soluble porphyrin bearing an iodoacetamido bioconjugatable site. Organic & Biomolecular Chemistry (2008), vol. 6, pp. 187-194.

\* cited by examiner

*Primary Examiner* — Paul V. Ward
(74) *Attorney, Agent, or Firm* — Myers Bigel Sibley & Sajovec, P.A.

(57) ABSTRACT

The present invention provides compounds of the general Formula DI: along with methods of making such compounds, formulations containing the same, and methods of using the same (e.g., in photodynamic therapy, for the production of solar cells, etc.).

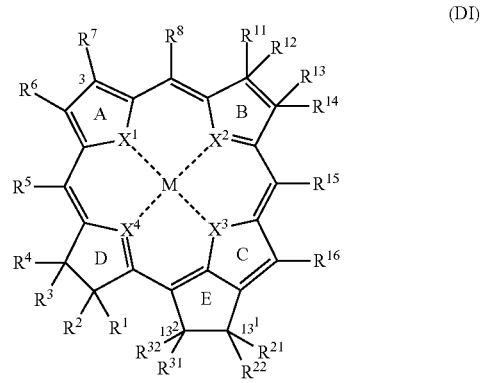

(DI)

6 Claims, 3 Drawing Sheets

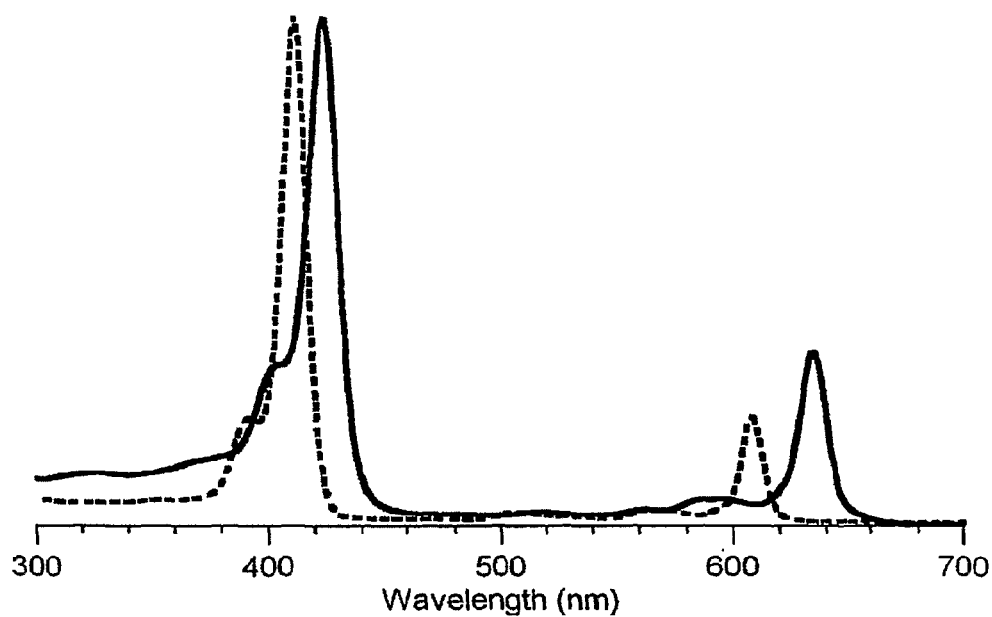
Figure 1. Absorption spectra of 13-acetylchlorin Zn-8 vs. the chlorin lacking the 13-acetyl group Zn-11.
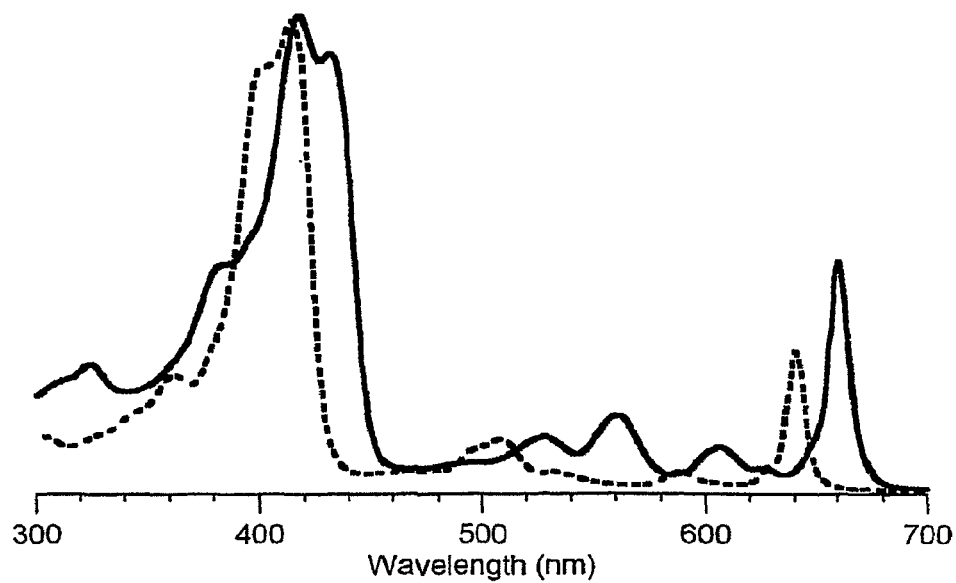
Figure 2. Absorption spectra of oxophorbine 10 vs. the chlorin lacking the $13^1$-oxo group 11.

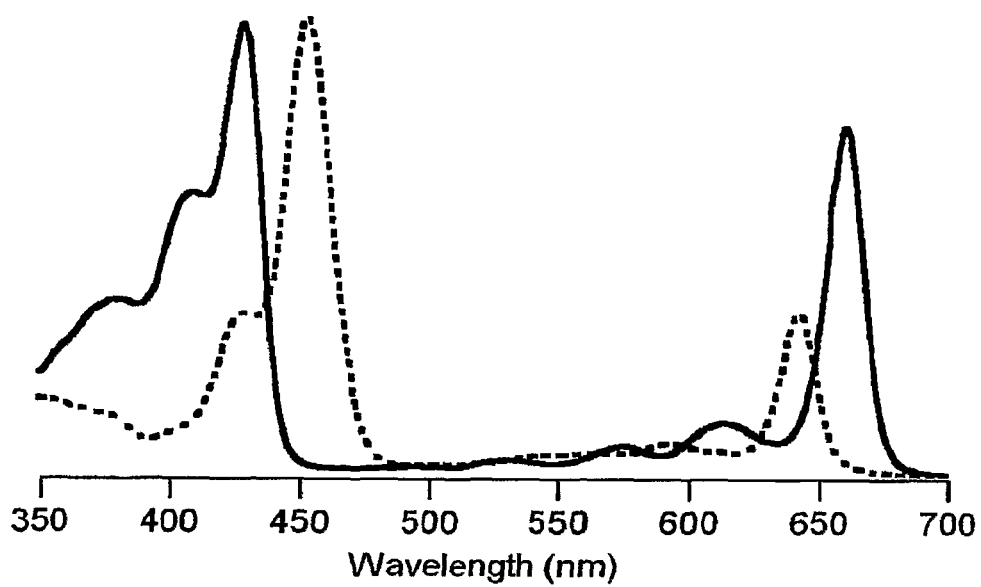
Figure 3. Absorption spectra of chlorophylls a and b.
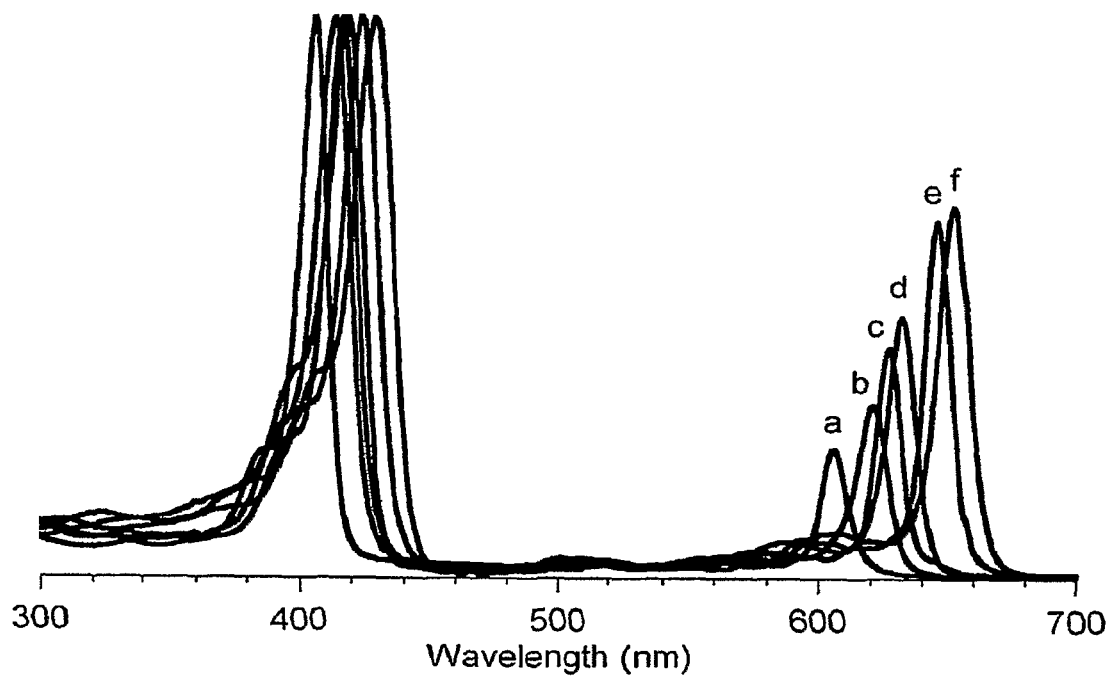
Figure 4. Absorption spectra in toluene at room temperature of a selection of zinc chlorins (10-mesityl family) bearing substituents at the 3- and/or 13-positions.

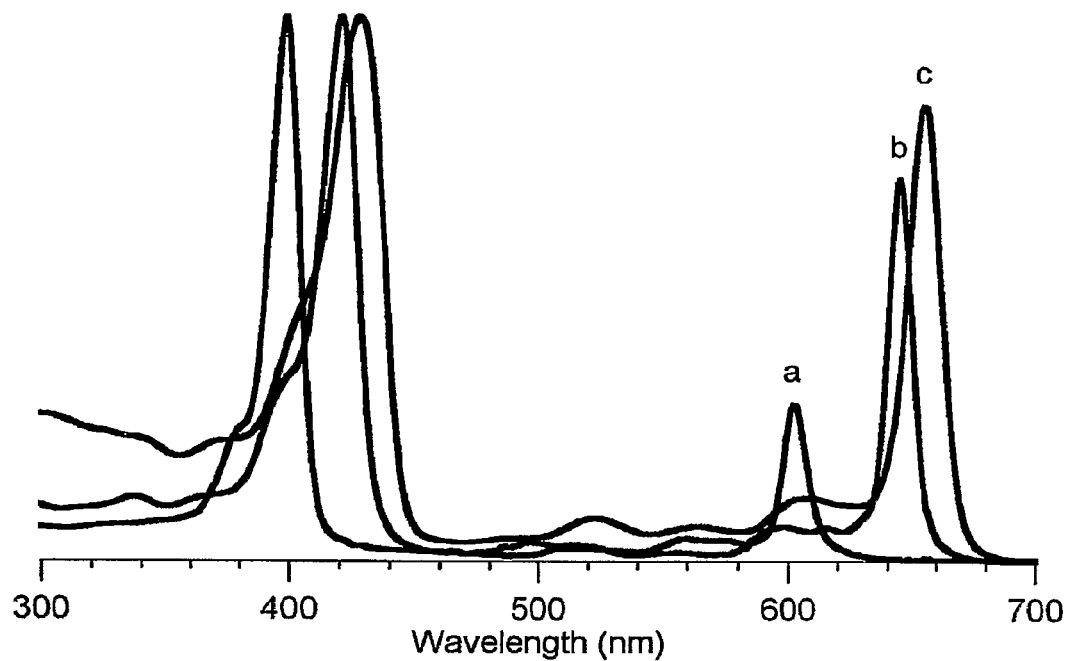
Figure 5. Absorption spectra in toluene at room temperature of zinc chlorins (10-unsubstituted family) bearing substituents at the 3,13-positions.

SYNTHESIS OF CHLORINS AND PHORBINES WITH ENHANCED RED SPECTRAL FEATURES

RELATED APPLICATIONS

This application is a national phase application of PCT Application PCT/US2006/045928, filed Nov. 30, 2006, and published in English on Jun. 7, 2007, as International Publication No. WO 2007/064842, and which claims the benefit of U.S. Provisional Patent Application Ser. No. 60/740,924, filed Nov. 30, 2005, the disclosure of each of which is incorporated by reference herein in its entirety.

This application is related to:

H. J. Kim and J. S. Lindsey, De Novo Synthesis of Bacteriochlorins, U.S. Provisional Patent Application No. 60/654,270; Filed Feb. 18, 2005; and H.-J. Kim and J. S. Lindsey, De Novo Synthesis of Bacteriochlorins, U.S. Provisional Patent Application No. 60/720,175, filed Sep. 23, 2005;

J. Lindsey, M. Taniguchi, A. Balakumar, and D. Fan, Methods and Intermediates for the Synthesis of Porphyrins, U.S. patent application Ser. No. 11/193,562, filed Jul. 29, 2005;

K. E. Borbas and J. S. Lindsey, Swallowtail motifs for imparting water solubility to porphyrinic compounds, U.S. Provisional Patent Application Ser. No. 60/728,558, Filed Oct. 20, 2005; and J. Lindsey, Porphyrinic compounds for use in flow cytometry, filed concurrently herewith.

GOVERNMENT FUNDING

This invention was made with Government support under Grant No. GM36238 from the National Institutes of Health. The US Government has certain rights to this invention.

FIELD OF THE INVENTION

The present invention concerns porphyrinic compounds having fused "E" rings, along with methods and intermediates for making the same.

BACKGROUND OF THE INVENTION

The fundamental chromophore of the chlorophylls is a chlorin, which differs from a porphyrin in having one pyrrole ring reduced at the β-positions (Chart 1).

Chart 1

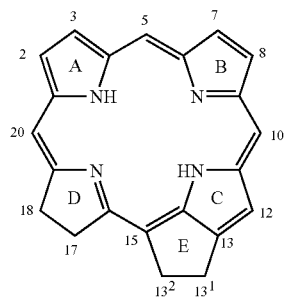

In addition, chlorophylls contain an annulated cyclopentyl ring bearing a $13^1$-oxo group (known as the isocyclic ring) at the periphery of the macrocycle (Scheer, H. In *Chlorophylls*; Scheer, H. Ed.; CRC Press, Inc.: Boca Raton, Fla., USA, 1991; pp 3-30). Chlorophyll a exhibits a strong B band at 430 nm and a strong $Q_y$ band at 662 nm (FIG. 3).

The $13^1$-oxo group, which is conjugated with the π-electron of the macrocycle, causes a significant redshift of the long wavelength absorption band ($Q_y$ band) and increases the intensity of the $Q_y$ band compared to synthetic chlorins lacking a $13^1$-oxo substituent. That the hyperchromic and bathochromic effects stem from the keto group and not the annulated cyclopentanyl ring alone has been proved by direct comparison of chlorophyll analogues (Chart 2). Indeed, a nickel pyropheophorbide (NiMPPh) absorbs at 638 nm ($\epsilon$~50,000 $M^{-1}$ $cm^{-1}$) whereas the deoxo analogue (NiDMPPh) absorbs at 608 nm ($\epsilon$~25,000 $M^{-1}cm^{-1}$) (Boldt, N. J et al., *J. Am. Chem. Soc.* 1987, 109, 2284-2298).

Chart 2

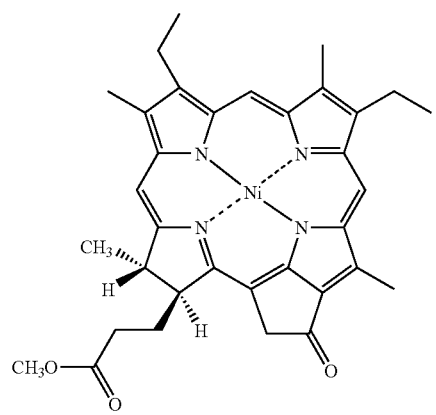

NiMPPh

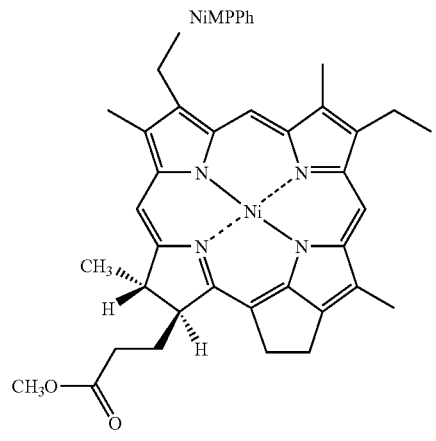

NiDMPPh

The design and synthesis of molecules with intense absorption in the red or near-IR regions enables a variety of applications encompassing solar cells (Linke-Schaetzel, M. et al., *Thin Solid Films* 2004, 451, 16-21), medical imaging (Licha, K. *Top. Curr. Chem.* 2002, 222, 1-29) and photodynamic therapy (Pandey, R. K.; Zheng, G. In *The Porphyrin Handbook*; Kadish, K. M.; Smith, K. M.; Guilard, R., Eds.; Academic Press: San Diego, 2000; Vol. 6, pp. 157-230). The ability to install the isocyclic ring in hydroporphyrins (chlorins and bacteriochlorins) is of considerable interest, given the beneficial spectral effects of the conjugated keto group. In addition, the keto group is expected to shift the oxidation potential to more positive values, thereby stabilizing the macrocycle to oxidation. However, only a few routes are known for the construction of the isocyclic ring (Scheme 1).
Scheme 1 (Part 1 of 2)
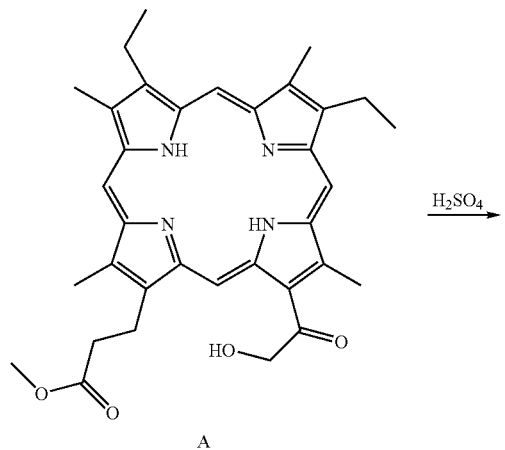
A
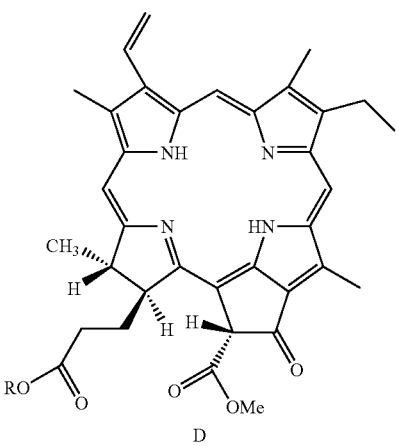
D
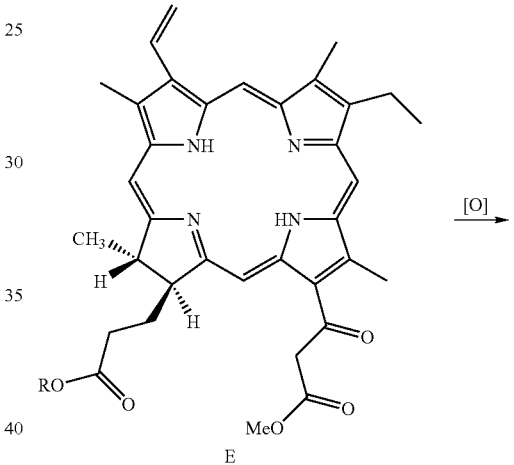
B
Scheme 1 (Part 2 of 2)
E
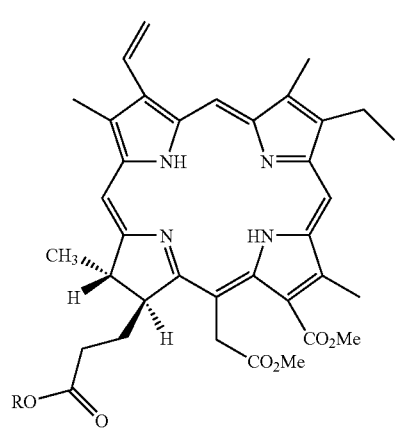
C
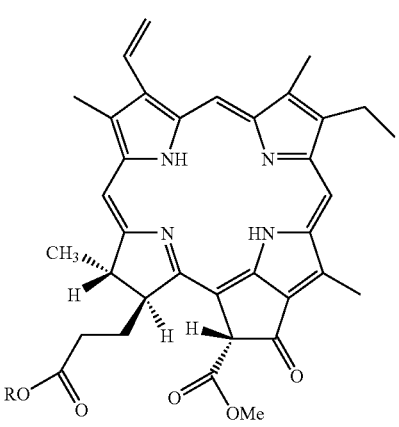
F

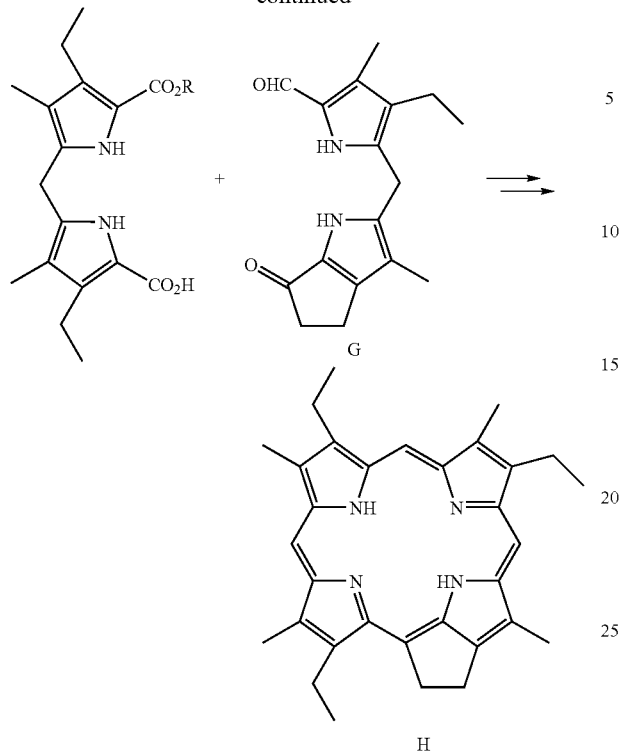

G

H

A review of synthetic manipulations of chlorophyll compounds is available (Pavlov, V. Y.; Ponomarev, G. V. *Chemistry of Heterocyclic Compounds* 2004, 40, 393-425). Fischer reported the dehydration of a (hydroxymethylcarbonyl)porphyrin using conc. $H_2SO_4$ to give the "pheoporphyrin" bearing the isocyclic ring (A→B)(Fischer, H.; Laubereau, O. *Justus Liebigs Ann. Chem.* 1938, 535, 17-37), and Dieckmann cyclization to convert chlorin $e_6$ trimethyl ester to methyl pheophorbide a (C→D) (Fischer, H.; Oestreicher, A. *Justus Liebigs Ann. Chem.* 1941, 546, 49-59). The Dieckmann cyclization initially was carried out using KOH/pyridine or sodium methoxide in methanol/acetone, but since then has been performed with milder bases such as potassium tert-butoxide/pyridine (Smith, K. M. et al., *Bioorg. Chem.* 1980, 9, 1-26; Smith, K. M. et al., *J. Am. Chem. Soc.* 1980, 102, 2437-2448; *J. Org. Chem.* 1980, 45, 2218-2224), sodium bis(trimethylsilylamide)(Gerlach, B.; Brantley, S.; Smith, K. M. *J. Org. Chem.* 1998, 63, 2314-2320), or potassium tert-butoxide/collidine (Pallenberg, A. J.; Dobhal, M. P.; Pandey, R. K. *Org. Process Res. Dev.* 2004, 8, 287-290). Kenner employed the oxidative cyclization of a β-ketoester at the 13-position of a porphyrin to give the pheoporphyrin (Cox, M. T. et al., *J. Am. Chem. Soc.* 1969, 91, 1232-1233; Kenner, G. W. et al., *J. Chem. Soc. Chem. Comm.* 1972, 844-845; Cox, M. T. et al., *J. Chem. Soc. Perkin Trans. I* 1974, 512-516; Kenner, G. W. et al., *J. Chem. Soc. Perkin Trans. I* 1974, 527-530), which Smith extended to conversion of a chlorin to the methyl pheophorbide a (E→F)(Smith, K. M.; Lewis, W. M. *Tetrahedron* 1981, 37 Supp. 1, 399-403). Finally, a dipyrromethane bearing an annulated cyclopentane ring (G) has provided an intriguing route to deoxophylloerythroetioporphyrin (H), although this macrocycle does not contain the desired $13^1$-oxo functionality (Flaugh, M. E.; Rapoport, H. *J. Am. Chem. Soc.* 1968, 90, 6877-6879; Li, W.; Lash, T. D. *Tetrahedron Lett.* 1998, 39, 8571-8574; Lash, T. D.; Catarello, J. J. *Tetrahedron* 1993, 49, 4159-4172). Each of these routes has certain attractions; however, none appeared compatible with our existing synthetic route to chlorins.

SUMMARY OF THE INVENTION

Examples of porphyrinic macrocycles containing a fused "E" ring useful for carrying out the present invention include compounds of Formula DI:

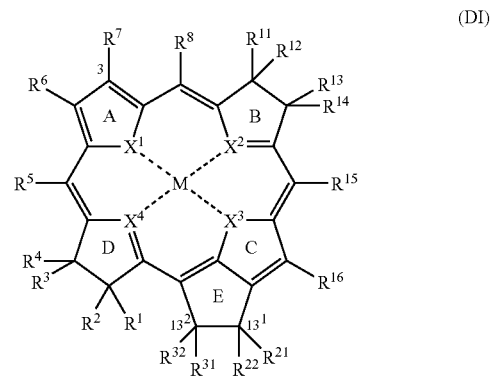

(DI)

wherein:
M is a metal or is absent;
$X^1, X^2, X^3$ and $X^4$ are each independently selected from the group consisting of Se, NH, $CH_2$, O and S;
$R^1, R^2, R^3, R^4, R^5, R^6, R^7, R^8, R^{11}, R^{12}, R^{13}, R^{14}, R^{15}, R^{16}, R^{21}, R^{22}, R^{31}$ and $R^{32}$ are each independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, acyl, formyl, carboxylic acid, acylamino, ester, amide, hydroxyl, nitro, alkylthio, amino, alkylamino, arylalkylamino, disubstituted amino, acyloxy, sulfoxyl, sulfonyl, sulfonate, sulfonic acid, sulfonamide, urea, alkoxylacylamino, aminoacyloxy, linking groups, surface attachment groups, bioconjugatable groups, targeting groups (in protected or unprotected form), and water soluble groups;
wherein each pair of $R^1$ and $R^2$, $R^3$ and $R^4$, $R^{11}$ and $R^{12}$, $R^{13}$ and $R^{14}$, $R^{21}$ and $R^{22}$, or $R^{31}$ and $R^{32}$, can together form =O;
wherein each of $R^1$ and $R^2$, $R^3$ and $R^4$, $R^{11}$ and $R^{12}$, or $R^{13}$ and $R^{14}$, can together form spiroalkyl;
wherein $R^2$ and $R^3$ can together form a double bond; and wherein $R^{12}$ and $R^{13}$ can together form a double bond;
or a salt thereof;
In some embodiments, such compounds are subject to the proviso that: (i) neither $R^1$ nor $R^2$ is H; or neither $R^3$ nor $R^4$ is H; or neither $R^{11}$ nor $R^{12}$ is H; or neither $R^{13}$ nor $R^{14}$ is H.
Some embodiments of the foregoing are subject to the proviso that: (i) at least one of $R^1$, $R^2$, $R^3$, $R^4$, $R^5$, $R^6$, $R^7$, $R^8$, $R^{11}$, $R^{12}$, $R^{13}$, $R^{14}$, $R^{15}$, $R^{16}$, $R^{21}$, $R^{22}$, $R^{31}$ and $R^{32}$ is a group of the Formula:

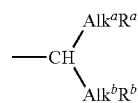

wherein $R^a$ and $R^b$ are each an independently selected ionic group, polar group, bioconjugatable group, or targeting group (in protected or unprotected form), and $Alk^a$ and $Alk^b$ are each an independently selected C1-C50 alkylidene chain.

Some embodiments of the foregoing are subject to the proviso that at least one pair of $R^{11}$ and $R^{12}$, $R^{13}$ and $R^{14}$, $R^{21}$ and $R^{22}$, and $R^{23}$ and $R^{24}$ are both independently selected Alk'R', wherein Alk' is a C1-C50 alkylidene chain, and R' is an ionic group, polar group, bioconjugatable group, or targeting group (in protected or unprotected form).

A further aspect of the invention is a method for treating a target in a subject in need thereof, comprising: (i) administering to the subject the active compound as described herein or a pharmaceutically acceptable conjugate thereof that preferentially associates with the target, and (ii) irradiating the target with light of a wavelength and intensity sufficient to treat the target. Suitable subjects include but are not limited to subjects afflicted with opportunistic infections, with burns (particularly burns that have become infected), sepsis, with ulcers, periodontal disease, atherosclerosis, cosmetic and dermatologic conditions, acne, infectious diseases, tissues that require sealing such as in wounds or surgical incisions, and subjects afflicted with neoplastic disease or cancer.

A further aspect of the invention is a photodynamic therapy method for treating hyperproliferative tissue in a subject in need thereof, comprising: (i) administering to the subject an active compound as described herein or a pharmaceutically acceptable conjugate thereof that preferentially associates with the hyperproliferative tissue, and (ii) irradiating the target with light of a wavelength and intensity sufficient to activate the compound, and thereby treat the hyperproliferative tissue.

A further aspect of the invention is a method for detecting the presence of a target such as hyperproliferative tissue in a subject, comprising: (i) administering to the subject an active compound as described herein or a pharmaceutically acceptable conjugate thereof that preferentially associates with the target; and then (ii) visualizing the compound within the patient.

A further aspect of the present invention is a kit to treat hyperproliferative disorders, comprising the active compound described herein or a pharmaceutically acceptable conjugate thereof and instructions teaching a method of photodynamic therapy.

A further aspect of the present invention is a kit to label specific tissues for diagnosis comprising the active compound described herein or a pharmaceutically acceptable conjugate thereof and instructions teaching a method of imaging (e.g., magnetic resonance imaging).

The foregoing and other objects and aspects of the invention are explained in greater detail in the specification set forth below.

BRIEF DESCRIPTION OF THE DRAWINGS

FIG. 1. Absorption spectra of 13-acetylchlorin Zn-8 ($Q_y$ at 632 nm) vs. the chlorin lacking the 13-acetyl group Zn-11 ($Q_y$ at 608 nm). The spectra were obtained in toluene at room temperature and are normalized at the B bands.

FIG. 2. Absorption spectra of oxophorbine 10 ($Q_y$ at 660 nm) vs. the chlorin lacking the $13^1$-oxo group 11 ($Q_y$ at 641 nm. The spectra were obtained in toluene at room temperature and are normalized at the B bands.

FIG. 3. Absorption spectra of chlorophylls a and b (in diethyl ether at room temperature). The $Q_y$ band in chlorophyll a or b appears at 662 or 644 nm, respectively.

FIG. 4. Absorption spectra in toluene at room temperature of a selection of zinc chlorins (10-mesityl family) bearing substituents at the 3- and/or 13-positions (normalized at the B bands). The chlorins (b-f) and their $Q_y$ bands include ZnC-$M^{10}$ (a) 606 nm; ZnC-$V^3M^{10}$ (b) 621 nm; ZnC-$E^3M^{10}$ (c) 627 nm; ZnC-$M^{10}A^{13}$ (d) 632 mm; ZnC-$E^3M^{10}E^{13}$ (e) 646 nm; and ZnC-$E^3M^{10}A^{13}$ (f) 652 ml. The B/$Q_y$ band intensity ratio decreases from 4.2 in ZnC-$M^{10}$ to 1.5 in ZnC-$E^3M^{10}A^{13}$.

FIG. 5. Absorption spectra in toluene at room temperature of zinc chlorins (10-unsubstituted family) bearing substituents at the 3,13-positions (normalized at the B bands). The chlorins (b, c) and their $Q_y$ bands include ZnC (a) 603 mm; ZnC-$E^3E^{13}$ (b) 645 mm; and ZnC-$E^3A^{13}$ (c) 655 nm. The B/$Q_y$ band intensity ratio decreases from 3.2 in ZnC to 1.2 in ZnC-$E^3A^{13}$.

DETAILED DESCRIPTION OF THE PREFERRED EMBODIMENTS

The disclosures of all United States Patent references cited herein are to be incorporated by reference herein as if fully set forth.

"Halo" as used herein refers to any suitable halogen, including —F, —Cl, —Br, and —I.

"Mercapto" as used herein refers to an —SH group.

"Azido" as used herein refers to an —$N_3$ group.

"Cyano" as used herein refers to a —CN group.

"Hydroxyl" as used herein refers to an —OH group.

"Nitro" as used herein refers to an —$NO_2$ group.

"Alkyl" as used herein alone or as part of another group, refers to a straight or branched chain hydrocarbon containing from 1 or 2 to 10, 20 or 50 carbon atoms (e.g., C1 to C4 alkyl; C4 to C10 alkyl; C11 to C50 alkyl). Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. "Loweralkyl" as used herein, is a subset of alkyl, in some embodiments preferred, and refers to a straight or branched chain hydrocarbon group containing from 1 to 4 carbon atoms. Representative examples of loweralkyl include, but are not limited to, methyl, ethyl, n-propyl, iso-propyl, n-butyl, iso-butyl, tert-butyl, and the like. The term "alkyl" or "loweralkyl" is intended to include both substituted and unsubstituted alkyl or loweralkyl unless otherwise indicated and these groups may be substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocycloalkyloxy, mercapto, alkyl-$S(O)_m$, haloalkyl-$S(O)_m$, alkenyl-$S(O)_m$, alkynyl-$S(O)_m$, cycloalkyl-$S(O)_m$, cycloalkylalkyl-$S(O)_m$, aryl-$S(O)_m$, arylalkyl-$S(O)_m$, heterocyclo-$S(O)_m$, heterocycloalkyl-$S(O)_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Alkylene" as used herein refers to a difunctional linear, branched or cyclic alkyl group, which may be substituted or unsubstituted, and where "alkyl" is as defined above.

"Alkenyl" as used herein alone or as part of another group, refers to a straight or branched chain hydrocarbon containing from 1 or 2 to 10, 20 or 50 carbon atoms (e.g., C1 to C4 alkenyl; C4 to C10 alkenyl; C11 to C50 alkenyl) (or in loweralkenyl 1 to 4 carbon atoms) which include 1 to 4 double bonds in the normal chain. Representative examples of alkenyl include, but are not limited to, vinyl, 2-propenyl, 3-butenyl, 2-butenyl, 4-pentenyl, 3-pentenyl, 2-hexenyl, 3-hexenyl, 2,4-heptadienyl, and the like. The term "alkenyl" or "loweralkenyl" is intended to include both substituted and unsubstituted alkenyl or loweralkenyl unless otherwise indicated and these groups may be substituted with groups as described in connection with alkyl and loweralkyl above.

"Alkenylene" as used herein refers to a difunctional linear, branched or cyclic alkyl group, which may be substituted or unsubstituted, and where "alkenyl" is as defined above.

"Alkynyl" as used herein alone or as part of another group, refers to a straight or branched chain hydrocarbon containing from 1 or 20 to 10, 20 or 50 carbon atoms (e.g., C1 to C4 alkynyl; C4 to C10 alkynyl; C11 to C50 alkynyl) (or in loweralkynyl 1 to 4 carbon atoms) which include 1 triple bond in the normal chain. Representative examples of alkynyl include, but are not limited to, 2-propynyl, 3-butynyl, 2-butynyl, 4-pentynyl, 3-pentynyl, and the like. The term "alkynyl" or "loweralkynyl" is intended to include both substituted and unsubstituted alkynyl or loweralknynyl unless otherwise indicated and these groups may be substituted with the same groups as set forth in connection with alkyl and loweralkyl above.

"Alkynylene" as used herein refers to a difunctional linear, branched or cyclic alkynyl group, which may be substituted or unsubstituted, and where "alkynyl" is as defined above.

"Alkylidene chain" as used herein refers to a difunctional linear, branched, and/or cyclic organic group, which may be substituted or unsubstituted, which may be saturated or unsaturated, and which may optionally contain one, two or three heteroatoms selected from the group consisting of N, O, and S. Examples include but are not limited to alkylene, alkenylene, alkynylene, arylene, alkarylene, and aralkylene. See, e.g., U.S. Pat. No. 6,946,533. The alkylidene chain may contain any suitable number of carbon atoms (e.g., a C1 to C4; C4 to C10; C10 to C20; C20 to C50).

"Alkoxy" as used herein alone or as part of another group, refers to an alkyl or loweralkyl group, as defined herein, appended to the parent molecular moiety through an oxy group, —O—. Representative examples of alkoxy include, but are not limited to, methoxy, ethoxy, propoxy, 2-propoxy, butoxy, tert-butoxy, pentyloxy, hexyloxy and the like.

"Acyl" as used herein alone or as part of another group refers to a —C(O)R radical, where R is any suitable substituent such as aryl, alkyl, alkenyl, alkynyl, cycloalkyl or other suitable substituent as described herein.

"Haloalkyl" as used herein alone or as part of another group, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, 2-chloro-3-fluoropentyl, and the like.

"Alkylthio" as used herein alone or as part of another group, refers to an alkyl group, as defined herein, appended to the parent molecular moiety through a thio moiety, as defined herein. Representative examples of alkylthio include, but are not limited to, methylthio, ethylthio, tert-butylthio, hexylthio, and the like.

"Aryl" as used herein alone or as part of another group, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like. The term "aryl" is intended to include both substituted and unsubstituted aryl unless otherwise indicated and these groups may be substituted with the same groups as set forth in connection with alkyl and loweralkyl above.

"Arylalkyl" as used herein alone or as part of another group, refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-ylethyl, and the like.

"Amino" as used herein means the radical —$NH_2$.

"Alkylamino" as used herein alone or as part of another group means the radical —NHR, where R is an alkyl group.

"Arylalkylamino" as used herein alone or as part of another group means the radical —NHR, where R is an arylalkyl group.

"Disubstituted-amino" as used herein alone or as part of another group means the radical —$NR_aR_b$, where $R_a$ and $R_b$ are independently selected from the groups alkyl, haloalkyl, alkenyl, alkynyl, cycloalkyl, cycloalkylalkyl, aryl, arylalkyl, heterocyclo, heterocycloalkyl.

"Acylamino" as used herein alone or as part of another group means the radical —$NR_aR_b$, where $R_a$ is an acyl group as defined herein and $R_b$ is selected from the groups hydrogen, alkyl, haloalkyl, alkenyl, alkynyl, cycloalkyl, cycloalkylalkyl, aryl, arylalkyl, heterocyclo, heterocycloalkyl.

"Acyloxy" as used herein alone or as part of another group means the radical —OR, where R is an acyl group as defined herein.

"Ester" as used herein alone or as part of another group refers to a —C(O)OR radical, where R is any suitable substituent such as alkyl, cycloalkyl, alkenyl, alkynyl or aryl.

"Formyl" as used herein refers to a —C(O)H group.

"Carboxylic acid" as used herein refers to a —C(O)OH group.

"Sulfoxyl" as used herein refers to a compound of the formula —S(O)R, where R is any suitable substituent such as alkyl, cycloalkyl, alkenyl, alkynyl or aryl.

"Sulfonyl" as used herein refers to a compound of the formula —S(O)(O)R, where R is any suitable substituent such as alkyl, cycloalkyl, alkenyl, alkynyl or aryl.

"Sulfonate" as used herein refers to a compound of the formula —S(O)(O)OR, where R is any suitable substituent such as alkyl, cycloalkyl, alkenyl, alkynyl or aryl.

"Sulfonic acid" as used herein refers to a compound of the formula —S(O)(O)OH.

"Amide" as used herein alone or as part of another group refers to a —$C(O)NR_aR_b$ radical, where $R_a$ and $R_b$ are any suitable substituent such as H, alkyl, cycloalkyl, alkenyl, alkynyl or aryl.

"Sulfonamide" as used herein alone or as part of another group refers to a —$S(O)_2NR_aR_b$ radical, where $R_a$ and $R_b$ are any suitable substituent such as H, alkyl, cycloalkyl, alkenyl, alkynyl or aryl.

"Urea" as used herein alone or as part of another group refers to an —$N(R_c)C(O)NR_aR_b$ radical, where $R_a$, $R_b$ and $R_c$ are any suitable substituent such as H, alkyl, cycloalkyl, alkenyl, alkynyl or aryl.

"Alkoxyacylamino" as used herein alone or as part of another group refers to an —$N(R_a)C(O)OR_b$ radical, where $R_a$, $R_b$ are any suitable substituent such as H, alkyl, cycloalkyl, alkenyl, alkynyl or aryl.

"Aminoacyloxy" as used herein alone or as part of another group refers to an —$OC(O)NR_aR_b$ radical, where $R_a$ and $R_b$ are any suitable substituent such as H, alkyl, cycloalkyl, alkenyl, alkynyl or aryl.

"Cycloalkyl" as used herein alone or as part of another group, refers to a saturated or partially unsaturated cyclic hydrocarbon group containing from 3, 4 or 5 to 6, 7 or 8 carbons (which carbons may be replaced in a heterocyclic group as discussed below). Representative examples of cycloalkyl include, cyclopropyl, cyclobutyl, cyclopentyl, cyclohexyl, cycloheptyl, and cyclooctyl. These rings may be optionally substituted with additional substituents as described herein such as halo or loweralkyl. The term "cycloalkyl" is generic and intended to include heterocyclic groups as discussed below unless specified otherwise.

"Heterocyclic group" or "heterocyclo" as used herein alone or as part of another group, refers to an aliphatic (e.g., fully or partially saturated heterocyclo) or aromatic (e.g., heteroaryl) monocyclic- or a bicyclic-ring system. Monocyclic ring systems are exemplified by any 5 or 6 membered ring containing 1, 2, 3, or 4 heteroatoms independently selected from oxygen, nitrogen and sulfur. The 5 membered ring has from 0-2 double bonds and the 6 membered ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, purine, pyranopyridine, quinoline, quinolizine, quinoxaline, quinazoline, tetrahydroisoquinoline, tetrahydroquinoline, thiopyranopyridine, and the like. These rings include quaternized derivatives thereof and may be optionally substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocycloalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3. Preferred heterocyclo groups include pyridyl and imidazolyl groups, these terms including the quaternized derivatives thereof, including but not limited to quaternary pyridyl and imidazolyl groups, examples of which include but are not limited to:

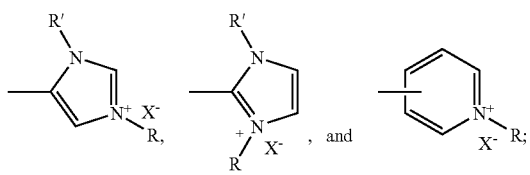

where R and R' are each a suitable substituent as described in connection with "alkyl" above, and particularly alkyl (such as methyl, ethyl or propyl), arylalkyl (such as benzyl), optionally substituted with hydroxy (—OH), phosphonic acid (—PO$_3$H$_2$) or sulfonic acid (—SO$_3$H), and X$^-$ is a counterion.

"Spiroalkyl" as used herein alone or as part of another group, refers to a straight or branched chain hydrocarbon, saturated or unsaturated, containing from 3 to 8 carbon atoms. Representative examples include, but are not limited to, —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$CHCHCH$_2$—, —CH$_2$CH$_2$CH$_2$CH$_2$CH$_2$CH$_2$—, etc. The term "spiroalkyl" is intended to include both substituted and unsubstituted "spiroalkyl" unless otherwise indicated and these groups may be substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocycloalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1 or 2.

"Aldehyde" as used herein refers to a group of the formula:

"Acetal" as used herein refers to a group of the formula:

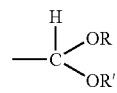

where R and R' are each suitable groups, e.g., groups independently selected from the group consisting of alkyl, aryl, alkylaryl, or where R and R' together form a group —R"— where R" is an alkylene (i.e., cycloalkyl). The acetal is preferably reasonably robust, and hence it is preferred that at least one, or more preferably both, of R and R' is not methyl, and it is particularly preferred that neither R nor R' is H.

"Bronsted acid" as used herein refers to a molecular entity (and corresponding chemical species) that is a proton donor to a base. Any suitable Bronsted acid may be used as a catalyst, with examples including but not limited to: trifluoroacetic acid, trichloroacetic acid, oxalic acid, taurine, malonic acid, formic acid, acetic acid, and NH$_4$Cl.

"Lewis acid" as used herein refers to a molecular entity (and corresponding chemical species) that is an electron-pair acceptor and therefore able to react with a Lewis base to form a Lewis adduct, by sharing the electron pair furnished by the Lewis base. Any suitable Lewis acid may be used as a catalyst, examples including compounds of the general formula LnX$_3$ where Ln is a lanthanide and X is halo such as Cl, Br, I, etc., triflate or OTf, etc., and with examples specific examples including but not limited to: Yb(OTf)$_3$, InCl$_3$, Sc(OTf)$_3$, MgBr$_2$ and CeCl$_3$.

"Porphyrinic macrocycle" refers to a porphyrin or porphyrin derivative, and are discussed in greater detail below.

"Macrocyclic ligand" as used herein means a macrocyclic molecule of repeating units of carbon atoms and hetero atoms (e.g., O, S, or NH), separated by the carbon atoms (generally by at least two or three carbon atoms). Macrocyclic ligands exhibit a conformation with a so-called hole capable of trapping ions or molecules, particularly cations, by coordination with the electrons of the hetero atom (e.g., a lone pair of electrons on the oxygen atoms when the hetero atoms are oxygen). In general, the macrocyclic ring contains at least 9, 12 or 14 carbon atoms and hetero atoms (e.g., O, S, NH), each hetero atom in the ring being separated from adjoining hetero atoms in the ring by two or more carbon atoms. The macrocyclic ring may be substituted or unsubstituted, and may be fused to additional rings (e.g., 1 to 4 additional rings such as phenylene, naphthylene, phenanthrylene, and anthrylene rings). The macrocyclic ligand may be in the form of a substituent. See, e.g., U.S. Pat. No. 6,411,164 to Sibert.

"Crown ether" as used herein means a macrocyclic polyether whose structure exhibits a conformation with a so-called hole capable of trapping cations by coordination with a lone pair of electrons on the oxygen atoms (see generally McGraw-Hill Dictionary of Scientific and Technical Terms (3d ed. 1984)). Crown ethers are a species of macrocyclic ligand. The crown ether may be in the form of a substituent. See, e.g., U.S. Pat. No. 6,411,164 to Sibert.

"Polar group" as used herein refers to a group wherein the nuclei of the atoms covalently bound to each other to form the group do not share the electrons of the covalent bond(s) joining them equally; that is the electron cloud is denser about one atom than another. This results in one end of the covalent bond(s) being relatively negative and the other end relatively positive; i.e., there is a negative pole and a positive pole. Examples of polar groups include, without limitations, hydroxy, alkoxy, carboxy, nitro, cyano, amino (primary, secondary and tertiary), amido, ureido, sulfonamido, sulfinyl, sulfhydryl, silyl, S-sulfonamido, N-sulfonamido, C-carboxy, O-carboxy, C-amido, N-amido, sulfonyl, phosphono, morpholino, piperazinyl, tetrazolo, and the like. See, e.g., U.S. Pat. No. 6,878,733, as well as alcohol, thiol, polyethylene glycol, polyol (including sugar, aminosugar, uronic acid), sulfonamide, carboxamide, hydrazide, N-hydroxycarboxamide, urea, metal chelates (including macrocyclic ligand or crown ether metal chelates) "Ionic group" as used herein includes anionic and cationic groups, and includes groups (sometimes referred to as "ionogenic" groups) that are uncharged in one form but can be easily converted to ionic groups (for example, by protonation or deprotonation in aqueous solution). Examples include but are not limited to carboxylate, sulfonate, phosphate, amine, N-oxide, and ammonium (including quaternized heterocyclic amines such as imidazolium and pyridinium as described above) groups. See, e.g., U.S. Pat. Nos. 6,478,863; 6,800,276; and 6,896,246. Additional examples include uronic acids, carboxylic acid, sulfonic acid, amine, and moieties such as guanidinium, phosphoric acid, phosphonic acid, phosphatidyl choline, phosphonium, borate, sulfate, etc. Note that compounds of the present invention can contain both an anionic group as one ionic substituent and a cationic group as another ionic substituent, with the compounds hence being zwitterionic. Note also that the compounds of the invention can contain more than one anionic or more than one cationic group.

"Protecting group" as used herein includes any suitable protecting group; "protected form" refers to a substituent in which an atom such as hydrogen has been removed and replaced with a corresponding protecting group. Protecting groups are known. See generally T. H. Greene and P. G. M. Wuts, *Protective Groups in Organic Synthesis,* 3rd edition, John Wiley & Sons, New York (1999). Examples include but are not limited to: hydroxy protecting groups (for producing the protected form of hydroxy); carboxy protecting groups (for producing the protected form of carboxylic acid); amino-protecting groups (for producing the protected form of amino); sulfhydryl protecting groups (for producing the protected form of sulfhydryl); etc. Particular examples include but are not limited to: benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilylethyl, 1,1-dimethyl-2-propenyl, 3-methyl-3-butenyl, allyl, benzyl, para-methoxybenzyldiphenylmethyl, triphenylmethyl (trityl), tetrahydrofuryl, methoxymethyl, methylthiomethyl, benzyloxymethyl, 2,2,2-triehloroethoxymethyl, 2-(trimethylsilyl)ethoxymethyl, methanesulfonyl, para-toluenesulfonyl, trimethylsilyl, triethylsilyl, triisopropylsilyl, acetyl (Ac or —C(O)CH$_3$), benzoyl (Bn or —C(O)C$_6$H$_5$), and trimethylsilyl (TMS or —Si(CH$_3$)$_3$), and the like; formyl, acetyl, benzoyl, pivaloyl, t-butylacetyl, phenylsulfonyl, benzyl, t-butyloxycarbonyl (Boc), and benzyloxycarbonyl (Cbz) and the like; and hemithioacetals such as 1-ethoxyethyl and methoxymethyl, thioesters, or thiocarbonates and the like. See, e.g., U.S. Pat. Nos. 6,953,782; 6,951,946; 6,951,942; and 6,051,724.

"Treatment" as used herein means any manner in which one or more of the symptoms of a disease or disorder are ameliorated or otherwise beneficially altered. Treatment also encompasses any pharmaceutical use of the compositions herein, such as use for treating hyperproliferating tissue or neovascularization mediated diseases or disorders, or diseases or disorders in which hyperproliferating tissue or neovascularization is implicated. As used herein, amelioration of the symptoms of a particular disorder by administration of a particular compound or pharmaceutical composition refers to any lessening, whether permanent or temporary, lasting or transient that can be attributed to or associated with administration of the composition.

"Prodrug" as used herein is a compound that, upon in vivo administration, is metabolized by one or more steps or processes or otherwise converted to the biologically, pharmaceutically or therapeutically active form of the compound.

"Antibody" as used herein refers generally to immunoglobulins or fragments thereof that specifically bind to antigens to form immune complexes. The antibody may be whole immunoglobulin of any class, e.g., IgG, IgM, IgA, IgD, IgE, chimeric or hybrid antibodies with dual or multiple antigen or epitope specificities. It can be a polyclonal antibody, preferably an affinity-purified antibody from a human or an appropriate animal, e.g., a primate, goat, rabbit, mouse or the like. Monoclonal antibodies are also suitable for use in the present invention, and are preferred because of their high specificities. They are readily prepared by what are now considered conventional procedures of immunization of mammals with immunogenic antigen preparation, fusion of immune lymph or spleen cells with an immortal myeloma cell line, and isolation of specific hybridoma clones. More unconventional methods of preparing monoclonal antibodies are not excluded, such as interspecies fusions and genetic engineering manipulations of hypervariable regions, since it is primarily the antigen specificity of the antibodies that affects their utility. Newer techniques for production of monoclonals can also be used, e.g., human monoclonals, interspecies monoclonals, chimeric (e.g., human/mouse) monoclonals, genetically engineered antibodies and the like.

"Irradiating" and "irradiation" as used herein includes exposing a subject to all wavelengths of light. Preferably, the irradiating wavelength is selected to match the wavelength(s) which excite the photosensitive compound. Preferably, the radiation wavelength matches the excitation wavelength of the photosensitive compound and has low absorption by the non-target tissues of the subject, including blood proteins.

"Biological materials" as used herein refers to both tissues (such as biopsy tissues) and cells, as well as biological fluids such as blood, urine, plasma, cerebrospinal fluid, mucus, sputum, etc.

Irradiation is further defined herein by its coherence (laser) or non-coherence (non-laser), as well as intensity, duration, and timing with respect to dosing using the photosensitizing compound. The intensity or fluence rate must be sufficient for the light to reach the target tissue. The duration or total fluence dose must be sufficient to photoactivate enough photosensitizing compound to act on the target tissue. Timing with respect to dosing with the photosensitizing compound is important, because 1) the administered photosensitizing compound requires some time to home in on target tissue and 2) the blood level of many photosensitizing compounds decreases with time. The radiation energy is provided by an energy source, such as a laser or cold cathode light source, that is external to the subject, or that is implanted in the subject, or that is introduced into a subject, such as by a catheter, optical fiber or by ingesting the light source in capsule or pill form (e.g., as disclosed in. U.S. Pat. No. 6,273,904 (2001)).

"Coupling agent" as used herein, refers to a reagent capable of coupling a photosensitizer to a targeting agent "Targeting agent" refers to a compound that homes in on or preferentially associates or binds to a particular tissue, receptor, infecting agent or other area of the body of the subject to be treated, such as a target tissue or target composition. Examples of a targeting agent include but are not limited to an antibody, a ligand, one member of a ligand-receptor binding pair, nucleic acids, proteins and peptides, and liposomal suspensions, including tissue-targeted liposomes.

"Specific binding pair" and "ligand-receptor binding pair" as used herein refers to two different molecules, where one of the molecules has an area on the surface or in a cavity which specifically attracts or binds to a particular spatial or polar organization of the other molecule, causing both molecules to have an affinity for each other. The members of the specific binding pair are referred to as ligand and receptor (antiligand). The terms ligand and receptor are intended to encompass the entire ligand or receptor or portions thereof sufficient for binding to occur between the ligand and the receptor. Examples of ligand-receptor binding pairs include, but are not limited to, hormones and hormone receptors, for example epidermal growth factor and epidermal growth factor receptor, tumor necrosis factor-.alpha. and tumor necrosis factor-receptor, and interferon and interferon receptor; avidin and biotin or antibiotin; antibody and antigen pairs; enzymes and substrates, drug and drug receptor; cell-surface antigen and lectin; two complementary nucleic acid strands; nucleic acid strands and complementary oligonucleotides; interleukin and interleukin receptor; and stimulating factors and their receptors, such as granulocyte-macrophage colony stimulating factor (GMCSF) and GMCSF receptor and macrophage colony stimulating factor (MCSF) and MCSF receptor.

"Linkers", or "linker groups" are aromatic or aliphatic groups (which may be substituted or unsubstituted and may optionally contain heteroatoms such as N, O, or S) that are utilized to couple a bioconjugatable group, cross-coupling group, surface attachment group, hydrophilic group or the like to the parent molecule. Examples include but are not limited to aryl, alkyl, heteroaryl, heteroalkyl (e.g., oligoethylene glycol), peptide, and polysaccharide linkers, etc.

"Water soluble group" as used herein generally includes substituents containing at least one ionic or polar group, coupled to the parent molecule directly or by means of an intervening linker. Examples include but are not limited to groups of the formula:

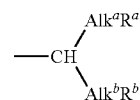

wherein $R^a$ and $R^b$ are each independently an ionic group or polar group, and $Alk^a$ and $Alk^b$ are each independently a C1-C50 alkylidene chain.

1. Active Compounds: Phorbines and Related Compounds.

Porphyrinic macrocycle compounds useful for carrying out the present invention include compounds of general Formula DI and DI':

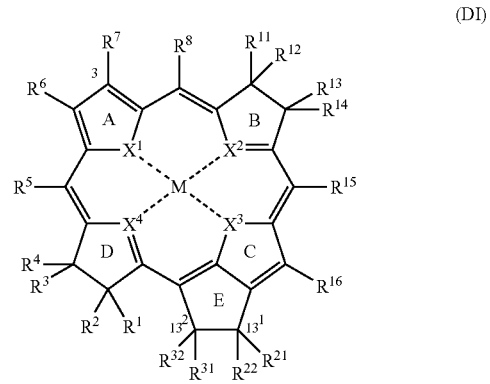

(DI)

-continued
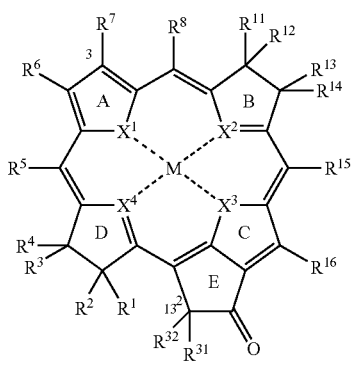
(DI')
with particular embodiments of the foregoing including: (a) 17,18-didehydrophorbines of Formula DIa and DIa':
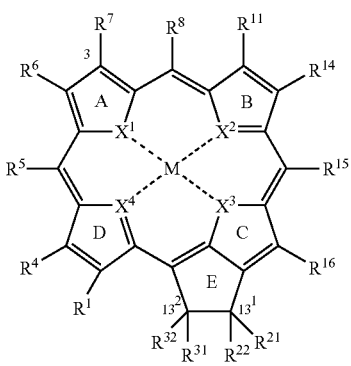
(DIa)
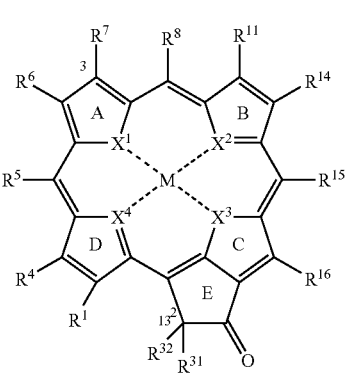
(DIa')
(b) phorbines of Formula DIb and DIb':
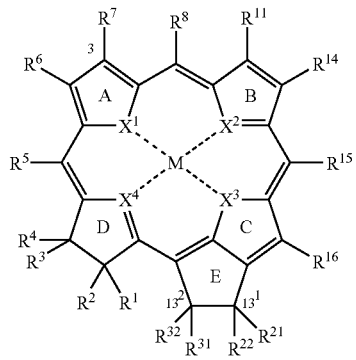
(DIb)
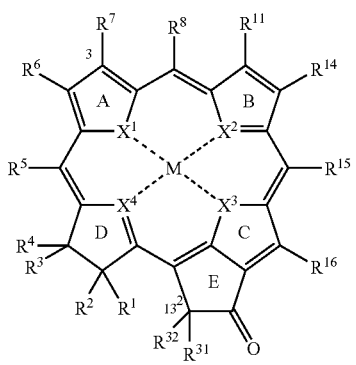
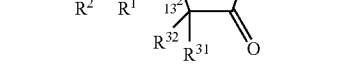
(DIb')
(c) bacteriophorbines of Formula DIc and DIc':
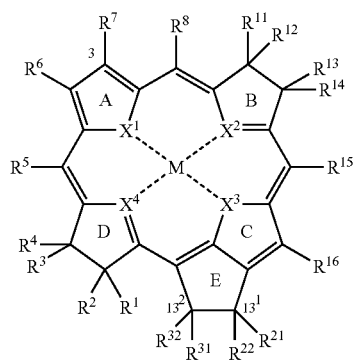
(DIc)
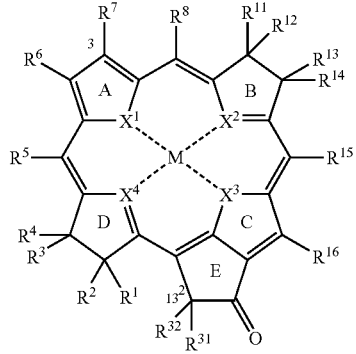
(DIc')

and (d) opp-chlorins, or opp-phorbines, of Formula DId and DId':

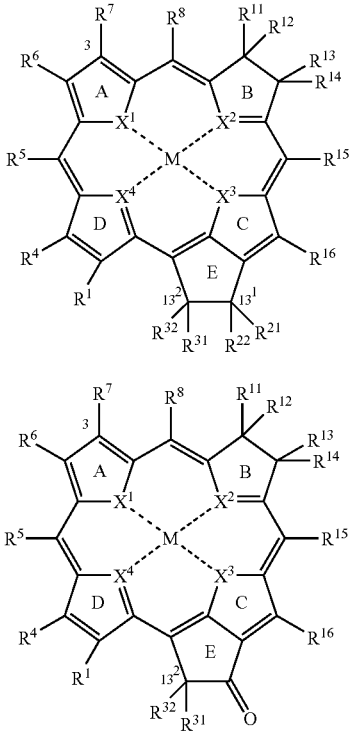

(DId)

(DId')

wherein:

M is a metal or is absent;

$X^1, X^2, X^3$ and $X^4$ are each independently selected from the group consisting of Se, NH, CH$_2$, O and S;

$R^1, R^2, R^3, R^4, R^5, R^6, R^7, R^8, R^{11}, R^{12}, R^{13}, R^{14}, R^{15}, R^{16}, R^{21}, R^{22} R^{31}$ and $R^{32}$ are each independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, acyl, formyl, carboxylic acid, acylamino, ester, amide, hydroxyl, nitro, alkylthio, amino, alkylamino, arylalkylamino, disubstituted amino, acyloxy, sulfoxyl, sulfonyl, sulfonate, sulfonic acid, sulfonamide, urea, alkoxyacylamino, aminoacyloxy, linking groups, surface attachment groups, bioconjugatable groups, targeting groups (in protected or unprotected form), and water soluble groups;

wherein each pair of $R^1$ and $R^2$, $R^3$ and $R^4$, $R^{11}$ and $R^{12}$, $R^{13}$ and $R^{14}$, $R^{21}$ and $R^{22}$, or $R^{31}$ and $R^{32}$, can together form =O;

wherein each of $R^1$ and $R^2$, $R^3$ and $R^4$, $R^{11}$ and $R^{12}$, or $R^{13}$ and $R^{14}$, can together form spiroalkyl;

wherein $R^2$ and $R^3$ can together form a double bond; and wherein $R^{12}$ and $R^{13}$ can together form a double bond;

or a salt thereof.

Some embodiments are subject to the proviso that: (i) neither $R^1$ nor $R^2$ is H; or neither $R^3$ nor $R^4$ is H; or neither $R^{11}$ nor $R^{12}$ is H; or neither $R^{13}$ nor $R^{14}$ is H.

Some embodiments are subject to the proviso that at least one of $R^1, R^2, R^3, R^4, R^5, R^6, R^7, R^8, R^{11}, R^{12}, R^{13}, R^{14}, R^{15}, R^{16}, R^{21}, R^{22}, R^{31}$ and $R^{32}$ is a group of the Formula:

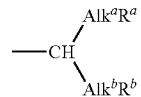

wherein $R^a$ and $R^b$ are each an independently selected ionic group, polar group, bioconjugatable group, or targeting group (in protected or unprotected form), and Alk$^a$ and Alk$^b$ are each an independently selected C1-C50 alkylidene chain.

Some embodiments of the foregoing are subject to the proviso that at least one pair of $R^{11}$ and $R^{12}$, $R^{13}$ and $R^{14}$, $R^{21}$ and $R^{22}$, and $R^{23}$ and $R^{24}$ are both independently selected Alk'R', wherein Alk' is a C1-C50 alkylidene chain, and R' is an ionic group, polar group, bioconjugatable group, or targeting group (in protected or unprotected form).

In some embodiments, $R^1$ and $R^2$ are both independently selected from the group consisting of alkyl, alkenyl, alkynyl, cycloalkyl, cycloalkylalkyl, cycloalkylalkenyl, cycloalkylalkynyl, aryl, arylalkyl, arylalkenyl, arylalkynyl, and linking groups; or $R^3$ and $R^4$ are both independently selected from the group consisting of alkyl, alkenyl, alkynyl, cycloalkyl, cycloalkylalkyl, cycloalkylalkenyl, cycloalkylalkynyl, aryl, arylalkyl, arylalkenyl, arylalkynyl, and linking groups; or $R^{11}$ and $R^{12}$ are both independently selected from the group consisting of alkyl, alkenyl, alkynyl, cycloalkyl, cycloalkylalkyl, cycloalkylalkenyl, cycloalkylalkynyl, aryl, arylalkyl, arylalkenyl, arylalkynyl, and linking groups; or $R^{13}$ and $R^{14}$ are both independently selected from the group consisting of alkyl, alkenyl, alkynyl, cycloalkyl, cycloalkylalkyl, cycloalkylalkenyl, cycloalkylalkynyl, aryl, arylalkyl, arylalkenyl, arylalkynyl, and linking groups.

In some embodiments, $R^1$ and $R^2$ are both independently selected from the group consisting of alkyl, cycloalkyl, aryl, arylalkyl, and linking groups; or $R^3$ and $R^4$ are both independently selected from the group consisting of alkyl, cycloalkyl, aryl, arylalkyl, and linking groups; or $R^{11}$ and $R^{12}$ are both independently selected from the group consisting of alkyl, cycloalkyl, aryl, arylalkyl, and linking groups; or $R^{13}$ and $R^{14}$ are both independently selected from the group consisting of alkyl, cycloalkyl, aryl, arylalkyl, and linking groups.

In some embodiments of the foregoing, at least one or two of $R^1, R^2, R^3, R^4, R^5, R^6, R^7, R^8, R^{11}, R^{12}, R^{13}, R^{14}, R^{15}, R^{16}, R^{17}, R^{18}, R^{21}, R^{22}, R^{31}$ and $R^{32}$ is, or are, independently selected bioconjugatable groups, targeting groups (in protected or unprotected form), surface attachment groups, or water soluble groups.

In some embodiments of the foregoing, at least one of $R^1, R^2, R^3, R^4, R^5, R^6, R^7, R^8, R^{11}, R^{12}, R^{13}, R^{14}, R^{15}, R^{16}, R^{17}, R^{18}, R^{21}, R^{22}, R^{31}$, and $R^{32}$ is a bioconjugatable group or targeting group (in protected or unprotected form), and at least one other thereof is a water soluble group.

In some embodiments of the foregoing, one of $R^3$ and $R^4$ can be a water soluble group, and the other of $R^3$ and $R^4$ can be a bioconjugatable group or targeting group.

In some embodiments of the foregoing, one of $R^{13}$ and $R^{14}$ can be a water soluble group, and the other of $R^{13}$ and $R^{14}$ can be a bioconjugatable group or targeting group.

In some embodiments, such as some of the chlorins of Formulas DIb, DIb', and some of the bacteriochlorins of Formulas DIc, DIc', neither $R^1$ nor $R^2$ is H.

In some embodiments, such as some of the chlorins of Formulas DIb, DIb', and some of the bacteriochlorins of Formulas DIc, DIc', neither $R^3$ nor $R^4$ is H.

In some embodiments, such as some of the chlorins of Formulas DIb, DIb', and some of the bacteriochlorins of Formulas DIc, DIc', none of $R^1$, $R^2$, $R^3$ and $R^4$ is H.

In some embodiments, such as some of the bacterochlorins Formulas DIc, DIc', and some of the opp-chlorins of Formulas DId, DId', neither $R^{11}$ nor $R^{12}$ is H.

In some embodiments, such as some bacterochlorins Formula DIc, DIc', and some of the opp-chlorins of Formulas DId, DId', neither $R^{13}$ nor $R^{14}$ is H.

In some embodiments, such as some of the bacterochlorins Formula DIc, DIc', and some of the opp-chlorins of Formulas DId, DId', none of $R^{11}$, $R^{12}$, $R^{13}$ and $R^{14}$ is H.

In general, compounds of Formula DI as described above may be produced by (a) providing a compound of Formula DII:

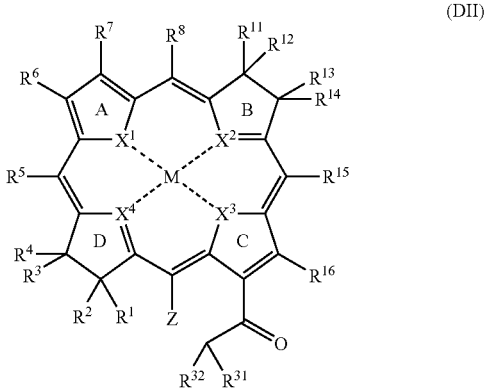

(DII)

wherein: Z is H or halo (such as bromo); and M, $X^1$, $X^2$, $X^3$, $X^4$, $R^1$, $R^2$, $R^3$, $R^4$, $R^5$, $R^6$, $R^7$, $R^8$, $R^{11}$, $R^{12}$, $R^{14}$, $R^{15}$, $R^{16}$, $R^{31}$ and $R^{32}$ are as given above;

(b) cyclizing said compound of Formula DII, typically by an intramolecular alpha arylation, to produce a cyclized product (that is, including the "E" ring as shown in DI); and (c) optionally deoxygenating the cyclized product; and then (d) optionally metalating the cyclized product to produce the compound of Formula DI. In some embodiments, $R^{31}$ and $R^{32}$ are each independently H, alkyl, or aryl; or one of $R^{31}$ and $R^{32}$ is H and the other is cyano; or one of $R^{31}$ and $R^{32}$ is H and the other is ester.

The cyclizing step is generally carried out in an organic solvent, optionally including water, by any suitable technique as discussed further below. For example, the cyclizing step may be carried out with a palladium catalyst in the presence of a base.

As also discussed further below, the compound of Formula DII may be produced by halogenating a compound of Formula DIII:

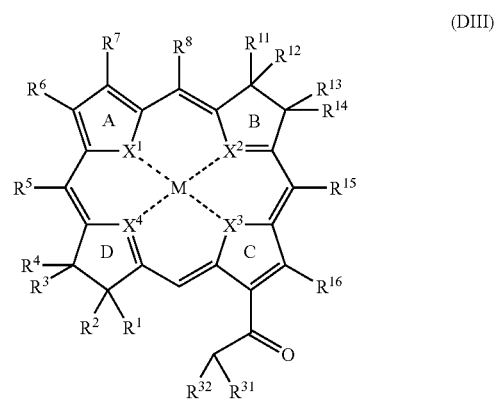

(DIII)

wherein M, $X^1$, $X^2$, $X^3$ $X^4$, $R^1$, $R^2$, $R^3$, $R^4$, $R^5$, $R^6$, $R^7$, $R^8$, $R^{11}$, $R^{12}$ $R^{13}$, $R^{14}$, $R^{15}$, $R^{16}$, $R^{31}$ and $R^{32}$ are as given above. The compound of Formula DIII can be produced in accordance with known techniques or variations thereof which will be apparent to those skilled in the art based upon the present disclosure.

Intramolecular α-arylation (Pd-coupling): The intermolecular and intramolecular α-arylation of certain ketones with a halo group (e.g. Cl, Br, I) present at a suitable position is known.

The intramolecular cyclization step of the present invention can be carried out in like manner, or variations thereof that will be apparent to those skilled in the art in view of the present disclosure.

In general the reaction involves a palladium catalyst and a base. Suitable palladium-catalysts include, but are not limited to, $Pd_2(dba)_3$/BINAP, $Pd_2(dba)_3$/Tol-BINAP, $Pd(OAc)_2$, $Pd_2(dba)_3$, $Pd_2(dba)_3$/2-(dicyclohexylphosphino)-biphenyl, $Pd(OAc)_2$/2-(dicyclohexylphosphino)-biphenyl, $Pd(OAc)_2$/2-(di-t-butylphosphino)-2'-methylbiphenyl, $Pd(dba)_2$/DTPE, $Pd(dba)_2$/DPPF, $Pd(OAc)_2$/Xantphos, $Pd(OAc)_2$/n-butylbis(1-adamantyl)-phosphine, $Pd(dba)_2$/n-butylbis(1-adamantyl)-phosphine, $Pd(OAc)_2$/$PPh_3$, $Pd(OAc)_2$/(4-$XC_6H_4$)$_3$P, $Pd_2(dba)_3$/Xantphos, $Pd(OAc)_2$/2-(Dicyclohexylphosphino)-2'-methylbiphenyl, $Pd(OAc)_2$/DPPP, $PdCl_2(Ph_3P)_2$, $PdCl_2[(o-Tol)_3]_2$, $Pd(Ph_3P)_4$, $Pd(OAc)_2$/P(t-Bu)$_3$, $Pd_2(dba)_3$/$CHCl_3$/BINAP, and combinations thereof.

Suitable bases include, but are not limited to, t-BuONa, $NaN(SiMe_3)_2$, $KN(SiMe_3)_2$, $Cs_2CO_3$, $K_2CO_3$, $K_3PO_4$, diisopropylamine, NaH, NaOH, t-BuOK, TBAF, and combinations thereof.

Any suitable organic solvent, including polar and nonpolar, and protic or aprotic solvents, may be used for the reaction, optionally including water, with examples including but not limited to THF, toluene, benzene, xylene, DMF, dioxane, DMSO, 1-Butyl-3-methylimidazolium tetrafluoroborate, and combinations thereof. The reaction may be carried out at any suitable temperature, typically from 20 or 40° C. up to 140° C., or more.

See, e.g., Muratake, H. et al., *Tetrahedron Lett.* 1997, 38, 7577-7580; Muratake, H.; Natsume, M. *Tetrahedron Lett.* 1997, 38, 7581-7582; Muratake, H.; Nakai, H. *Tetrahedron Lett.* 1999, 40, 2355-2358; Muratake, H. et al., *Tetrahedron* 2004, 60, 11783-11803; Sole, D. et al., *Adv. Synth. Catal.* 2001, 343, 439-442; Sole, D. et al., *J. Am. Chem. Soc.* 2003, 125, 1587-1594; Sole, D. et al., *Chem. Commun.* 2001, 1888-

1889; Sole, D. et al., *Org. Lett.* 2000, 2, 2225-2228; Ciufolini, M. A. et al., *J. Org. Chem.* 1988, 53, 4151-4153; Honda, T.; Sakamaki, Y. *Tetrahedron Lett.* 2005, 46, 6823-6825; See also, Palucki, M.; Buchwald, S. L. *J. Am. Soc. Chem.* 1997, 119, 11108-11109; Fox, J. M. et al., *J. Am. Soc. Chem.* 2000, 122, 1360-1370; Hamann, B. C.; Hartwig, J. F. *J. Am. Soc. Chem.* 1997, 119, 12382-12383; Carril, M. et al., *Org. Lett.* 2005, 22, 4787-4789; Ehrentraut, A. et al., *Adv. Synth. Catal.* 2002, 344, 209-217; Satoh, T. et al., *J. Organomet. Chem.* 2002, 653, 161-166; Wills, M. C. et al., *Angew. Chem. Int. Ed.* 2005, 44, 403-406; Diedrichs, N. et al., *Eur. J. Org. Chem.* 2005, 1731-1735; Mo, J. et al., *Tetrahedron* 2005, 61, 9902-9907; Singh, R.; Nolan, S. P. *J Organomet. Chem.* 2005, 690, 5832-5840; Kosugi, M. et al., *J. Chem. Soc., Chem. Commun.* 1983, 344-345; Kuwajima, I.; Urabe, H. *J. Am. Soc. Chem.* 1982, 104, 6831-6833.

An efficient reaction condition was reported for the direct arylation of ketones by the use of aryl chlorides in the presence of the carbene-palladium catalyst [(Pd(OAc)$_2$/N,N'-(2, 6-diisopropyl phenyl) imidazole-2-ylidene] (Singh, R.; Nolan, S. P. *J Organomet. Chem.* 2005, 690, 5832-5840), and the cyclizing step of the present invention can be carried out in like manner. Alternatively, the reaction of tributyltin enolates, prepared either from tributyltin methoxide and enol acetates or from silyl enol ethers and Bu$_3$SnF, in the presence of PdCl$_2$[P(o-tolyl)$_3$]$_2$ is reported to give α-arylated ketones (Kuwajima, I.; Urabe, H. *J. Am. Soc. Chem.* 1982, 104, 6831-6833), and the cyclizing step of the present invention can be carried out in like manner.

Photodriven nucleophilic aromatic substitution reaction: The α-arylation of ketones (intermolecular or intramolecular) has been studied by photostimulated nucleophilic aromatic substitution reaction of enolate anion with aryl halides, and the cyclizing step of the present invention can be carried out in like manner. The reaction is generally carried out in the presence of a base (suitable examples including but not limited to t-BuOK, KNH$_2$, NaNH$_2$, K, Na, Li, KH, Ag$_2$O, and mixtures thereof) in an organic solvent (suitable examples including but not limited to (liquid ammonia, THF, DME, ether, DMF, DMSO, benzene are commonly used solvents).

Still another approach for the intramolecular α-arylation of ketones involves the reaction of silyl enol ethers with the PET-generated arene radical cations.

See, e.g., Rossi, R. A.; Bunnett, J. F. *J. Org. Chem.* 1973, 38, 3020-3025; Bunnett, J. F.; Sundberg, J. E. *J. Org. Chem.* 1976, 41, 1702-1706; Komin, A. P.; Wolfe, J. F. *J. Org. Chem.* 1977, 42, 2481-2486; Moon, M. P.; Wolfe, J. F. *J. Org. Chem.* 1979, 44, 4081-4085; Sommelhack, M. F.; Bargar, T. M. *J. Org. Chem.* 1977, 42, 1481-1482; Semmelheck, M. F.; Bargar, T. *J. Am. Soc. Chem.* 1980, 102, 7765-7774; Pandey, G.; Karthikeyan, M.; Murugan, A. *J. Org. Chem.* 1998, 63, 2867-2872.

Other methods for α-arylation: A number of alternative routes have also been reported for the α-arylation of ketones, and the cyclizing step of the present invention can be carried out in like manner. For example:

(i) A nucleophilic aromatic substitution via Ni(II) catalyzed reaction of aryl halides with ketones has been reported (See, e.g., Semmelhack, M. F.; Stauffer, R. D.; Rogerson, T. D. *Tetrahedron Lett.* 1973, 4519-4522).

(ii) An alternative approach for the intramolecular α-arylation without halo substituents has been achieved with Mn(III) catalyst (See, e.g., Snider, B. B.; Cole, B. M. *J. Org. Chem.* 1995, 60, 5376-5377).

(iii) The electroreductive intramolcular cyclization of a carbonyl group to an activated carbon-carbon double bond has been described (no aryl halide is involved here) (See, e.g., Kise, N.; Suzumoto. T.; Shono, T. *J. Org. Chem.* 1994, 59, 1407-1413).

(iv) The electrophilic aromatic substitution of β-keto sulfoxides or tris(phenylthio)methane derivatives in the presence of an acid is known to give α-arylated ketones (no aryl halide is involved here) (See, e.g., Oikawa, Y.; Yonemitsu, O. *Tetrahedron* 1974, 30, 2653-2660; Oikawa, Y.; Yonemitsu, O. *J. Org. Chem.* 1976, 41, 1118-1124; Tamura, Y. et al., *Tetrahedron Lett.* 1981, 22, 81-84; Bin Manas, A. R.; Smith, R. A. J. *Tetrahedron* 1987, 43, 1856-1856).

In a particular embodiment, our synthetic route for installing the isocyclic ring entails four steps in addition to those required for macrocycle formation. The route is illustrated for chlorins in the Scheme A below, with substituents omitted for clarity.

Step 1: introduction of a halogen, preferably a bromine atom, at the 8-position of an Eastern half precursor to the chlorin (not shown). (Note that the Eastern half ordinarily incorporates a bromine atom at the 9-position for macrocycle formation; hence, the Eastern half used herein contains two bromine substituents.) The chlorin macrocycle is then formed in the usual way, affording the corresponding 13-bromo-chlorin (Br$^{13}$-chlorin).

Step 2: Pd coupling with tributyl(ethoxyvinyl)tin, which upon acidic workup affords the corresponding 13-acetyl-chlorin (Ac$^{13}$-chlorin).

Step 3: Halogenation of the chlorin, which occurs preferentially at the 15-position, affording the 13-acetyl-15-halo-chlorin (Ac$^{13}$X$^{15}$-chlorin). Bromination is preferred. Note that the sites flanking the reduced, pyrroline ring are more reactive than any other sites in the macrocycle. The preference for 15-versus 20-substitution stems from steric hindrance imparted by the geminal dimethyl group at the 18-position.

Step 4: Intramolecular α-arylation via Pd coupling, which creates a carbon-carbon bond between the methyl group of the acetyl moiety, and the meso (C$^{15}$) carbon, yielding the 13$^1$-oxophorbine.

An analogous approach is employed for synthesis of porphyrins or bacterichlorins bearing an isocyclic ring. A β-halo-dipyrromethane or dihydrodipyrrin precursor is prepared and employed to give the corresponding 13-halo-porphyrin or bacteriochlorin. The remaining steps 2-4 proceed as shown for the chlorin.

The keto group can be deoxygenated to give the phorbine (not shown). Typical methods of deoxygenation include (1) TFA/NaBH$_4$, or (2) reduction with LiAlH$_4$ (Abraham et al., *J. Chem. Soc. Perkin Trans.* 2, 1993, 1047-1059), or (3) reduction with LiAlH$_4$, tosylation, and reduction with LiAlH$_4$. Abraham et al. found that a chlorophyll analogue underwent deoxygenation upon treatment with LiAlH$_4$. A wide variety of other methods are known for deoxygenation of ketones.

Scheme A

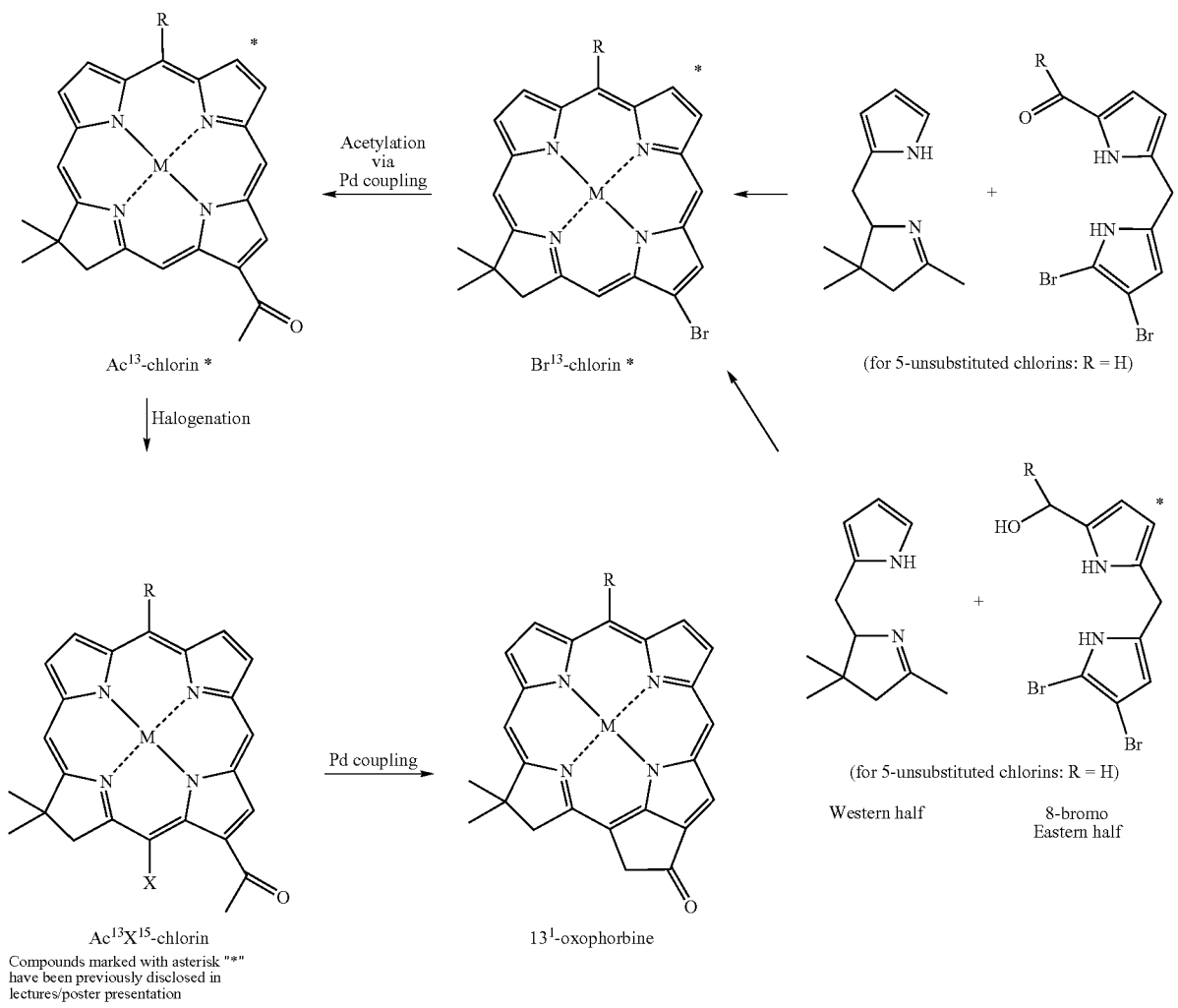

Compounds marked with asterisk "*" have been previously disclosed in lectures/poster presentation E. Metalation, Linking Groups, and Further Substitutions.

Porphyrinic compounds as described above may be metalated with any suitable metal in accordance with known techniques. See, e.g., U.S. Pat. No. 6,208,553. Suitable metals include but are not limited to Pd(II), Pt(II), Mg(II), Zn(II), Al(III), Ga(III), In(III), Sn(IV), Cu(II) (less preferred), Ni(II), and Au(III). Where the metal is trivalent or tetravalent a counterion is included as necessary in accordance with known techniques.

Linking groups for conjugates. Linking groups are included in compounds of the invention to provide a reactive site for conjugation so that the compounds may be coupled to or conjugated to other groups such as proteins, peptides, targeting agents such as antibodies, polymers, particles such as nanoparticles, organic, polymeric or inorganic beads, other solid support surfaces, etc., to form additional active compounds of the invention. In general each group is attached to a linking group including a linker which can be aryl, alkyl, heteroaryl, heteroalkyl (e.g., oligoethylene glycol), peptide, polysaccharide, etc. The linking group may be simply a reactive attachment group or moiety (e.g., —R' where R' is a reactive group such as bromo), or may comprise a combination of an intervening group coupled to a reactive group (e.g., —R"R', where R' is a reactive group and R" is an intervening group such as a hydrophilic group).

For bioconjugation purposes, the choice of water-solubilizing group(s) and conjugation groups is made so as to achieve orthogonal coupling. For example, if a carboxylic acid is used for water solubility, an aldehyde might be used for bioconjugation (via reductive amination with an amino-substituted biomolecule). If a carboxylic acid is used for bioconjugation (via carbodiimide-activation and coupling with an amino-substituted biomolecule), then a complementary group can be used for water solubility (e.g., sulfonic acid, guanidinium, pyridinium). Bioconjugatable groups include amines (including amine derivatives) such as isocyanates, isothiocyanates, iodoacetamides, azides, diazonium salts, etc., acids or acid derivatives such as N-hydroxysuccinimide esters (more generally, active esters derived from carboxylic acids; e.g., p-nitrophenyl ester), acid hydrazides, etc., and other linking groups such as aldehydes, sulfonyl chlorides, sulfonyl hydrazides, epoxides, hydroxyl groups, thiol groups, maleimides, aziridines, acryloyls, halo groups, biotin, 2-Iminobiotin, etc. Linking groups such as the foregoing are known and described in U.S. Pat. Nos. 6,728,129; 6,657,884; 6,212, 093; and 6,208,553.

Conjugates. Other groups can be attached to the active compounds to form a conjugate by means of a linking group to tune or adjust the solubility properties of the active compounds, including hydrophobic groups, hydrophilic groups, polar groups, or amphipathic groups. The polar groups include carboxylic acid, sulfonic acid, guanidinium, carbohydrate, hydroxy, amino acid, pyridinium, imidazolium, etc. Such groups can be attached to substituents that are linear or branched alkyl (e.g., swallowtail), aryl, heteroaryl, heteroalkyl (e.g., oligoethylene glycol), peptide, polysaccharide, etc. Targeting groups such as antibodies, proteins, peptides, and nucleic acids may be attached by means of the linking group. Particles such as nanoparticles, glass beads, etc. may be attached by means of the linking group. Where such additional compounds are attached to form a conjugate that may be attached directly to the active compound or attached by means of an intervening group such as a hydrophilic group, depending upon the particular linking group employed (as noted above).

Hydrophilic groups. Compounds of the present invention may include hydrophilic groups coupled at the linking sites noted above, e.g., covalently coupled thereto, to facilitate delivery thereof, or improve stability, in accordance with known techniques (e.g., to the N-terminus of the peptide). Suitable hydrophilic groups are typically polyols or polyalkylene oxide groups, including straight and branched-chain polyols, with particularly examples including but not limited to poly(propylene glycol), polyethylene-polypropylene glycol or poly(ethylene glycol). The hydrophilic groups may have a number average molecular weight of 20,000 to 40,000 or 60,000. Suitable hydrophilic groups and the manner of coupling thereof are known and described in, for example, U.S. Pat. Nos. 4,179,337; 5,681,811; 6,524,570; 6,656,906; 6,716,811; and 6,720,306. For example, compounds can be pegylated using a single 40,000 molecular weight polyethylene glycol moiety that is attached to the compound by means of a linking group.

Surface attachment groups. As noted above, compounds of the invention can be substituted with a surface attachment group, which may be in protected or unprotected form. A surface attachment group may be a reactive group coupled directly to the active compound, or coupled to the active compound by means of an intervening linker. Linkers L can be aryl, alkyl, heteroaryl, heteroalkyl (e.g., oligoethylene glycol), peptide, polysaccharide, etc. Examples of surface attachment groups (with the reactive site or group in unprotected form) include but are not limited to alkene, alkyne, alcohol, thiol, selenyl, phosphono, telluryl, cyano, amino, formyl, halo, boryl, and carboxylic acid surface attachment groups such as:

4-carboxyphenyl, carboxymethyl, 2-carboxyethyl, 3-carboxypropyl, 2-(4-carboxyphenyl)ethynyl, 4-(2-(4-carboxyphenyl)ethynyl)phenyl, 4-carboxymethylphenyl, 4-(3-carboxypropyl)phenyl, 4-(2-(4-carboxymethylphenyl)ethynyl) phenyl; 4-hydroxyphenyl, hydroxymethyl, 2-hydroxyethyl, 3-hydroxypropyl, 2-(4-hydroxyphenyl)ethynyl, 4-(2-(4-hydroxyphenyl)ethynyl)phenyl, 4-hydroxymethylphenyl, 4-(2-hydroxyethyl)phenyl, 4-(3-hydroxypropyl)phenyl, 4-(2-(4-hydroxymethylphenyl)ethynyl)phenyl; 4-mercaptophenyl, mercaptomethyl, 2-mercaptoethyl, 3-mercaptopropyl, 2-(4-mercaptophenyl)ethynyl, 4-(2-(4-mercaptophenyl)ethynyl) phenyl, 4-mercaptomethylphenyl, 4-(2-mercaptoethyl)phenyl, 4-(3-mercaptopropyl)phenyl, 4-(2-(4-mercaptomethylphenyl)ethynyl)phenyl; 4-selenylphenyl, selenylmethyl, 2-selenylethyl, 3-selenylpropyl, 2-(4-selenylphenyl)ethynyl, 4-selenylmethylphenyl, 4-(2-selenylethyl)phenyl, 4-(3-selenylpropyl)phenyl, 4-selenylmethylphenyl, 4-(2-(4-selenylphenyl)ethynyl)phenyl; 4-tellurylphenyl, tellurylmethyl,2-tellurylethyl,3-tellurylpropyl, 2-(4-tellurylphenyl)ethynyl, 4-(2-(4-tellurylphenyl) ethynyl)phenyl, 4-tellurylmethylphenyl, 4-(2-tellurylethyl) phenyl, 4-(3-tellurylpropyl)phenyl, 4-(2-(4-tellurylmethylphenyl)ethynyl)phenyl;

4-(dihydroxyphosphoryl)phenyl, (dihydroxyphosphoryl) methyl,2-(dihydroxyphosphoryl)ethyl, 3-(dihydroxyphosphoryl)propyl, 2-[4-(dihydroxyphosphoryl)phenyl]ethynyl, 4-[2-[4-(dihydroxyphosphoryl)phenyl]ethynyl]phenyl, 4-[(dihydroxyphosphoryl)methyl]phenyl, 4-[2-(dihydroxyphosphoryl)ethyl]phenyl, 4-[2-[4-(dihydroxyphosphoryl) methylphenyl]ethynyl]phenyl; 4-(hydroxy(mercapto)phosphoryl)phenyl, (hydroxy(mercapto)phosphoryl)methyl, 2-(hydroxy(mercapto)phosphoryl)ethyl, 3-(hydroxy(mercapto)phosphoryl)propyl, 2-[4-(hydroxy(mercapto)phosphoryl)phenyl]ethynyl, 4-[2-[4-(hydroxy(mercapto)phosphoryl)phenyl]ethynyl]phenyl, 4-[(hydroxy(mercapto) phosphoryl)methyl]phenyl, 4-[2-(hydroxy(mercapto) phosphoryl)ethyl]phenyl, 4-[2-[4-(hydroxy(mercapto) phosphoryl)methylphenyl]ethynyl]phenyl;

4-cyanophenyl, cyanomethyl, 2-cyanoethyl, 3-cyanopropyl, 2-(4-cyanophenyl)ethynyl, 4-[2-(4-cyanophenyl)ethynyl]phenyl, 4-(cyanomethyl)phenyl, 4-(2-cyanoethyl)phenyl, 4-[2-[4-(cyanomethyl)phenyl]ethynyl]phenyl;

4-cyanobiphenyl; 4-aminophenyl, aminomethyl, 2-aminoethyl, 3-aminopropyl, 2-(4-aminophenyl)ethynyl, 4-[2-(4-aminophenyl)ethynyl]phenyl, 4-aminobiphenyl;

4-formylphenyl, 4-bromophenyl, 4-iodophenyl, 4-vinylphenyl, 4-ethynylphenyl, 4-allylphenyl, 4-[2-(trimethylsilyl)ethynyl]phenyl, 4-[2-(triisopropylsilyl)ethynyl]phenyl,4-(4,4,5,5-tetramethyl-1,3,2-dioxaborolan-2-yl)phenyl;

formyl, bromo, iodo, bromomethyl, chloromethyl, ethynyl, vinyl, allyl; 4-(ethynyl)biphen-4'-yl, 4-[2-(triisopropylsilyl)ethynyl]biphen-4'-yl, 3,5-diethynylphenyl;

4-(bromomethyl)phenyl, and 2-bromoethyl.

In addition to the monodentate linker-surface attachment groups described above, multidentate linkers can be employed [Nikitin, K. *Chem. Commun.* 2003, 282-283; Hu, J.; Mattern, D. L. *J. Org. Chem.* 2000, 65, 2277-2281; Yao, Y.; Tour, J. M. *J. Org. Chem.* 1999, 64, 1968-1971; Fox, M. A. et al. *Langmuir*, 1998, 14, 816-820; Galoppini, E.; Guo, W. *J. Am. Chem. Soc.* 2001, 123, 4342-4343; Deng, X. et al. *J. Org. Chem.* 2002, 67, 5279-5283; Hector Jr., L. G. et al. *Surface Science*, 2001, 494, 1-20; Whitesell, J. K.; Chang, H. K. *Science*, 1993, 261, 73-76; Galoppini, E. et al. *J. Am. Chem. Soc.* 2002, 67, 7801-7811; Siiman, O. et al. *Bioconjugate Chem.* 2000, 11, 549-556]. Tripodal linkers bearing thiol, carboxylic acid, alcohol, or phosphonic acid units are particularly attractive for firmly anchoring a molecular device on a planar surface. Specific examples of such linkers are built around the triphenylmethane or tetraphenylmethane unit, including the following:

1,1,1-tris[4-(S-acetylthiomethyl)phenyl]methyl,
4-{1,1,1-tris[4-(S-acetylthiomethyl)phenyl]methyl}phenyl,
1,1,1-tris[4-(dihydroxyphosphoryl)phenyl]methyl,
4-{1,1,1-tris[4-(dihydroxyphosphoryl)phenyl] methyl}phenyl,
1,1,1-tris[4-dihydroxyphosphorylmethyl)phenyl]methyl, and
4-{1,1,1-tris[4-(dihydroxyphosphorylmethyl)phenyl] methyl}phenyl;

All as described in Balakumar, Muthukumaran and Lindsey, U.S. patent application Ser. No. 10/867,512 (filed Jun. 14, 2004). See also Lindsey, Loewe, Muthukumaran, and Ambroise, US Patent Application Publication No.

20050096465 (Published May 5, 2005), particularly paragraph 51 thereof. Additional examples of multidentate linkers include but are not limited to:

Alkene surface attachment groups (2, 3, 4 carbons) such as:
3-vinylpenta-1,4-dien-3-yl,
4-(3-vinylpenta-1,4-dien-3-yl)phenyl,
4-(3-vinylpenta-1,4-dien-3-yl)biphen-4'-yl,
4-allylhepta-1,6-dien-4-yl,
4-(4-allylhepta-1,6-dien-4-yl)phenyl,
4-(4-allylhepta-1,6-dien-4-yl)biphen-4'-yl,
5-(1-buten-4-yl)nona-1,8-dien-5-yl,
4-[5-(1-buten-4-yl)nona-1,8-dien-5-yl]phenyl,
4-[5-(1-buten-4-yl)nona-1,8-dien-5-yl]biphen-4'-yl, etc.

Alkyne surface attachment groups (2, 3, 4 carbons) such as:
3-ethynylpenta-1,4-diyn-3-yl,
4-(3-ethynylpenta-1,4-diyn-3-yl)phenyl,
4-(3-ethynylpenta-1,4-diyn-3-yl)biphen-4'-yl,
4-propargylhepta-1,6-diyn-4-yl,
4-(4-propargylhepta-1,6-diyn-4-yl)phenyl,
4-(4-propargylhepta-1,6-diyn-4-yl)biphen-4'-yl,
5-(1-butyn-4-yl)nona-1,8-diyn-5-yl,
4-[5-(1-butyn-4-yl)nona-1,8-diyn-5-yl]phenyl,
4-[5-(1-butyn-4-yl)nona-1,8-diyn-5-yl]biphen-4'-yl, Alcohol surface attachment groups (1, 2, 3 carbons), such as:
2-(hydroxymethyl)-1,3-dihydroxyprop-2-yl,
4-[2-(hydroxymethyl)-1,3-dihydroxyprop-2-yl]phenyl,
4-[2-(hydroxymethyl)-1,3-dihydroxyprop-2-yl]biphen-4'-yl,
3-(2-hydroxyethyl)-1,5-dihydroxypent-3-yl,
4-[3-(2-hydroxyethyl)-1,5-dihydroxypent-3-yl]phenyl,
4-[3-(2-hydroxyethyl)-1,5-dihydroxypent-3-yl]biphen-4'-yl,
4-(3-hydroxypropyl)-1,7-dihydroxyhept-4-yl,
4-[4-(3-hydroxypropyl)-1,7-dihydroxyhept-4-yl]phenyl,
4-[4-(3-hydroxypropyl)-1,7-dihydroxyhept-4-yl]biphen-4'-yl, etc., Thiol surface attachment groups (1, 2, 3 carbons) such as:
2-(mercaptomethyl)-1,3-dimercaptoprop-2-yl,
4-[2-(mercaptomethyl)-1,3-dimercaptoprop-2-yl]phenyl,
4-[2-(mercaptomethyl)-1,3-dimercaptoprop-2-yl]biphen-4'-yl,
3-(2-mercaptoethyl)-1,5-dimercaptopent-3-yl
4-[3-(2-mercaptoethyl)-1,5-dimercaptopent-3-yl]phenyl,
4-[3-(2-mercaptoethyl)-1,5-dimercaptopent-3-yl]biphen-4'-yl,
4-(3-mercaptopropyl)-1,7-dimercaptohept-4-yl,
4-[4-(3-mercaptopropyl)-1,7-dimercaptohept-4-yl]phenyl,
4-[4-(3-mercaptopropyl)-1,7-dimercaptohept-4-yl]biphen-4'-yl etc., Selenyl surface attachment groups (1, 2, 3 carbons), such as:
2-(selenylmethyl)-1,3-diselenylprop-2-yl,
4-[2-(selenylmethyl)-1,3-diselenylprop-2-yl]phenyl,
4-[2-(mercaptomethyl)-1,3-dimercaptoprop-2-yl]biphen-4'-yl,
3-(2-selenylethyl)-1,5-diselenylpent-3-yl,
4-[3-(2-selenylethyl)-1,5-diselenylpent-3-yl]phenyl,
4-[3-(2-selenylethyl)-1,5-diselenylpent-3-yl]biphen-4'-yl,
4-(3-selenylpropyl)-1,7-diselenylhept-4-yl,
4-[4-(3-selenylpropyl)-1,7-diselenylhept-4-yl]phenyl,
4-[4-(3-selenylpropyl)-1,7-diselenylhept-4-yl]biphen-4'-yl, etc.

Phosphono surface attachment groups (1, 2, 3 carbons), such as:
2-(phosphonomethyl)-1,3-diphosphonoprop-2-yl,
4-[2-(phosphonomethyl)-1,3-diphosphonoprop-2-yl]phenyl,
4-[2-(phosphonomethyl)-1,3-diphosphonoprop-2-yl]biphen-4'-yl,
3-(2-phosphonoethyl)-1,5-diphosphonopent-3-yl,
4-[3-(2-phosphonoethyl)-1,5-diphosphonopent-3-yl]phenyl,
4-[3-(2-phosphonoethyl)-1,5-diphosphonopent-3-yl]biphen-4'-yl,
4-(3-phosphonopropyl)-1,7-diphosphonohept-4-yl,
4-[4-(3-phosphonopropyl)-1,7-diphosphonohept-4-yl]phenyl,
4-[4-(3-phosphonopropyl)-1,7-diphosphonohept-4-yl]biphen-4'-yl, etc., and Carboxylic acid surface attachment groups (1, 2, 3 carbons), such as:
2-(carboxymethyl)-1,3-dicarboxyprop-2-yl,
4-[2-(carboxymethyl)-1,3-dicarboxyprop-2-yl]phenyl,
4-[2-(carboxymethyl)-1,3-dicarboxyprop-2-yl]biphen-4'-yl,
3-(2-carboxyethyl)-1,5-dicarboxypent-3-yl,
4-[3-(2-carboxyethyl)-1,5-dicarboxypent-3-yl]phenyl,
4-[3-(2-carboxyethyl)-1,5-dicarboxypent-3-yl]biphen-4'-yl,
4-(3-carboxypropyl)-1,7-dicarboxyhept-4-yl,
4-[4-(3-carboxypropyl)-1,7-dicarboxyhept-4-yl]phenyl,
4-[4-(3-carboxypropyl)-1,7-dicarboxyhept-4-yl]biphen-4'-yl, etc.

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

Active compounds of the invention can be provided as pharmaceutically acceptable salts. Such salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids.

Ligands. In another embodiment, the disclosed compounds may be targeted to specific target tissues or target compositions using ligands specific for the target tissue or target composition, for example, using ligands or ligand-receptor pairs such as antibodies and antigens. Antibodies against tumor antigens and against pathogens are known. For example, antibodies and antibody fragments which specifically bind markers produced by or associated with tumors or infectious lesions, including viral, bacterial, fungal and parasitic infections, and antigens and products associated with such microorganisms have been disclosed, inter alia, in Hansen et al., U.S. Pat. No. 3,927,193 and Goldenberg, U.S. Pat. Nos. 4,331,647; 4,348,376; 4,361,544; 4,468,457; 4,444, 744; 4,818,709 and 4,624,846. Antibodies against an antigen, e.g., a gastrointestinal, lung, breast, prostate, ovarian, testicular, brain or lymphatic tumor, a sarcoma or a melanoma, can be used.

A wide variety of monoclonal antibodies against infectious disease agents have been developed, and are summarized in a review by Polin, in Eur. J. Clin. Microbiol., 3(5): 387-398 (1984), showing ready availability. These include monoclonal antibodies (MAbs) against pathogens and their antigens such as the following: Anti-bacterial Mabs such as those against *Streptococcus agalactiae, Legionella pneumophilia, Streptococcus pyogenes, Esherichia coli, Neisseria gonorrhosae, Neisseria meningitidis,* Pneumococcus, *Hemophilis influenzae B, Treponema pallidum,* Lyme disease, spirochetes, *Pseudomonas aeruginosa, Mycobacterium leprae, Brucella abortus, Mycobacterium tuberculosis,* Tetanus toxin, Anti-protozoan Mabs such as those against *Plasmodium falciparum, Plasmodium vivax, Toxoplasma gondii, Trypanosoma rangeli, Trypanosoma cruzi, Trypanosoma rhodesiensei, Trypanosoma brucei, Schistosoma mansoni, Schistosoma japanicum, Mesocestoides corti, Emeria tenella, Onchocerca volvulus, Leishmania tropica, Trichinella spiralis, Theileria parva, Taenia hydatigena, Taenia ovis, Taenia saginata,* Anti-viral MAbs such as those against HIV-1, -2, and -3, Hepatitis A, B, C, D, Rabies virus, Influenza virus, Cytomegalovirus, Herpes simplex I and II, Human serum parvo-like virus, Respiratory syncytial virus, Varicella-Zoster virus, Hepatitis B virus, Measles virus, Adenovirus, Human T-cell leukemia viruses, Epstein-Barr virus, Mumps virus, Sindbis virus, Mouse mammary tumor virus, Feline leukemia virus, Lymphocytic choriomeningitis virus, Wart virus, Blue tongue virus, Sendai virus, Reo virus, Polio virus, Dengue virus, Rubella virus, Murine leukemia virus, Antimycoplasmal MAbs such as those against *Acholeplasma laidlawii, Mycoplasma arthritidis, M. hyorhinis, M. orale, M. arginini, M. pneumonia*; etc.

Suitable MAbs have been developed against most of the micro-organisms (bacteria, viruses, protozoa, other parasites) responsible for the majority of infections in humans, and many have been used previously for in vitro diagnostic purposes. These antibodies, and newer MAbs that can be generated by conventional methods, are appropriate for use as target agents with the compounds provided herein.

MAbs against malaria parasites can be directed against the sporozoite, merozoite, schizont and gametocyte stages. Monoclonal antibodies have been generated against sporozoites (circumsporozoite antigen), and have been shown to neutralize sporozoites in vitro and in rodents (N. Yoshida et al., Science 207: 71-73 (1980)). Monoclonal antibodies to *T. gondii,* the protozoan parasite involved in toxoplasmosis have been developed (Kasper et al., J. Immunol. 129: 1694-1699 (1982). MAbs have been developed against schistosomular surface antigens and have been found to act against schistosomulae in vivo or in vitro (Simpson et al., Parasitology 83: 163-177 (1981); Smith et al., Parasitology 84: 83-91 (1982); Gryzch et al., J. Immunol. 129: 2739-2743 (1982); Zodda et al., J. Immunol. 129: 2326-2328 (1982); Dissous et al., J. Immunol. 129: 2232-2234 (1982).

It should be noted that mixtures of antibodies and immunoglobulin classes can be used, as can hybrid antibodies. Multispecific, including bispecific and hybrid, antibodies and antibody fragments are especially preferred in the methods of the present invention for detecting and treating target tissue and are comprised of at least two different substantially monospecific antibodies or antibody fragments, wherein at least two of said antibodies or antibody fragments specifically bind to at least two different antigens produced or associated with the targeted lesion or at least two different epitopes or molecules of a marker substance produced or associated with the target tissue. Multispecific antibodies and antibody fragments with dual specificities can be prepared analogously to the anti-tumor marker hybrids disclosed in U.S. Pat. No. 4,361,544. Other techniques for preparing hybrid antibodies are disclosed in, e.g., U.S. Pat. Nos. 4,474,893 and 4,479,895, and in Milstein et al., Immunol. Today 5: 299 (1984).

Antibody fragments useful in the present invention include $F(ab')_2$, $F(ab)_2$, Fab', Fab, Fv and the like including hybrid fragments. Preferred fragments are Fab', $F(ab')_2$, Fab, and $F(ab)_2$. Also useful are any subfragments retaining the hypervariable, antigen-binding region of an immunoglobulin and having a size similar to or smaller than a Fab' fragment. This will include genetically engineered and/or recombinant proteins, whether single-chain or multiple-chain, which incorporate an antigen-binding site and otherwise function in vivo as targeting vehicles in substantially the same way as natural immunoglobulin fragments. Such single-chain binding molecules are disclosed in U.S. Pat. No. 4,946,778, which is hereby incorporated by reference. Fab' antibody fragments may be conveniently made by reductive cleavage of $F(ab')_2$ fragments, which themselves may be made by pepsin digestion of intact immunoglobulin. Fab antibody fragments may be made by papain digestion of intact immunoglobulin, under reducing conditions, or by cleavage of $F(ab)_2$ fragments which result from careful papain digestion of whole immunoglobulin.

A ligand or one member of a ligand-receptor binding pair can be conjugated to the compounds provided herein for targeting the compounds to specific target tissues or target compositions. Examples of ligand-receptor binding pairs are set out in U.S. Pat. Nos. 4,374,925 and 3,817,837, the teachings of which are incorporated herein by reference.

Conjugation to ligands. Many compounds that can serve as targets for ligand-receptor binding pairs, and more specifically, antibodies, have been identified, and the techniques to construct conjugates of such ligands with photosensitizers are well known to those of ordinary skill in this art. For example, Rakestraw et al. teaches conjugating Sn(IV) chlorin e via covalent bonds to monoclonal antibodies using a modified dextran carrier (Rakestraw, S. L., Tompkins, R. D., and Yarmush, M. L., Proc. Nad. Acad. Sci. USA 87: 4217-4221 (1990). The compounds disclosed herein can also be conjugated to a ligand, such as an antibody, by using a coupling agent. Any bond which is capable of linking the components such that they are stable under physiological conditions for the time needed for administration and treatment is suitable, but covalent linkages are preferred. The link between two components may be direct, e.g., where a photosensitizer is linked directly to a targeting agent, or indirect, e.g., where a photosensitizer is linked to an intermediate and that intermediate being linked to the targeting agent.

A coupling agent should function under conditions of temperature, pH, salt, solvent system, and other reactants that substantially retain the chemical stability of the photosensitizer, the backbone (if present), and the targeting agent. Coupling agents should link component moieties stably, but such that there is only minimal or no denaturation or deactivation of the photosensitizer or the targeting agent. Many coupling agents react with an amine and a carboxylate, to form an amide, or an alcohol and a carboxylate to form an ester. Coupling agents are known in the art (see, e.g., M. Bodansky, "Principles of Peptide Synthesis", 2nd ed., and T. Greene and P. Wuts, "Protective Groups in Organic Synthesis," 2nd Ed, 1991, John Wiley, NY).

The conjugates of the compounds provided herein with ligands such as antibodies can be prepared by coupling the compound to targeting moieties by cleaving the ester on the "d" ring and coupling the compound via peptide linkages to the antibody through an N terminus, or by other methods known in the art. A variety of coupling agents, including cross-linking agents, can be used for covalent conjugation. Examples of cross-linking agents include N,N'-dicyclohexylcarbodiimide (DCC), N-succinimidyl-5-acetyl-thioacetate (SATA), N-succinimidyl-3-(2-pyridyldithio) propionate (SPDP), ortho-phenylene-dimaleimide (o-PDM), and sulfo-succinimidyl 4-(N-maleimido-methyl)-cyclohexane-1-carboxylate (sulfo-SMCC). See, e.g., Karpovsky et al. J. Exp. Med. 160:1686 (1984); and Liu, M A et al., Proc. Natl. Acad. Sci. USA 82: 8648 (1985). Other methods include those described by Brennan et al. Science 229: 81-83 (1985) and Glennie et al., J. Immunol. 139: 2367-2375 (1987). A large number of coupling agents for peptides and proteins, along with buffers, solvents, and methods of use, are described in the Pierce Chemical Co. catalog, pages 0-90 to 0-110 (1995, Pierce Chemical Co., 3747 N. Meridian Rd., Rockford Ill., 61105, U.S.A.), which catalog is hereby incorporated by reference.

For example, DCC is a useful coupling agent that can be used to promote coupling of the alcohol NHS to chlorin $e_6$ in DMSO forming an activated ester which can be cross-linked to polylysine. DCC is a carboxy-reactive cross-linker commonly used as a coupling agent in peptide synthesis, and has a molecular weight of 206.32. Another useful cross-linking agent is SPDP, a heterobifunctional cross-linker for use with primary amines and sulfhydryl groups. SPDP has a molecular weight of 312.4, a spacer arm length of 6.8 angstroms, is reactive to NHS-esters and pyridyldithio groups, and produces cleavable cross-linking such that, upon further reaction, the agent is eliminated so the photosensitizer can be linked directly to a backbone or targeting agent. Other useful conjugating agents are SATA for introduction of blocked SH groups for two-step cross-linking, which is deblocked with hydroxylamine-HCl, and sulfo-SMCC, reactive towards amines and sulfhydryls. Other cross-linking and coupling agents are also available from Pierce Chemical Co. Additional compounds and processes, particularly those involving a Schiff base as an intermediate, for conjugation of proteins to other proteins or to other compositions, for example to reporter groups or to chelators for metal ion labeling of a protein, are disclosed in EPO 243,929 A2 (published Nov. 4, 1987).

Photosensitizers which contain carboxyl groups can be joined to lysine ϵ-amino groups in the target polypeptides either by preformed reactive esters (such as N-hydroxy succinimide ester) or esters conjugated in situ by a carbodiimide-mediated reaction. The same applies to photosensitizers which contain sulfonic acid groups, which can be transformed to sulfonyl chlorides which react with amino groups. Photosensitizers which have carboxyl groups can be joined to amino groups on the polypeptide by an in situ carbodiimide method. Photosensitizers can also be attached to hydroxyl groups, of serine or threonine residues or to sulfhydryl groups of cysteine residues.

Methods of joining components of a conjugate, e.g., coupling polyamino acid chains bearing photosensitizers to antibacterial polypeptides, can use heterobifunctional cross linking reagents. These agents bind a functional group in one chain and to a different functional group in the second chain. These functional groups typically are amino, carboxyl, sulfhydryl, and aldehyde. There are many permutations of appropriate moieties which will react with these groups and with differently formulated structures, to conjugate them together. See the Pierce Catalog, and Merrifield, R. D. et al., Ciba Found Symp. 186: 5-20 (1994).

The compounds or pharmaceutically acceptable derivatives thereof may be packaged as articles of manufacture containing packaging material, a compound or pharmaceutically acceptable derivative thereof provided herein, which is effective for modulating the activity of hyperproliferating tissue or neovascularization, or for treatment, prevention or amelioration of one or more symptoms of hyperproliferating tissue or neovascularization mediated diseases or disorders, or diseases or disorders in which hyperproliferating tissue or neovascularization activity, is implicated, within the packaging material, and a label that indicates that the compound or composition, or pharmaceutically acceptable derivative thereof, is used for modulating the activity of hyperproliferating tissue or neovascularization, or for treatment, prevention or amelioration of one or more symptoms of hyperproliferating tissue or neovascularization mediated diseases or disorders, or diseases or disorders in which hyperproliferating tissue or neovascularization is implicated.

Stability. An advantage of some embodiments of compounds of the present invention is their stability and absorption characteristics. Thus, the present invention provides a "neat" composition consisting of an active compound of the invention (e.g., compounds of Formula DI, or the pharmaceutically acceptable salts, prodrugs, or conjugates thereof (e.g. with a targeting agent such as a protein, peptide or antibody)), wherein the composition has or is characterized by a peak Molar absorption coefficient in solution of at least 10,000, up to 300,000 $M^{-1}cm^{-1}$ or more, at a wavelength between 600 or 650 up to 850 or 900 nanometers (it being understood that (a) the active compound must be placed into solution to determine its peak Molar absorption coefficient at the indicated wavelength; and (b) the compound may exhibit additional peaks outside of this range, or multiple peaks within this range).

In addition, the present invention provides compositions comprising or consisting essentially of an active compound of the invention (e.g. compounds of Formula I, or the pharmaceutically acceptable salts, prodrugs, or conjugates thereof (e.g. with a targeting agent such as a protein, peptide or antibody)) in a solvent. The amount of solvent is not critical and may comprise from 0.01 or 1 to 99 or 99.99 percent by weight of the composition. The composition has or is characterized by a peak Molar absorption coefficient in solution of at least 10,000, up to 300,000 $M^{-1}cm^{-1}$ or more, at a wavelength between 600 or 650 up to 850 or 900 nanometers. It will be appreciated that agitation may be required to break agglomerated particles back into solution prior to determining molar absorption, but that some level of agglomeration may actually be desired for practical use of the composition. Suitable solvents depend upon the particular compound and intended use for that compound, but include both organic solvents, aqueous solvents and combinations thereof.

The compositions, be they the compounds in "neat" form or the compounds mixed with a solvent, have or exhibit a loss of not more than 10, 15 or 20 percent by weight of the compound of the invention (due to degradation thereof) when stored in a sealed vessel (e.g., a flask ampoule or vial), at room temperature in the absence of ambient light for at least 3 or 4 months. Degradation can be determined by spectroscopy, thin-layer chromatography, NMR spectroscopy, and/or mass spectrometry, in accordance with known techniques.

Solubility. An advantage of some embodiments of compounds of the invention is their solubility. Thus the present invention provides compositions, including but not limited to pharmaceutical formulations, comprising, consisting of or consisting essentially of: (a) an aqueous solvent (for example, distilled water, saline solution, buffer solution); and (b) from 1, 2, 5 or 10 microMolar up to 200, 300, or 500 milliMolar of an active compound as described herein solubilized in the aqueous solvent.

2. Pharmaceutical Formulations.

Formulation of Pharmaceutical Compositions. The pharmaceutical compositions provided herein contain therapeutically effective amounts of one or more of the compounds provided herein that are useful in the prevention, treatment, or amelioration of one or more of the symptoms of diseases or disorders associated with hyperproliferating tissue or neovascularization, or in which hyperproliferating tissue or neovascularization is implicated, in a pharmaceutically acceptable carrier. Diseases or disorders associated with hyperproliferating tissue or neovascularization include, but are not limited to, cancer, psoriasis, atherosclerosis, heart disease, and age-related macular degeneration. Pharmaceutical carriers suitable for administration of the compounds provided herein include any such carriers known to those skilled in the art to be suitable for the particular mode of administration.

Pharmaceutical compositions preferably exhibit the absorption characteristics and storage or stability characteristics described above.

In addition, the compounds may be formulated as the sole pharmaceutically active ingredient in the composition or may be combined with other active ingredients.

The compositions contain one or more compounds provided herein. The compounds are, in one embodiment, formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. In one embodiment, the compounds described above are formulated into pharmaceutical compositions using techniques and procedures well known in the art (see, e.g., Arisel, Introduction to Pharmaceutical Dosage Forms, Fourth Edition 1985, 126).

In the compositions, effective concentrations of one or more compounds or pharmaceutically acceptable derivatives thereof is (are) mixed with a suitable pharmaceutical carrier. The compounds may be derivatized as the corresponding salts, esters, enol ethers or esters, acetals, ketals, orthoesters, hemiacetals, hemiketals, acids, bases, solvates, hydrates or prodrugs prior to formulation, as described above. The concentrations of the compounds in the compositions are effective for delivery of an amount, upon administration, that treats, prevents, or ameliorates one or more of the symptoms of diseases or disorders associated with hyperproliferating tissue or neovascularization or in which hyperproliferating tissue or neovascularization is implicated.

In one embodiment, the compositions are formulated for single dosage administration. To formulate a composition, the weight fraction of compound is dissolved, suspended, dispersed or otherwise mixed in a selected carrier at an effective concentration such that the treated condition is relieved, prevented, or one or more symptoms are ameliorated.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and in U.S. Pat. No. 5,952,366 to Pandey et al. (1999) and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of diseases or disorders associated with hyperproliferating tissue or neovascularization or in which hyperproliferating tissue or neovascularization is implicated, as described herein.

In one embodiment, a therapeutically effective dosage should produce a serum concentration of active ingredient of from about 0.1 ng/ml to about 50-100 ug/ml. In one embodiment, a therapeutically effective dosage is from 0.001, 0.01 or 0.1 to 10, 100 or 1000 mg of active compound per kilogram of body weight per day. Pharmaceutical dosage unit forms are prepared to provide from about 0.01 mg, 0.1 mg or 1 mg to about 500 mg, 1000 mg or 2000 mg, and in one embodiment from about 10 mg to about 500 mg of the active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN™, or dissolution in aqueous sodium bicarbonate. Derivatives of the compounds, such as prodrugs of the compounds may also be used in formulating effective pharmaceutical compositions.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are, in one embodiment, formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents.

Actual methods of preparing such dosage forms are known, or will be apparent, to those skilled in this art; for example, see Remington's Pharmaceutical Sciences, Mack Publishing Company, Easton, Pa., 15th Edition, 1975.

Dosage forms or compositions containing active ingredient in the range of 0.005% to 100% with the balance made up from non-toxic carrier may be prepared. Methods for preparation of these compositions are known to those skilled in the art. The contemplated compositions may contain 0.001%-100% active ingredient, in one embodiment 0.1-95%, in another embodiment 75-85%.

Compositions for Oral Administration. Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

Solid Compositions for Oral Administration. In certain embodiments, the formulations are solid dosage forms, in one embodiment, capsules or tablets. The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an emetic coating; and a film coating. Examples of binders include microcrystalline cellulose, gum tragacanth, glucose solution, acacia mucilage, gelatin solution, molasses, polyinylpyrrolidine, povidone, crospovidones, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, gellan gum, sodium carboxymethylcellulose, polyethylene glycol 4000 and cellulose acetate phthalate.

The compound, or pharmaceutically acceptable derivative thereof, could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient. When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

Liquid Compositions for Oral Administration. Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and welting agents. Pharmaceutically acceptable substances used in effervescent granules, to be reconstituted into a liquid oral dosage form, include organic acids and a source of carbon dioxide. Coloring and flavoring agents are used in all of the above dosage forms. Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, xanthan gum, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation. For a solid dosage form, the solution or suspension, in for example propylene carbonate, vegetable oils or triglycerides, is in one embodiment encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other usefull formulations include those set forth in U.S. Pat. Nos. RE28,819 and 4,358,603. Briefly, such formulations include, but are not limited to, those containing a compound provided herein, a dialkylated mono- or poly-alkylene glycol, including, but not limited to, 1,2-dimethoxymethane, diglyme, triglyrne, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(loweralkyl)acetals of loweralkyl aldehydes such as acetaldehyde diethyl acetal.

3. Injectables, Solutions and Emulsions. Parenteral administration, in one embodiment characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcellulose, xanthan gum, hydroxypropyl methylcellulose and polyvinylpyrrolidone. Emulsifying agents include Polysorbate 80 (TWEEN™ 80). A sequestering or chelating agent of metal ions includes EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In one embodiment, a therapeutically effective dosage is formulated to contain a concentration of at least about 0.1% w/w up to about 90% w/w or more, in certain embodiments more than 1% w/w of the active compound to the treated tissue(s).

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

Lyophilized Powders. Lyophilized powders, which can be reconstituted for administration as solutions, emulsions and other mixtures, can also be used to carry out the present invention. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium-phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

Topical Administration. Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation (see, e.g., U.S. Pat. Nos. 4,044,126; 4,414,209; and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will, in one embodiment, have diameters of less than 50 microns, in one embodiment less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered. These solutions, particularly those intended for ophthalmic use, may be formulated as 0.01%-10% isotonic solutions, pH about 5-7, with appropriate salts.

Compositions for other Routes of Administration. Other routes of administration, such as transdermal patches, including iontophoretic and electrophoretic devices, and rectal administration, are also contemplated herein.

Transdermal patches, including iontophoretic and electrophoretic devices, are well known to those of skill in the art. For example, such patches are disclosed in U.S. Pat. Nos. 6,267,983; 6,261,595; 6,256,533; 6,167,301; 6,024,975; 6,010715; 5,985,317; 5,983,134; 5,948,433 and 5,860,957.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 gm.

Tablets and capsules for rectal administration are manufactured using the same pharmaceutically acceptable substance and by the same methods as for formulations for oral administration.

Targeted Formulations. The compounds provided herein, or pharmaceutically acceptable derivatives thereof, may also be formulated to be targeted to a particular tissue, receptor, infecting agent or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316, 652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542 and 5,709,874.

Liposomes. In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The articles of manufacture provided herein contain packaging materials. Packaging materials for use in packaging pharmaceutical products are well known to those of skill in the art. See, e.g., U.S. Pat. Nos. 5,323,907; 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease or disorder in which hyperproliferating tissue or neovascularization is implicated as a mediator or contributor to the symptoms or cause.

Methods of Use

A. Methods of PDT, Diagnostic and Therapeutic Applications. Briefly, the photosensitizing compound is generally administered to the subject before the target tissue, target composition or subject is subjected to illumination. The photosensitizing compound is administered as described elsewhere herein.

The dose of photosensitizing compound can be determined clinically. Depending on the photosensitizing compound used, an equivalent optimal therapeutic level will have to be established. A certain length of time is allowed to pass for the circulating or locally delivered photosensitizer to be taken up by the target tissue. The unbound photosensitizer is cleared from the circulation during this waiting period, or additional time can optionally be provided for clearing of the unbound compound from non-target tissue. The waiting period will be determined clinically and may vary from compound to compound.

At the conclusion of this waiting period, a laser light source or a non-laser light source (including but not limited to artificial light sources such as fluorescent or incandescent light, or natural light sources such as ambient sunlight) is used to activate the bound drug. The area of illumination is determined by the location and dimension of the pathologic region to be detected, diagnosed or treated. The duration of illumination period will depend on whether detection or treatment is being performed, and can be determined empirically. A total or cumulative period of time anywhere from between about 4 minutes and 72 hours can be used. In one embodiment, the illumination period is between about 60 minutes and 148 hours. In another embodiment, the illumination period is between about 2 hours and 24 hours.

Preferably, the total fluence or energy of the light used for irradiating, as measured in Joules, is between about 10 Joules and about 25,000 Joules; more preferably, between about 100 Joules and about 20,000 Joules; and most preferably, between about 500 Joules and about 10,000 Joules. Light of a wavelength and fluence sufficient to produce the desired effect is selected, whether for detection by fluorescence or for therapeutic treatment to destroy or impair a target tissue or target composition. Light having a wavelength corresponding at least in part with the characteristic light absorption wavelength of the photosensitizing agent is preferably used for irradiating the target issue.

The intensity or power of the light used is measured in watts, with each Joule equal to one watt-sec. Therefore, the intensity of the light used for irradiating in the present invention may be substantially less than 500 mW/cm$^2$. Since the total fluence or amount of energy of the light in Joules is divided by the duration of total exposure time in seconds, the longer the amount of time the target is exposed to the irradiation, the greater the amount of total energy or fluence may be used without increasing the amount of the intensity of the light used. The present invention employs an amount of total fluence of irradiation that is sufficiently high to activate the photosensitizing agent.

In one embodiment of using compounds disclosed herein for photodynamic therapy, the compounds are injected into the mammal, e.g. human, to be diagnosed or treated. The level of injection is usually between about 0.1 and about 0.5 umol/kg of body weight. In the case of treatment, the area to be treated is exposed to light at the desired wavelength and energy, e.g. from about 10 to 200 J/cm$^2$. In the case of detection, fluorescence is determined upon exposure to light at a wavelength sufficient to cause the compound to fluoresce at a wavelength different than that used to illuminate the compound. The energy used in detection is sufficient to cause fluorescence and is usually significantly lower than is required for treatment.

Any one of the photosensitizing compounds disclosed herein or a pharmaceutically acceptable derivative thereof may be supplied in a kit along with instructions on conducting any of the methods disclosed herein. Instructions may be in any tangible form, such as printed paper, a computer disk that instructs a person how to conduct the method, a video cassette containing instructions on how to conduct the method, or computer memory that receives data from a remote location and illustrates or otherwise provides the instructions to a person (such as over the Internet). A person may be instructed in how to use the kit using any of the instructions above or by receiving instructions in a classroom or in the course of treating a patient using any of the methods disclosed herein, for example.

Additional examples and specific examples of methods of using compounds and compositions of the present invention include but are not limited to the following:

(i) Treatment of opportunistic infections. Compounds, compositions and methods of the invention are useful for PDT of opportunistic infections, particularly of soft tissue. For antimicrobial treatment (via PDT) of infections, particularly wound infections, the infecting organism can include (as non limiting examples) *Staphylococcus aureus, Pseudomonas aeruginosa, Escherichia coli*. In nosocomial infections, *P. aeruginosa* is responsible for 8% of surgical-wound infections and 10% of bloodstream infections. In some embodiments the subjects are immunocompromised subjects, such as those afflicted with AIDS or undergoing treatment with immunosupressive agents.

(ii) Treatment of burns. Infections by *S. aureus* and gram-positive bacteria in general are particularly pronounced in burns (Lambrechts, 2005). The multidrug resistance of *S. aureus* presents significant medical challenges. In this regard, compounds, compositions and methods of the invention are useful for the treatment of opportunistic infections of burns.

(iii) Sepsis. Compounds, compositions and methods of the invention are useful for the PDT treatment of subjects afflicted with opportunistic infections of *Vibrio vulnificus*. *V. vulnifcus*, a gram-negative bacterium, causes primary sepsis, wound infections, and gastrointestinal illness in humans.

(iv) Ulcers. Compounds, compositions and methods of the invention are useful for PDT treatment of the bacterium that causes ulcers (*Helicobacter pylori*). In the clinic, treatment can be effected in any suitable manner, such as by insertion of a fiber optic cable (akin to an endoscope but with provisions for delivery of red or near-IR light) into the stomach or afflicted region.

(v) Periodontal disease. Compounds, compositions and methods of the invention are useful in PDT for the treatment of periodontal disease, including gingivitis. Periodontal disease is caused by the overgrowth of bacteria, such as the gram-negative anaerobe *Porphyromonas gingivalis*. As with many PDT treatments, targeting or solubilizing entities in conjunction with the photoactive species are essential for appropriate delivery of the photoactive species to the desired cells. The oral pathogens of interest for targeting include *Porphyromonas gingivalis, Actinobacillus actinomycetemcomitans, Bacteroides forsythus, Campylobacter rectus, Eikenella corrodens, Fusobacterium nucleatum* subsp. *Polymorphum, Actinomyces viscosus*, and the streptococci. For such applications the compounds or compositions of the invention can be topically applied (e.g., as a mouthwash or rinse) and then light administered with an external device, in-the-mouth instrument, or combination thereof.

(vi) Atherosclerosis. Compounds, compositions and methods of the invention are useful in PDT to treat vulnerable atherosclerotic plaque. Without wishing to be bound to any particular theory, invading inflammatory macrophages are believed to secrete metalloproteinases that degrade a thin layer of collagen in the coronary arteries, resulting in thrombosis, which often is lethal. Active compounds targeted to such inflammatory macrophages are useful for PDT of vulnerable plaque.

(vii) Cosmetic and dermatologic applications. Compounds, compositions and methods of the invention are useful in PDT to treat a wide range of cosmetic dermatological problems, such as hair removal, treatment of psoriasis, or removal of skin discoloration. Ruby lasers are currently used for hair removal; in many laser treatments melanin is the photosensitized chromophore. Such treatments work reasonably well for fair-skinned individuals with dark hair. Compounds, compositions and methods of the invention can be used as near-IR sensitizers for hair removal, which enables targeting a chromophore with a more specific and sharp absorption band.

(viii) Acne. Compounds, compositions and methods of the invention are useful in PDT to treat acne. Acne vulgaris is caused by *Propionibacterium acnes*, which infects the sebaceous gland; some 80% of young people are affected. Here again, the growing resistance of bacteria to antibiotic treatment is leading to an upsurge of acne that is difficult to treat. Current PDT treatments of acne typically rely on the addition of aminolevulinic acid, which in the hair follicle or sebaceous gland is converted to free base porphyrins. Compounds and compositions of the invention can be administered to subjects topically or parenterally (e.g., by subcutaneous injection) depending upon the particular condition.

(ix) Infectious diseases. Compounds, compositions and methods of the invention are useful in PDT to treat infectious' diseases. For example, Cutaneous leishmaniasis and sub-cutaneous leishmaniasis, which occurs extensively in the Mediterranean and Mideast regions, is currently treated with arsenic-containing compounds. PDT has been used to reasonable effect recently, at least in one case, on a human patient. The use of compounds and compositions of the present invention are likewise useful, and potentially offer advantages such as ease of synthesis and better spectral absorption properties.

(x) Tissue sealants. Compounds, compositions and methods of the invention are useful in PDT as tissue sealants in subjects in need thereof. Light-activated tissue sealants are attractive for sealing wounds, bonding tissue, and closing defects in tissue There are many applications where sutures or staples are undesirable, and use of such mechanical methods of sealing often lead to infection and scarring.

(xi) Neoplastic disease. Compounds, compositions and methods of the invention are useful in PDT for treating neoplastic diseases or cancers, including skin cancer, lung cancer, colon cancer, breast cancer, prostate cancer, cervical cancer, ovarian cancer, basal cell carcinoma, leukemia, lymphoma, squamous cell carcinoma, melanoma, plaque-stage cutaneous T-cell lymphoma, and Kaposi sarcoma.

B. Imaging Enhancing Agents. In addition to PDT, the compositions provided herein can be used as imaging enhancing agents in diagnostic imaging techniques, or for the labeling of target tissues or target compositions for diagnostic radiology. In the modern medical field, there are a variety of treatments including magnetic resonance imaging (MRI) for the diagnosis of diseases. Detection of cancer in its early stages should improve the ability to cure eliminate the cancerous tissue. Early diagnosis of precancerous regions and minute cancer are important subject matters in modern cancer treatments. MRI has emerged as a powerful tool in clinical settings because it is noninvasive and yields an accurate volume rendering of the subject. The image is created by imposing one or more orthogonal magnetic field gradients upon the subject or specimen while exciting nuclear spins with radio frequency pulses as in a typical nuclear magnetic resonance (NMR) experiment. After collection of data with a variety of gradient fields, deconvolusion yields a one, two, or three dimensional image of the specimen/subject. Typically, the image is based on the NMR signal from the protons of water where the signal intensity in a given volume element is a function of the water concentration and relaxation times. Local variation in there parameters provide the vivid contrast observed in MR images.

MRI contrast agents act by increasing the rate of relaxation, thereby increasing the contrast between water molecules in the region where the imaging agent accretes and water molecules elsewhere in the body. However, the effect of the agent is to decrease both $T_1$ and $T_2$, the former resulting in greater contrast while the latter results in lesser contrast. Accordingly, the phenomenon is concentration-dependent, and there is normally an optimum concentration of a paramagnetic species for maximum efficacy. This optimal concentration will vary with the particular agent used, the locus of imaging, the mode of imaging, i.e., spin-echo, saturation-recovery, inversion-recovery and/or various other strongly $T_1$-dependent or $T_2$-dependent imaging techniques, and the composition of the medium in which the agent is dissolved or suspended. These factors, and their relative importance are known in the art. See, e.g., Pykett, Scientific American 246: 78 (1982); Runge et al., Am. J. Radiol. 141: 1209 (1983). When MRI contrast agents are used diagnostically, they are vascularly perfused, enhancing the contrast of blood vessels and reporting on organ lesions and infiltration. However, the labeling of specific tissues for diagnostic radiology remains a difficult challenge for MRI. Efforts to develop cell and tissue-specific MRI image enhancing agents by modifying existing immunological techniques has been the focus of much research in diagnostic radiology. For example, antibodies labeled with paramagnetic ions, generally the gadolinium chelate Gd-DTPA, have been generated and tested for their effects on MRI contrast of tumors and other tissues (U.S. Pat. No. 5,059,415). Unfortunately, the relaxivity of Gd bound to antibodies has been found to be only slightly better than that of unbound Gd-DTPA (Paajanen et al., Magn. Reson. Med 13: 38-43 (1990)).

MRI is generally used to detect $^{1}H$ nuclei in the living body. However, MRI is capable of detecting NMR spectrums of other nuclear species, including $^{13}C$, $^{15}N$, $^{31}P$, and $^{19}F$. The $^{19}F$ is not abundant in the living body. By incorporating isotopes useful in MRI, such as $^{13}C$, $^{15}N$, $^{31}P$, or $^{19}F$, and particularly $^{19}F$ in the compositions provided herein and administering to a subject, the compounds provided herein would accumulate in target tissue, and subsequent MR imaging would produce NMR data with enhanced signal from the targeted tissue or target compositions due to the presence of the accumulated compound with the MRI recognizable isotope, such as $^{19}F$. Thus, the disclosed compounds can be used as image enhancing agents and provide labeling of specific target tissues or target compositions for diagnostic radiology, including MRI.

C. Detecting Target Tissue or Target Compositions. In addition to PDT, the compositions provided herein can be used to detect target cells, target tissue, or target compositions in a subject. When the compounds provided herein are to be used for detection of target tissue or target composition, the compounds are introduced into the subject and sufficient time is allowed for the compounds to accumulate in the target tissue or to become associated with the target composition. The area of treatment is then irradiated, generally using light of an energy sufficient to cause fluorescence of the compound, and the energy used is usually significantly lower than is required for photodynamic therapy treatment. Fluorescence is determined upon exposure to light at the desired wavelength, and the amount of fluorescence can be correlated to the presence of the compound, qualitatively or quantitatively, by methods known in the art.

D. Diagnosing an Infecting Agent. The compositions provided herein can be used to diagnose the presence of an infecting agent, or the identity of an infecting agent in a subject. The compounds provided herein can be conjugated to one or more ligands specific for an infecting agent, such as an antibody or antibody fragment, that selectively associates with the infecting agent, and after allowing sufficient time for the targeted compound to associate with the infecting agent and to clear from non-target tissue, the compound can be visualized, such as by exposing to light of an energy sufficient to cause fluorescence of the compound, or by imaging using diagnostic radiology, including MRI. By way of example, any one of the compounds provided herein can be conjugated to an antibody that is targeted against a suitable *Helicobacter pylori* antigen, and formulated into a pharmaceutical preparation that, when introduced into a subject, releases the conjugated compound to a gastric mucus/epithelial layer where the bacterium is found. After sufficient time for the compound to selectively associate with the target infecting agent, and for any unbound compound to clear from non-target tissue, the subject can be examined to determine whether any *Helicobacter pylori* is present. This can be done by MRI to detect accumulated compound because of the presence of $^{19}F$ substituents, for example, or by irradiating the suspect target area with light of an energy sufficient to cause fluorescence of the compound, such as by using fiberoptics, and detecting any fluorescence of the targeted compound.

Detection Techniques.

Active compounds of the present invention can be detected by any suitable technique, including but not limited to flow cytometry, fluorescence spectroscopy, with a multi-well fluorescent plate scanner, scanning cytometry, fluorescent or immunofluorescent microscopy, laser scanning cytometry, bright field base image analysis, capillary volumetry, manual cell analysis and automated cell analysis. See, e.g., U.S. Pat. Nos. 5,314,805; 6,551,788 and 6,623,982.

Flow cytometry. Flow cytometry is known and described in, for example, U.S. Pat. Nos. 2,656,508; 2,869,078; 3,271,671; 5,915,925; 6,248,590; 6,524,860; 6,589,792; 6,604,435; and 6,890,487. In some embodiments the particle being detected, such as a cell, is labelled with a luminescent compound such as a phosphor or fluorophore for detection. Labelling can be carried out by any suitable technique such as coupling the luminescent compound to another compound such as an antibody which in turn specifically binds to the particle or cell, by uptake or internalization of the luminescent compound into the cell or particle, by non-specific adsorption of the luminescent compound to the cell or particle, etc. The active compounds described herein are useful in flow cytometry as such luminescent compounds, which flow cytometry techniques (including fluorescent activated cell sorting or FACS) may be carried out in accordance with known techniques or variations thereof which will be apparent to those skilled in the art based upon the instant disclosure.

Solar Cells, Light Harvesting Rods and Light Harvesting Arrays.

Compounds described herein may be used as chromophores (also referred to as photosensitizers or simply sensitizers) in solar cells, including but not limited to high surface area colloidal semiconductor film solar cells (Gratzel cells), as described in, for example, U.S. Pat. Nos. 5,441,827; 6,420,648; 6,933,436; 6,924,427; 6,913,713; 6,900,382; 6,858,158; and 6,706,963.

Compounds described herein may be used as chromophores in the light harvesting rods described in U.S. Pat. Nos. 6,407,330 and 6,420,648 (incorporated herein by reference). The light harvesting rod may comprise one or more bacteriochlorins of Formula I coupled to one or two adjacent chromophores depending upon the position thereof in the light harvesting rod. Such light harvesting rods may be utilized to produce light harvesting arrays as described in U.S. Pat. No. 6,420,648 and solar cells as described in U.S. Pat. No. 6,407,330.

Information Storage Devices.

Compounds described herein are also useful immobilized to a substrate for making charge storage molecules and information storage devices containing the same, either individually or as linked polymers thereof, either optionally including additional compounds to add additional oxidation states. Such charge storage molecules and information storage devices are known and described in, for example, U.S. Pat. No. 6,208,553 to Gryko et al.; U.S. Pat. No. 6,381,169 to Bocian et al.; and U.S. Pat. No. 6,324,091 to Gryko et al. The bacteriochlorins of the invention may comprise a member of a sandwich coordination compound in the information storage molecule, such as described in U.S. Pat. No. 6,212,093 to Li et al. or U.S. Pat. No. 6,451,942 to Li et al.

The present invention is explained in greater detail in the following non-limiting Examples.

Example 1

Installation of the Isocyclic Ring on Chlorins

We have been working to develop synthetic methods for preparing chlorins that can be used in diverse applications (Strachan, J.-P. et al., *J. Org. Chem.* 2000, 65, 3160-3172; Taniguchi, M. et al., *J. Org. Chem.* 2001, 66, 7342-7354; Laha, J. K. et al., *J. Org. Chem.* 2006, 71, 4092-4102). The synthesis of chlorins bearing a 5-substituent (alkyl or aryl) rely upon condensation of a 1-bromo-dipyrromethane-9-carbinol (Eastern half) and a 2,3,4,5-tetrahydro-1,3,3-trimethyldipyrrin (Western half) (Taniguchi, M. et al., *J. Org. Chem.* 2001, 66, 7342-7354; Laha, J. K. et al., *J. Org. Chem.* 2006, 71, 4092-4102). Chlorins lacking a 5-substituent can be prepared by condensation of a 1-bromo-dipyrromethane-9-carboxaldehyde (Eastern half) and a 2,3,4,5-tetrahydro-1,3,3-trimethyldipyrrin (Western half) (Ptaszek, M. et al., *J. Org. Chem.* 2006, 71, 4328-4331; Laha, J. K. et al., *J. Org. Chem.* 2006, 71, 4092-4102). Each chlorin incorporates a geminal dimethyl moiety in the reduced, pyrroline ring, thereby locking-in the hydrogenation level of the tetrapyrrole macrocycle at the dihydroporphyrin (i.e., chlorin) stage. These routes have enabled rational introduction of substituents at every peripheral site with the exception of the 7-position (Strachan, J.-P. et al., *J. Org. Chem.* 2000, 65, 3160-3172; Taniguchi, M. et al., *J. Org. Chem.* 2001, 66, 7342-7354; Ptaszek, M. et al., *J. Org. Chem.* 2006, 71, 4328-4331; Balasubramanian, T. *J. Org. Chem.* 2000, 65, 7919-7929; Taniguchi, M. et al., *J Org. Chem.* 2002, 67, 7329-7342; Taniguchi, M. et al., *J. Org. Chem.* 2005, 70, 275-285); See Example 2 below). Given the difficulties of installing an isocyclic ring on the chlorin macrocycle, we previously investigated the effects of other, more accessible substituents that might afford enhanced red absorption spectral features. In this regard, 3-vinyl, 3-ethynyl, 13-ethynyl, and 13-acetyl groups were investigated and found to have pronounced effects on the spectral properties of the chlorin macrocycle (See Example 2 below).

Results and Discussion

I. Synthesis. In the previous paper (See Example 2 below), we prepared an 8,9-dibromo derivative of a 1-formyldipyrromethane (Eastern half), which upon acid-catalyzed condensation with a tetrahydrodipyrrin Western half followed by metal-mediated oxidative cyclization afforded the corresponding 13-bromochlorin. Pd-mediated coupling of the latter with tributyl(1-ethoxyvinyl)tin and subsequent acidic workup gave the 13-acetylchlorin. We employed a similar strategy here, but with use of an Eastern half bearing a 1-carbinol group. The resulting chlorin incorporates two meso substituents in addition to the 13-acetyl group.

Chlorin Precursors. An 8,9-dibromo derivative of a 1-acyldipyrromethane was prepared as shown in Scheme 1. Treatment of 5-mesityldipyrromethane (1) (Laha, J. K. et al., *Org. Process Res. Dev.* 2003, 7, 799-812) with 3.0 molar equiv of EtMgBr at room temperature followed by Mukaiyama reagent 2 (Rao, P. D. et al., *J. Org. Chem.* 2000, 65, 1084-1092) at −78° C. gave the 1-acyldipyrromethane 3 in 73% yield. This route is superior to a prior acylation of 1 with p-toluoyl chloride that afforded 3 in 37% yield (Taniguchi, M. et al., *J. Org. Chem.* 2001, 66, 7342-7354). Treatment of 3 with 2.2 molar equiv of NBS at −78° C. gave the dibromo-product 4 along with several side products. Compound 4, although quite labile, was handled effectively by workup without heating and by avoiding adverse solvents (ethyl acetate, chlorinated hydrocarbons). In so doing, workup including column chromatography afforded 4 in 57% yield.

Scheme 1

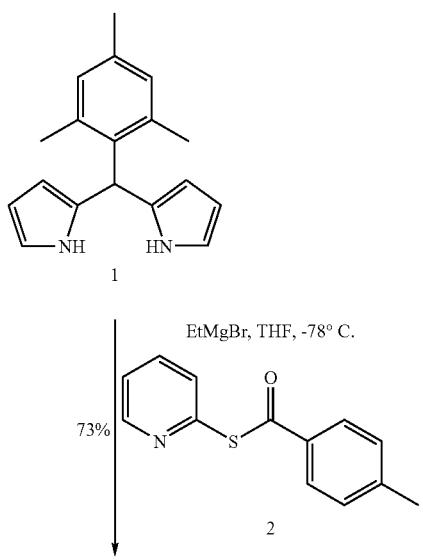

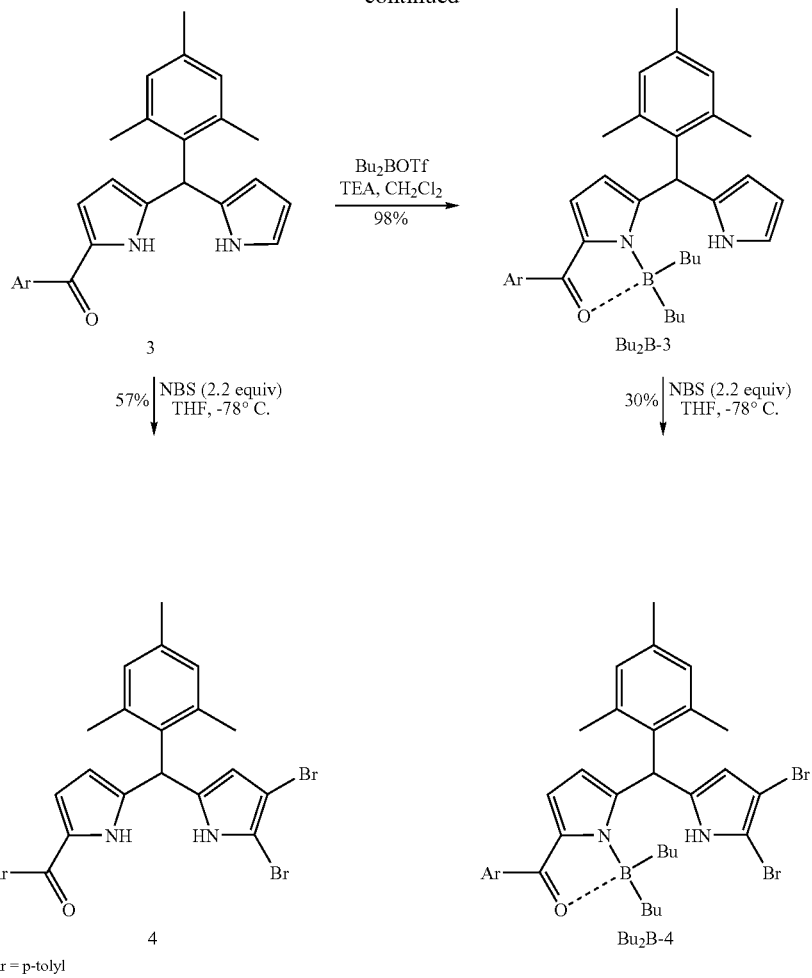

Ar = p-tolyl

The regiochemistry of the 1,2-dibromo-substitution pattern in 4 was established by NMR spectroscopy ($^1$H-$^1$H 2D-COSY and 1D-NOE experiments). The regioselective formation of dibromo-product 4 can be explained in part by the fact that the α-acylpyrrole ring is deactivated, whereupon substitution takes place exclusively in the non-deactivated pyrrole ring at the vicinal α- and β-positions. The purified compound 4 decomposed almost completely within 8-10 hours in solution even at 0° C., but was stable as a powdered solid upon storage at −10° C. for 1-2 days. Compound 4 decomposed several times during NMR measurements (regardless of solvent such as CDCl$_3$, C$_6$D$_6$ or THF-d$_8$) or attempted crystallization. The corresponding dibutylboron complex (Muthukumaran, K. et al., *J. Org. Chem.* 2004, 69, 5354-5364) of the 1-acyldipyrromethane 3 (BBu$_2$-3) was prepared and converted to the 8,9-dibromo product (BBU$_2$-4) but no significant increase in stability was achieved. It should be noted that the synthesis of the 1-acyl-8,9-dibromodipyrromethane was inspired by the occurrence and demonstrated synthesis of analogous polyhalogenated pyrroles from marine organisms (Bailey, D. M.; Johnson, R. E. *J. Med. Chem.* 1973, 16, 1300-1302; Bailey, D. M. et al., *J. Med. Chem.* 1973, 16, 1298-1300; Gilow, H. M.; Burton, D. E. *J. Org. Chem.* 1981, 46, 2221-2225; Keifer, P. A. et al., *J. Org. Chem.* 1991, 56, 2965-2975; Matsuki, S. et al., *J. Heterocyclic Chem.* 1997, 34, 87-91; Olofson, A. et al., *J. Org. Chem.* 1998, 63, 1248-2225; He, R. H.-Y.; Jiang, X.-K. *J. Chem. Research (S)* 1998, 786-787; Armitt, D. J. et al., *J. Chem. Soc., Perkin Trans.* 1, 2002, 1743-1745; Hoffmann, H.; Lindel, T. *Synthesis* 2003, 1753-1783; Patel, J. et al., *J. Org. Chem.* 2005, 70, 9081-9084). However, in most such pyrroles, the halogens and the acyl group are located in the same pyrrole, which must be considerably stabilized by the acyl group.

Chlorin Formation. Although we were concerned that the limited stability of 4 might prevent conversion to the chlorin, we proceeded with the synthesis (Scheme 2).

Reduction of 4 with NaBH$_4$ at room temperature for 3 h gave the corresponding dipyrromethane-1-carbinol (Eastern half). The completion of reduction can be monitored by TLC analysis (hexanes/ethyl acetate=3/1). The resulting dipyrromethane-monocarbinol is quite labile but was handled effectively in the same manner as for 4. The crude product was condensed with Western half 5 under the standard conditions of TFA catalysis. The putative tetrahydrobilene-α formed in situ was subjected to metal-catalyzed oxidative cyclization in the presence of air. After the formation of tetrahydrobilene α, 2,2,6,6-tetramethylpiperidine was added slowly at 0° C. followed by Zn(OAc)$_2$ and AgOTf. The resulting mixture was refluxed for 18 h exposed to air. In this manner, the zinc chelate of the 13-bromochlorin (Zn-6) was isolated in 14% yield from the dibromo derivative 4.

Scheme 2

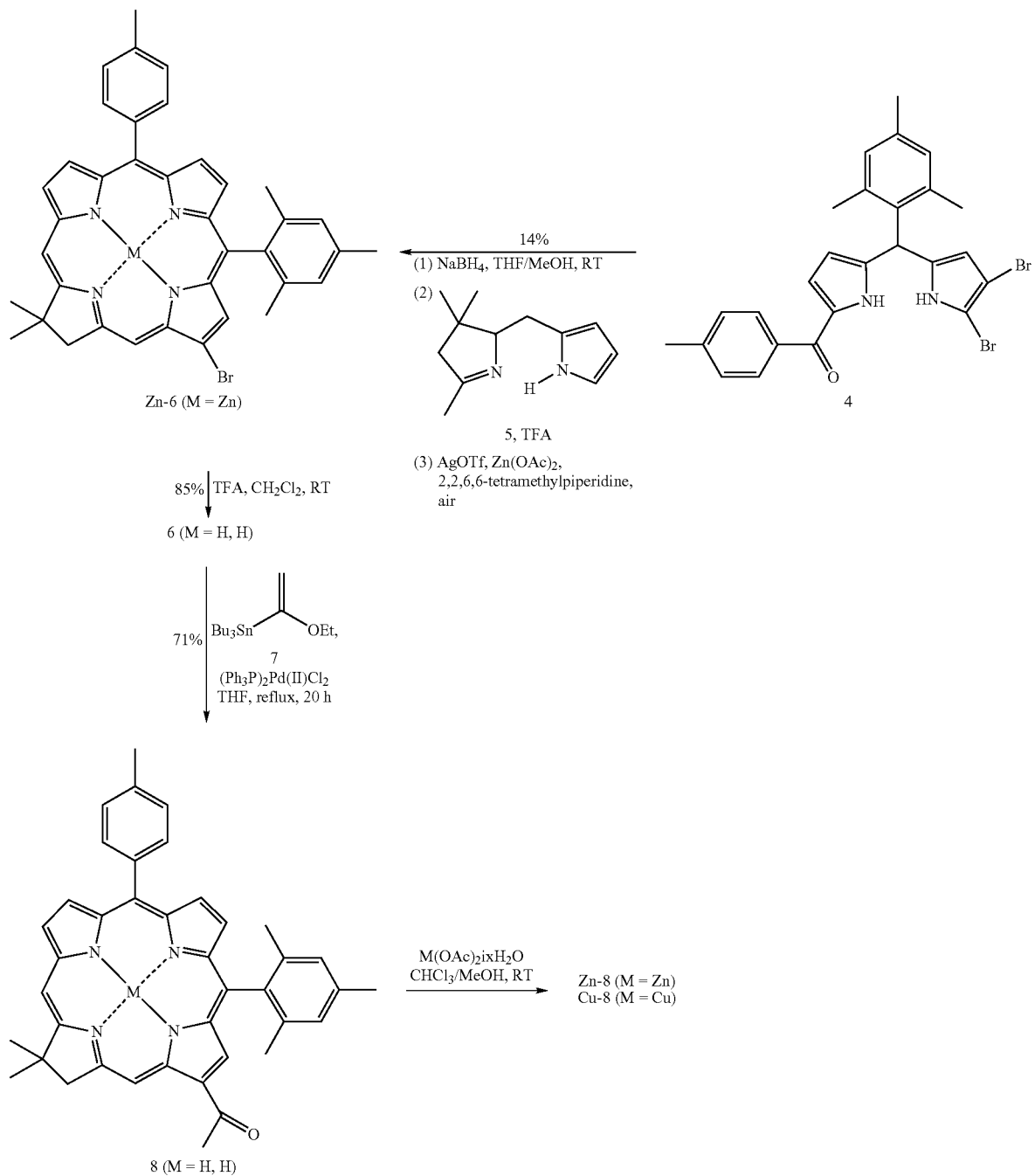

The conversion of the 13-bromochlorin Zn-6 to the 13-acetylchlorin is shown in Scheme 2. A limited amount of optimization proved necessary. Thus, heating a reaction mixture of Zu-6 (10 mM), tributyl(1-ethoxyvinyl)tin [7 (12 mM); Kosugi, M. et al., *Bull. Chem. Soc. Jpn.* 1987, 60, 767-768] and 10 mol % of $(PPh_3)_2PdCl_2$ at 85° C. in toluene for 20 h followed by hydrolysis of the reaction mixture with 10% aqueous HCl gave 8 in 7% yield along with the recovery of free base 13-bromo chlorin 6 (~55% yield). Changing the solvent from toluene to THF and heating the reaction mixture at 55° C. for 20 h gave little improvement (17%). A somewhat better result was observed when the mixture of Zn-6 (20 mM), 7 (40 mM) and 20 mol % of $(PPh_3)_2PdCl_2$ was heated at 55° C. in THF for 36 h, whereupon 8 was isolated in 29% yield along with the recovery of free-base 13-bromo chlorin 6 (~22%). The synthesis of 8 was further improved by carrying out the palladium coupling using free base chlorin 6. Thus, demetalation of Zn-6 with TFA in $CH_2Cl_2$ at room temperature gave free-base 13-bromochlorin 6 in 85% yield. The coupling of 6 (10 mM) and 7 (20 mM) was carried out in the presence of 10 mol % of $(PPh_3)_2PdCl_2$ in THF for 20 h. Hydrolysis of the reaction mixture with 10% aqueous. HCl and standard workup gave 13-acetylchlorin 8 in 71% yield. Compound 8 was characterized by absorption and fluorescence spectroscopy, $^1$H NMR spectroscopy, LD-MS and FAB-MS analyses. The free-base 13-acetylchlorin 8 was metalated with Zn(OAc)$_2$.2H$_2$O or Cu(OAc)$_2$.H$_2$O to obtain Zn-8 or Cu-8, respectively. The X-ray structure of Cu-8 confirmed the presence of the acetyl group at the 13-position of the chlorin macrocycle (not shown).

Isocyclic Ring Installation. The installation of the isocyclic ring on free-base 13-acetylchlorin 8 was envisaged by the intramolecular ring closure of the 13-acetyl group to the 15-position of the chlorin macrocycle. The α-arylation of aliphatic ketones is well known and has been carried out on a wide variety of aryl substrates. Such reactions have been carried out recently using (PPh$_3$)$_2$PdCl$_2$ in the presence of Cs$_2$CO$_3$ in THF at reflux (Muratake, H.; Natsume, M. *Tetrahedron Lett*. 1997, 38, 7581-7582; Muratake, H. et al., Tetrahedron 2004, 60, 11783-11803). The successful intramolecular ring closure of the 13-acetyl group to the 15-position of the chlorin macrocycle requires a bromo substituent at the 15-position. Recently, the selective halogenation of chlorins at the 15-position followed by palladium coupling reactions enabled introduction of 15-aryl substituents (Taniguchi, M. et al., *J. Org. Chem*. 2005, 70, 275-285). Treatment of 8 with 1 equiv of NBS at room temperature for 2 h gave the 15-bromochlorin 9 in 73% yield. Treatment of the crude 15-bromochlorin with (PPh$_3$)$_2$PdCl$_2$ in the presence of Cs$_2$CO$_3$ in toluene at reflux resulted in intramolecular cyclization to form phorbine 10 in 44% overall yield from 8 (Scheme 3). Phorbine 10 was characterized by absorption and fluorescence spectroscopy, IR and $^1$H NMR spectroscopy, LD-MS, and FAB-MS analysis.

A novel feature of this ring-closure process with regards to the α-arylation of aliphatic ketones is that the product is ortho-perifused rather than merely ortho-fused. The simplicity of this transformation makes this route quite attractive as a means of installing the isocyclic ring. For perspective, it should be mentioned that Smith and coworkers subjected a porphyrin bearing substituents at all β-positions except position 13 to mercuration followed by palladium coupling with methyl acrylate, affording the 13-acrylate porphyrin (Smith, K. M. et al., *J. Org. Chem*. 1984, 49, 4602-4609). This early approach for derivatizing the 13-position is suited for porphyrinic molecules bearing a single β-unsubstituted site. By contrast, the route described herein builds in the requisite functionality at the dipyrromethane stage, enabling derivatization of a chlorin macrocycle containing a defined pattern of substitution with many unsubstituted β-sites.

Scheme 3

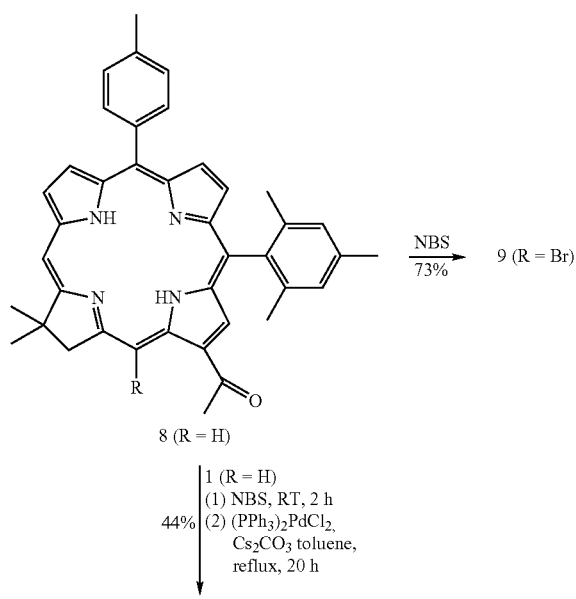

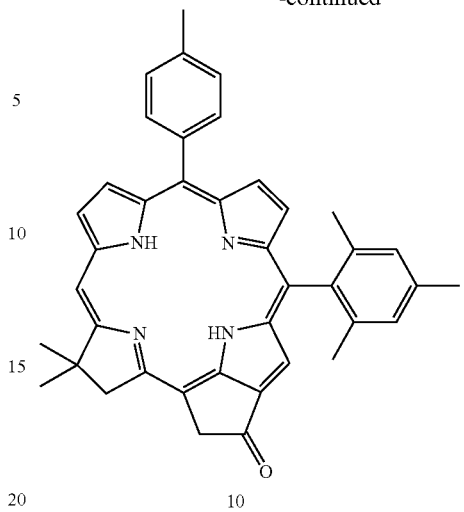

II. Nomenclature. The nomenclature for chlorophyll-like compounds understandably relies very heavily on trivial names for derivatives and degradation products of chlorophyll. The ring system for phorbine, which is recognized by IUPAC, provides a versatile parent hydrocarbon for naming chlorins containing an isocyclic ring, including those described herein. However, the IUPAC definition for phorbine adheres to a numbering system that is at odds with the universally accepted numbering system for porphyrins and chlorins (Moss, G. P. *Pure Appl. Chem*. 1987, 59, 779-832). We have adopted the phorbine ring system shown as the parent hydrocarbon for naming purposes, but with use of the more reasonable chlorophyll-derived numbering system (Chart 1). Alternatively, the chlorin containing an isocyclic ring can be named as a derivative of a porphyrin while again maintaining the chlorophyll-derived numbering system. Thus, compound 10 is a 13$^1$-oxophorbine, or, alternatively, a 13$^1$,13$^2$,17,18-tetrahydro-13$^1$-oxocyclopenta[m,n]porphine.

Chart 1

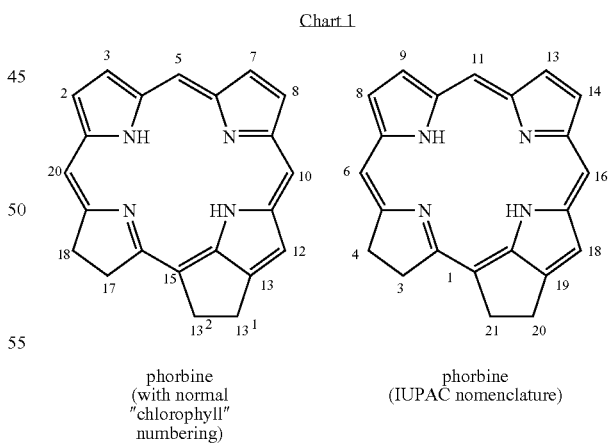

phorbine (with normal "chlorophyll" numbering)

phorbine (IUPAC nomenclature)

III. Spectral Properties.

IR Spectroscopy. IR spectroscopy can provide valuable information about the conjugation of the 13-keto group with the chlorin macrocycle. 13-Acetylchlorin 8 exhibits a carbonyl stretch ($v_{max}$) at 1728 cm$^{-1}$ (KBr), whereas that of phorbine 10 appears at 1701 cm$^{-1}$ (KBr). For comparison, the carbonyl stretch of analogous compounds includes 3-acetyl- 2-methylpyrrole (1639 cm⁻¹) (Loader, C. E.; Anderson, H. J. *Tetrahedron* 1969, 25, 3879-3885), acetophenone (1683 cm⁻¹), pheophytin α (1705 cm¹), (Katz, J. J. et al., in *The Chlorophylls*, Vernon, L. P.; Seely, G. R., Eds., Academic Press: New York, 1966, pp 185-251), methyl pheophorbide a (1703 cm⁻¹) (Katz, J. J. et al., in *The Chlorophylls*, Vernon, L. P.; Seely, G. R., Eds., Academic Press: New York, 1966, pp 185-251), and methyl pyropheophorbide α (1695 cm⁻¹), (Katz, J. J. et al., in *The Chlorophylls*, Vernon, L. P.; Seely, G. R., Eds., Academic Press: New York, 1966, pp 185-251). A reasonable interpretation is that the keto group in simple aromatic compounds is more conjugated with the aromatic nucleus, and has greater single-bond character, compared to that of the synthetic or naturally occurring phorbines (i.e., 10 and the chlorophyll derivatives). Not surprisingly, the keto group in 13-acetylchlorin 8 is less conjugated than that in phorbine 10.

Absorption Spectra. The spectral properties of interest in the chlorins include the position of the long-wavelength $Q_y$ transition, the intensity of the $Q_y$ transition, and the fluorescence quantum yield of the chlorin. The intensity of the $Q_y$ transition can be assessed by the measured molar absorption coefficient; however, comparisons of such values are somewhat unreliable given the experimental variability encountered upon handling small quantities of materials. A better comparison is achieved by examination of the ratio of the intensities of the B and $Q_y$ bands for a given compound (B/$Q_y$ ratio), which is determined simply by absorption spectroscopy without requiring determination of the molar absorption coefficient. For a wide variety of applications, bathochromic and hyperchromic shifts of the $Q_y$ band are desired (i.e., shifted to longer wavelength and intensified), thereby affording strong absorption in the deep-red region.

The spectral properties of the chlorins are listed in Table 1. Appropriate benchmark compounds include the zinc or free base chlorins (11, Zn-11) (Strachan, J.-P. et al., *J. Org. Chem.* 2000, 65, 3160-3172), lacking any 13-substituent (Chart 2), the zinc-chelated analogues of chlorophyll a or b (Jones, I. D. et al., *J. Agric. Food Chem.* 1968, 16, 80-83), and chlorophyll a (Strain, H. H.; Svec, W. A. in *The Chlorophylls*, Vernon, L. P.; Seely, G. R., Eds., Academic Press: New York, 1966, pp 21-66).

Chart 2

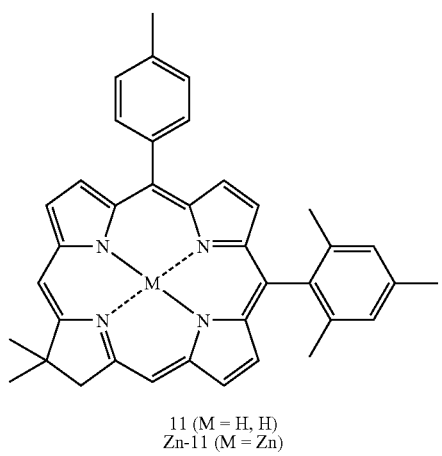

11 (M = H, H)
Zn-11 (M = Zn)

Comparison of the data for Zn-8 and Zn-11 show that introduction of the 13-acetyl substituent redshifts the $Q_y$ band by 27 nm and increases the $Q_y$ band intensity. The latter can be assessed either by comparison of molar absorption coefficients (log ε=4.75 vs. 4.64) or by comparison of the B/$Q_y$ band ratios (2.9 vs. 4.2).

TABLE 1

Absorption Properties of Chlorins[a]

| chlorins | $\lambda_{max}$ (nm), B | $\lambda_{max}$ (nm), $Q_y$ | Log ε (M⁻¹cm⁻¹) ($Q_y$ band) | B/$Q_y$ intensity ratio |
|---|---|---|---|---|
| chlorophyll a[b] | 430 | 662 | 4.93 | 1.3 |
| Zn-chlorophyll a[c] | 423 | 653 | — | 1.4 |
| Zn-chlorophyll b[c] | 446 | 634 | — | 2.9 |
| Zn-8 | 424 | 635 | 4.75 | 2.9 |
| Cu-8 | 420 | 631 | 4.69 | 3.1 |
| Zn-11 | 412 | 608 | 4.64 | 4.2 |
| Zn-6 | 414 | 616 | 4.65 | 4.0 |
| pheophytin a[d] | 408 | 667 | 5.12 | 2.1 |
| 8 | 422 | 661 | 4.67 | 2.3 |
| 11 | 414 | 641 | 4.45 | 3.1 |
| 10 | 417 | 660 | — | 2.5 |

[a]In toluene at room temperature unless noted otherwise.
[b]Ref Strain, H. H.; Svec, W. A. in The Chlorophylls, Vernon, L. P.; Seely, G. R., Eds., Academic Press: New York, 1966, pp 21-66 (in diethyl ether).
[c]Ref Jones, I. D. et al., J. Agric. Food Chem. 1968, 16, 80-83 (in diethyl ether).
[d]Ref Smith, J. H. C.; Benitez, A. In Modern Methods of Plant Analysis; Paech, K., Tracey, M. V., Eds.; Springer-Verlag: Berlin, 1955; Vol. IV, pp 142-196 (in diethyl ether).

The spectra of Zn-8 and Zn-11 are shown in FIG. 1. Similar observations are also found in the corresponding free base chlorins.

The enhancement in intensity and wavelength of the $Q_y$ band in 13-acetylchlorins is explained as follows. The acetyl group at 13-position can adopt a planar conformation and thus conjugate with the 1-electrons of the macrocycle. The crystal structure of Cu-8 shows the near co-planarity of the acetyl group with the chlorin macrocycle in the solid state. It has been shown that the acetyl group of 13-acetylporphyrins in an unhindered β-pyrrolic position can adopt a planar conformation and thus conjugate with the π-electron of the macrocycle (Balaban, T. S. et al., *Eur. J. Org. Chem.* 2004, 3919-3930). However, the carbonyl group is pointed toward the 15-position rather than toward the 12-position (as in chlorophylls). While the presence of the acetyl group in the synthetic 13-acetylchlorins significantly changes the wavelength and intensity of the $Q_y$ band, the absorption properties of Zn-8 do not completely mimic those of chlorophyll. For example, Zn-8 absorbs at 424 and 635 nm whereas chlorophyll a absorbs at 430 and 662 nm. Moreover, the B/$Q_y$ band intensity ratio (2.9) in Zn-8 is much greater than that (1.3) of chlorophyll α. The spectra described above were recorded in solution, where the 13-acetyl group is expected to have considerable conformational freedom of rotation versus that of the carbonyl group in the isocyclic ring of chlorophylls.

The presence of the isocyclic ring in free base phorbine 10 redshifts the $Q_y$ band by 19 nm and affords a relative increase in intensity of the $Q_y$ band, by comparison with the benchmark chlorin 11. The spectra of 10 and 11 are shown in FIG. 2. The $Q_y$ position of phorbine 10 (660 nm) closely resembles that of pheophytin a (667 nm) (Smith, J. H. C.; Benitez, A. In *Modern Methods of Plant Analysis*; Paech, K., Tracey, M. V., Eds.; Springer-Verlag: Berlin, 1955; Vol. IV, pp 142-196), the free base analogue of chlorophyll α.

Fluorescence Properties. The free-base 13-acetylchlorin 8 exhibits a strong $Q_y$(0,0) fluorescence band at approximately 668 nm and a weak emission feature with two discernible maxima (~711 and 744 nm). The zinc chelate Zn-8 has a dominant fluorescence band at around 641 nm and a broad weak band in the region 670-720 nm. The fluorescence quantum yield ($\Phi_f$) of free-base chlorin 8 is 0.23, while that of Zn-8 is 0.24. These data are to be compared with those of 10 (0.29) and Zn-11 (0.065) (Strachan, J.-P. et al., *J. Org. Chem.* 2000, 65, 3160-3172).

Conclusions. A new route has been developed for installing the isocyclic ring on tetrapyrrole macrocycles. The route entails preparation of a 13-acetylchlorin; which undergoes bromination at the 15-position followed by a Pd-mediated α-arylation procedure. The α-arylation procedure proceeds under mild conditions. The presence of a keto group at the 13-position significantly redshifts the absorption maximum and affords a relative increase in the intensity of the $Q_y$ band. The ability to install the isocyclic ring opens up a number of possible applications ranging from use in artificial photosynthesis to photomedicine.

Experimental Section

General. $^1$H NMR (400 MHz) and $^{13}$C NMR (75 MHz) spectra were collected at room temperature in $CDCl_3$. Absorption spectra were obtained in toluene at room temperature. Chlorins were analyzed by laser desorption mass spectrometry (LD-MS) in the absence of a matrix. Fast atom bombardment mass spectrometry (FAB-MS) data are reported for the molecule ion or protonated molecule ion. Melting points are uncorrected. All commercially available materials were used as received. All palladium-coupling reactions were carried out using standard Schlenk-line techniques.

The chlorin-forming reaction was performed during a single day starting from the preparation of the 8,9-dibromo-1-formyldipyrromethane. The condensation of an Eastern half and the Western half was carried out at room temperature under argon. The condensation reaction mixture was quenched with ice-cold aqueous $NaHCO_3$. An ice-cold solution of the crude product in $CH_3CN$ was treated with 2,2,6,6-tetramethylpiperidine (TMP) followed by $Zn(OAc)_2$ and AgOTf. The reaction mixture was stirred at room temperature for 10-15 min before set it to gentle reflux.

Fluorescence Spectroscopy. The fluorescence spectra and fluorescence quantum yields reported herein were collected in toluene at room temperature. Measurements of fluorescence quantum yield ($\Phi_f$) were carried out using chlorin Zn-11 ($\Phi_f$=0.065) as a standard (Strachan, J.-P. et al., *J. Org. Chem.* 2000, 65, 3160-3172).

Noncommercial Compounds. Compounds I (Laha, J. K. et al., *Org. Process Res. Dev.* 2003, 7, 799-812), 2, 3 (Rao, P. D. et al., *J. Org. Chem.* 2000, 65, 1084-1092), and 5 (Taniguchi, M. et al., *J. Org. Chem.* 2001, 66, 7342-7354) were prepared following literature procedures.

5-Mesityl-1-(4-methylbenzoyl)dipyrromethane (3). Following a reported procedure (Rao, P. D. et al., *J. Org. Chem.* 2000, 65, 1084-1092), a solution of EtMgBr (30.0 mL, 30.0 mmol, 1.0 M solution in THF) was added dropwise to a solution of 1 (2.64 g, 10.0 mmol) in dry THF (50 mL) over a 5 min period. The solution was stirred at room temperature for 30 min. The solution was cooled to −78° C. and then a solution of 2 (2.75 g, 12.0 mmol) in dry THF (20 mL) was added dropwise. The mixture was stirred for 3 h at −78° C. Saturated aqueous $NH_4Cl$ was added. The mixture was extracted with $CH_2Cl_2$. The organic phase was dried ($Na_2SO_4$), concentrated and chromatographed [silica, hexanes/$CH_2Cl_2$/ethyl acetate (7:2:1)], affording a pale yellow solid (2.80 g, 73%): mp 74-75° C. [lit.[13] 75-77° C.]; $^1$H NMR δ 2.10 (s, 6H), 2.30 (s, 3H), 2.43 (s, 3H), 5.96 (s, 1H), 6.12 (m, 2H), 6.22 (m, 1H), 6.68 (s, 1H), 6.83 (m, 1H), 6.90 (s, 2H), 7.26 (d, J=7.5 Hz, 2H), 7.77 (d, J=7.5 Hz, 2H), 7.85 (brs, 1H), 9.23 (brs, 1H); $^{13}$C NMR δ 20.6, 20.7, 21.5, 38.6, 107.1, 108.9, 109.9, 116.8, 120.1, 128.9, 129.1, 129.9, 130.5, 133.1, 135.7, 137.2, 137.4, 140.4, 142.1, 183.9; Anal. Calcd for $C_{26}H_{26}N_2O$: C, 81.64; H, 6.85; N, 7.32. Found: C, 81.49; H, 7.01; N, 7.01.

10-(Dibutylboryl)-5-mesityl-1-p-toluoyldipyrromethane ($Bu_2B$-3). Following a general procedure (Muthukumaran, K. et al., *J. Org. Chem.* 2004, 69, 5354-5364), a solution of 3 (230 mg, 0.600 mmol) in $CH_2Cl_2$ (3.2 mL) was treated with TEA (0.200 mL, 1.44 mmol) followed by $Bu_2BOTf$ (1.20 mL, 1.20 mmol) in hexanes. After 2 h, the mixture was passed through a pad of silica (2×8 cm) eluting with $CH_2Cl_2$. The fast moving yellow fractions were collected and concentrated, affording an orange oil (300 mg, 98%): $^1$H NMR δ 0.36-0.52 (m, 2H), 0.61 (t, J=7.2 Hz, 3H), 0.78 (t, J=7.2 Hz, 3H), 0.82-0.98 (m, 4H), 1.16-1.22 (m, 6H), 2.18 (s, 6H), 2.26 (s, 3H), 2.47 (s, 3H), 5.86 (s, 1H), 5.88 (m, 1H), 6.19 (m, 1H), 6.42 (d, J=4.1 Hz, 1H), 6.83 (m, 1H), 6.91 (s, 2H), 7.19 (d, J=4.1 Hz, 1H), 7.37 (d, J=8.1 Hz, 2H), 7.82 (brs, 1H), 8.10 (d, J=8.1 Hz, 2H); $^{13}$C NMR δ 14.3, 14.5, 20.9, 21.7, 22.1, 26.1, 26.3, 27.3, 27.5, 40.0, 107.9, 108.8, 116.7, 122.0, 128.1, 129.9, 130.0, 130.4, 130.6, 135.2, 136.8, 137.3, 145.2, 151.5, 176.0; Anal. Calcd for $C_{34}H_{43}BN_2O$: C, 80.62; H, 8.56; N, 8.56. Found: C, 81.22; H, 9.83; N, 8.54; FAB-MS obsd 506.3458, calcd 506.3468 ($C_{34}H_{43}BrN_2O$).

Note: Compound $Bu_2B$-3 decomposes partially at room temperature.

8,9-Dibromo-5-mesityl-1-(4-methylbenzoyl)dipyrromethane (4). Following a procedure for 8,9-dibromination of 1-acyldipyrromethanes (See Example 2 below), a solution of 3 (573 mg, 1.50 mmol) in dry THF (15 mL) at −78° C. under argon was treated portionwise with NBS (587 mg, 3.30 mmol). The reaction mixture was stirred for 1 h at −78° C. Hexanes was added to the reaction mixture at −20° C. The reaction mixture was then allowed to warm to 0° C. The organic layer was washed with ice-cold water, dried ($K_2CO_3$) and concentrated without heating in a water-bath at ambient temperature. The resulting brown solid was purified by column chromatography [silica, hexanes/$CH_2Cl_2$/ethyl acetate (7:2:1)], affording a yellow solid (0.465 g, 57%): mp 120-122° C. (dec); $^1$H NMR δ 2.08 (s, 6H), 2.30 (s, 3H), 2.42 (s, 3H), 5.81 (s, 1H), 6.05 (d, J=3.3 Hz, 1H), 6.12 (dd, J=4.2, 3.3 Hz, 1H), 6.80 (dd, J=4.2, 3.3 Hz, 1H), 6.90 (s, 2H), 7.26 (d, J=8.1 Hz, 2H), 7.74 (d, J=8.1 Hz, 2H), 8.07 (brs, 1H), 9.10 (brs, 1H); $^{13}$C NMR δ 320.3, 21.0, 21.8, 39.0, 98.7, 99.2, 110.4, 111.4, 120.2, 29.2, 130.6, 131.0, 131.7, 131.8, 135.7, 137.6, 138.0, 139.0, 142.7, 184.2; FAB-MS obsd 538.0240, calcd 538.0255 ($C_{26}H_{24}Br_2N_2O$).

Notes: (1) The use of ethyl acetate or any chlorinated solvent should be avoided during workup. All of the workup operations including solvent removal should be done without heating, and preferably under chilled conditions.

(2) The crude mixture is poorly soluble in hexanes/$CH_2Cl_2$/ethyl acetate (7:2:1), a recommended solvent for column chromatography. Therefore, a minimum amount of THF can be employed along with the above solvent mixture before loading on the column.

(3) Isolated pure 4 is labile. Careful handling of the solution of compound 4 is required. Compound 4 decomposes almost completely in solution (such as in ethyl acetate or chlorinated solvent) within 8-10 h even at 0° C. The powdered solid 4 can be stored at −10° C. for 1-2 days without decomposition. Compound 4 decomposed several times during NMR measurements (regardless of solvent such as $CDCl_3$, $C_6D_6$ or THF-$d_8$) or attempted crystallization.

8,9-Dibromo-10-(dibutylboryl)-5-mesityl-1-p-toluoyldipyrromethane ($Bu_2B$-4). A solution of 3-$Bu_2B$ (200 mg, 0.400 mmol) in dry THF (4 mL) was treated with NBS (156 mg, 0.880 mmol) at −78° C. The reaction mixture was stirred for 1 h at −78° C. Hexanes and water were added to the reaction mixture at −20° C. The organic layer was dried (Na$_2$SO$_4$) and the solvent was removed without heat. The crude mixture was concentrated and chromatographed [silica, hexanes/toluene (1:1)], affording a brown solid (80 mg, 30%): mp 55° C. (dec); $^1$H NMR δ 0.20-0.42 (m, 2H), 0.58 (t, J=7.2 Hz, 3H), 0.78 (t, J=7.2 Hz, 3H), 0.82-0.98 (m, 4H), 1.16-1.22 (m, 6H), 2.15 (s, 6H), 2.27 (s, 3H), 2.47 (s, 3H), 5.80 (s, 1H), 5.89 (m, 1H), 6.46 (d, J=4.1 Hz, 1H), 6.84 (s, 2H), 7.20 (d, J=4.1 Hz, 1H), 7.35 (d, J=8.1 Hz, 2H), 7.81 (brs, 1H), 8.10 (d, J=8.1 Hz, 2H); $^{13}$C NMR δ 14.3, 14.5, 20.9, 21.3, 21.7, 22.2, 26.1, 26.2, 26.3, 27.2, 27.6, 40.1, 98.1, 99.2, 111.9, 116.8, 121.3, 127.9, 130.0, 130.1, 130.8, 132.7, 133.4, 135.4, 137.3, 137.4, 145.6, 149.1, 176.7; FAB-MS obsd 662.1668, calcd 662.1679 (C$_{34}$H$_{41}$BBr$_2$N$_2$O).

Note: The stability of Bu$_2$B-4 is similar to that of compound 4. All the points noted above for compound 4 are equally applicable for Bu$_2$B-4.

Zn(II)-13-Bromo-17,18-dihydro-10-mesityl-18,18-dimethyl-5-p-tolylporphyrin (Zn-6). Following a reported procedure (Taniguchi, M. et al., *J. Org. Chem.* 2001, 66, 7342-7354), a solution of 4 (465 mg, 0.860 mmol) in THF/MeOH (4:1, 45 mL) was treated portionwise with a sample of NaBH$_4$ (325 mg, 8.60 mmol) at 0° C. and the reaction mixture was stirred at room temperature for 3 h under argon. Saturated aqueous NH$_4$Cl was added at 0° C. The mixture was extracted with ethyl acetate (ice-cold). The combined organic extracts were dried (K$_2$CO$_3$) and concentrated under reduced pressure without heating. The crude mixture was placed on a vacuum line for a few minutes to remove residual solvent, affording a yellow foam-like solid. The resulting solid was dissolved in anhydrous CH$_3$CN (8.6 mL) at 0° C. Western half 5 (164 mg, 0.860 mmol) was added followed by dropwise addition of TFA (64 µL, 0.83 mmol). The reaction mixture was stirred at room temperature under argon for 30 min. The reaction mixture was diluted with CH$_3$CN (77 mL) at 0° C. 2,2,6,6-Tetramethylpiperidine (1.52 mL, 9.00 mmol) was added and the reaction mixture was stirred at 0° C. for 5-10 min. Zn(OAc)$_2$ (1.10 g, 6.00 mmol) was added followed by AgOTf (464 mg, 1.80 mmol). The resulting suspension was refluxed for 18 h exposed to air. The crude mixture was concentrated and chromatographed [silica, hexanes/CH$_2$Cl$_2$ (2:1)], affording a green solid (83 mg, 14%): $^1$H NMR δ 1.86 (s, 6H), 2.02 (s, 6H), 2.58 (s, 3H), 2.66 (s, 3H), 4.53 (s, 2H), 7.21 (s, 2H), 7.48 (d, J=8.1 Hz, 2H), 7.94 (d, J=8.1 Hz, 2H), 8.22 (d, J=4.8 Hz, 1H), 8.35 (d, J=4.4 Hz, 1H), 8.50 (s, 1H), 8.56 (s, 1H), 8.64 (d, J=4.8 Hz, 1H), 8.66 (d, J=4.4 Hz, 1H), 8.79 (s, 1H); LD-MS obsd 691.7; FAB-MS obsd 688.1178, calcd 688.1180 (C$_{38}$H$_{33}$BrN$_4$Zn); λ$_{abs}$ 414, 616 nm.

Notes: (1) The completion of reduction can be monitored by TLC analysis (hexanes/ethyl acetate, 3:1). On some occasions, reduction of 4 using 10 equiv of NaBH$_4$ is not complete in 3 h. In that case, it is necessary to add more (5 equiv) NaBH$_4$ in the reaction mixture or stir the reaction mixture for a prolonged period. The use of chlorinated solvents should be avoided during workup. All of the operations including solvent removal should be done without heating and preferably under chilled conditions. The resulting dipyrromethane-1-carbinol changes color from yellow to reddish during removal of the residual solvent.

(2) During the tetrahydrobilene a formation, all operations (such as addition of Western half or TFA) should be done as quickly as possible. After 30 min, the color of the reaction mixture changed from yellow to reddish brown.

(3) After the reaction forming the tetrahydrobilene α, the slow addition of 2,2,6,6-tetramethylpiperidine in the reaction mixture at 0° C. is necessary.

13-Bromo-17,18-dihydro-10-mesityl-18,18-dimethyl-5-p-tolylporphyrin (6). A solution of Zn-6 (97 mg, 0.14 mmol) in CH$_2$Cl$_2$ (2 mL) was treated dropwise with TFA (0.20 mL, 2.6 mmol) over a 10 min period. The solution was stirred at room temperature for 2 h. CH$_2$Cl$_2$ was added and the organic layer was washed (saturated aqueous NaHCO$_3$, water, and brine) and then dried (Na$_2$SO$_4$). The crude mixture was concentrated and chromatographed [silica, hexanes/CH$_2$Cl$_2$ (2:1)], affording a purple solid (75 mg, 850%): $^1$H NMR δ-1.70 (brs, 2H), 1.85 (s, 6H), 2.05 (s, 6H), 2.60 (s, 3H), 2.67 (s, 3H), 4.62 (s, 2H), 7.23 (s, 2H), 7.50 (d, J=8.1 Hz, 2H), 7.99 (d, J=8.1 Hz, 2H), 8.30 (d, J=4.8 Hz, 1H), 8.43 (d, J=4.4 Hz, 1H), 8.60 (s, 1H), 8.76 (d, J=4.8 Hz, 1H); 8.80 (d, J=4.4 Hz, 1H), 8.84 (s, 1H), 9.03 (s, 1H); LD-MS obsd 626.8; FAB-MS obsd 626.2653, calcd 626.2045 (C$_{38}$H$_{35}$N$_4$Br); λ$_{abs}$ 416, 647 nm.

13-Acetyl-17,18-dihydro-10-mesityl-18,18-dimethyl-5-p-tolylporphyrin (8). Following a procedure for Stille coupling on aromatic compounds (Kosugi, M. et al., *Bull. Chem. Soc. Jpn.* 1987, 60, 767-768), a mixture of 6 (75 mg, 0.12 mmol), 7 (80 µL, 0.24 mmol) and (PPh$_3$)$_2$PdCl$_2$ (9.0 mg, 0.013 mmol) was refluxed in THF (12 mL) for 20 h in a Schlenk line. The reaction mixture was treated with 10% aqueous HCl (4 mL) at room temperature for 2 h. CH$_2$Cl$_2$ was added and the organic layer was separated. The organic layer was washed with saturated aqueous NaHCO$_3$, water, and brine. The organic layer was dried (Na$_2$SO$_4$), concentrated and chromatographed [silica, CH$_2$Cl$_2$/hexanes (1:1)], affording a purple solid (50 mg, 71%): $^1$H NMR δ-0.98 (brs, 2H), 1.86 (s, 6H), 2.02 (s, 6H), 2.61 (s, 3H), 2.66 (s, 3H), 3.05 (s, 3H), 4.56 (s, 2H), 7.24 (s, 2H), 7.50 (d, J=7.8 Hz, 2H), 7.96 (d, J=7.8 Hz, 2H), 8.23 (d, J=4.4 Hz, 1H), 8.31 (d, J=4.4 Hz, 1H), 8.68 (d, J=4.4 Hz, 1H), 8.69 (s, 1H), 8.70 (d, J=4.4 Hz, 1H), 8.86 (s, 1H), 9.98 (s, 1H); LD-MS obsd 590.8; FAB-MS obsd 590.3052, calcd 590.3046 (C$_{40}$H$_{38}$N$_4$O); λ$_{abs}$ 422, 661 (logs ε=4.67) nm, λ$_{em}$ 668, 711, 714 nm (Φ$_f$=0.23).

Zn(II)-13-Acetyl-17,18-dihydro-10-mesityl-18,18-dimethyl-5-p-tolylporphyrin (Zn-8). A solution of 8 (20 mg, 0.034 mmol) in CHCl$_3$ (2.8 mL) was treated with a solution of Zn(OAc)$_2$.2H$_2$O (75 mg, 0.34 mmol) in methanol (0.7 mL). The reaction mixture was stirred at room temperature for 16 h. CH$_2$Cl$_2$ was added and the reaction mixture was washed with water and brine. The organic layer was dried (Na$_2$SO$_4$). The crude mixture was concentrated and chromatographed (silica, CH$_2$Cl$_2$), affording a green solid (18 mg, 81%): $^1$H NMR δ 1.84 (s, 6H), 1.98 (s, 6H), 2.58 (s, 3H), 2.64 (s, 3H), 2.87 (s, 3H), 4.46 (s, 2H), 7.20 (s, 2H), 7.46 (d, J=8.2 Hz, 2H), 7.89 (d, J=8.2 Hz, 2H), 8.16 (d, J=4.4 Hz, 1H), 8.24 (d, J=4.4 Hz, 1H), 8.44 (s, 1H), 8.57 (d, J=4.4 Hz, 1H), 8.58 (d, J=4.4 Hz, 1H), 8.81 (s, 1H), 9.64 (s, 1H); LD-MS obsd 654.5; FAB-MS obsd 652.2238, calcd 652.2181 (C$_{40}$H$_{36}$N$_4$OZn); λ$_{abs}$ 424, 635 (log s=4.75) nm, λ$_{em}$ 641, 670-720 nm (Φ$_f$=0.24).

Cu(II)-13-Acetyl-17,18-dihydro-10-mesityl-18,18-dimethyl-5-p-tolylporphyrin (Cu-8). A solution of 8 (19 mg, 0.032 mmol) in CHCl$_3$ (3.2 mL) was treated with a solution of Cu(OAc)$_2$.H$_2$O (65 mg, 0.32 mmol) in methanol (0.8 mL) at room temperature for 16 h. The reaction mixture was washed with water and brine. The organic layer was dried (Na$_2$SO$_4$), concentrated and chromatographed [silica, CH$_2$Cl$_2$/hexanes (1:1)], affording a purple solid (17 mg, 81%): LD-MS obsd 651.7; FAB-MS obsd 651.2235, calcd 651.2285 (C$_{40}$H$_{36}$N$_4$OCu); λ$_{abs}$ 420, 631 (log ε=4.69) nm.

15-Bromo-17,18-dihydro-10-mesityl-18,18-dimethyl-5-p-tolylporphyrin (9). Following a reported procedure (Taniguchi, M. et al., *J. Org. Chem.* 2005, 70, 275-285), a solution of 8 (18.0 mg, 0.030 mmol) in THF (15 mL) was treated with NBS (5.5 mg, 0.030 mmol) at room temperature for 2 h. CH$_2$Cl$_2$ was added. The mixture was washed with aqueous NaHCO$_3$. The organic layer was dried (Na$_2$SO$_4$), concentrated, and chromatographed [silica, CH$_2$Cl$_2$/hexanes (3:1)], affording a purple solid (15 mg, 73%): $^1$H NMR δ –0.68-0.78 (br, 1H), 0.98-1.02 (br, 1H), 1.86 (s, 6H), 2.04 (s, 6H), 2.60 (s, 3H), 2.66 (s, 3H), 3.06 (s, 3H), 4.55 (s, 2H), 7.21 (s, 2H), 7.51 (d, J=7.8 Hz, 2H), 7.96 (d, J=7.8 Hz, 2H), 8.26 (d, J=4.4 Hz, 1H), 8.34 (d, J=4.4 Hz, 1H), 8.45 (s, 1H), 8.70-8.76 (m, 3H); FAB-MS obsd 668.2145, calcd 668.2150 (C$_{40}$H$_{37}$BrN$_4$O); λ$_{abs}$ 414, 515, 546, 600, 652 nm.

18,18-Dimethyl-10-mesityl-13$^1$-oxo-5-p-tolylphorbine (10). Following a procedure for α-arylation of aliphatic ketones (Muratake, H.; Natsume, M. *Tetrahedron Lett.* 1997, 38, 7581-7582; Muratake, H. e al., *Tetrahedron* 2004, 60, 11783-11803), a solution of 8 (18 mg, 0.030 mmol) in THF (15 mL) was treated with NBS (5.5 mg, 0.030 mmol) at room temperature for 2 h. CH$_2$Cl$_2$ was added. The mixture was washed with aqueous NaHCO$_3$. The organic layer was dried (Na$_2$SO$_4$) and concentrated. The crude mixture was used in the next step. Thus, a mixture of the crude solid, Cs$_2$CO$_3$ (50 mg, 0.15 mmol), and (PPh$_3$)$_2$PdCl$_2$ (4.0 mg, 6.0 μmol) was refluxed in toluene (2 mL) for 20 h in a Schlenk line. CH$_2$Cl$_2$ was added. The reaction mixture was washed with water and brine. The organic layer was dried (Na$_2$SO$_4$), concentrated and chromatographed [silica, CH$_2$Cl$_2$/hexanes (3:1)], affording a purple solid (8.0 mg, 44%): $^1$H NMR δ-1.25 (brs, 2H), 1.88 (s, 6H), 2.02 (s, 6H), 2.57 (s, 3H), 2.65 (s, 3H), 4.27 (s, 2H), 5.12 (s, 2H), 7.20 (s, 2H), 7.49 (d, J=7.8 Hz, 2H), 7.93 (d, J=7.8 Hz, 2H), 8.22 (d, J=4.4 Hz, 1H), 8.28 (d, J=4.4 Hz, 1H), 8.53 (s, 1H), 8.58 (s, 1H), 8.62 (d, J=4.4 Hz; 1H), 8.70 (d, J=4.4 Hz, 1H); LD-MS obsd 588.3; FAB-MS obsd 588.2900, calcd 588.2889 (C$_{40}$H$_{36}$N$_4$O); λ$_{abs}$ 417, 430, 529, 561, 660 nm n.

Example 2

Synthesis of Chlorins Bearing Conjugative Substituents at the 3 and/or 13-Positions The fundamental chromophore of the chlorophylls is a chlorin, which differs from a porphyrin in having one pyrrole ring reduced at the β-positions. Reduction of a porphyrin to give the chlorin enhances the intensity of the long-wavelength absorption (Q$_y$) band. However, mere reduction does not account for the strong intensity or redshifted position of the long-wavelength transition exhibited by naturally occurring chlorophylls. Indeed, chlorophyll a exhibits a strong Q$_y$ band at 662 nm (ε$_{Qy}$=86,300 M$^{-1}$cm$^{-1}$), and chlorophyll b exhibits a Q$_y$ band at 642 nm (ε$_{Qy}$=56,100 M$^{-1}$cm$^{-1}$) (Strain, H. H.; Svec, W. A. in *The Chlorophylls*, Vernon, L. P.; Seely, G. R., Eds., Academic Press: New York, 1966, pp 21-66) (FIG. 3). By contrast, a benchmark compound that contains only the core magnesium chlorin chromophore exhibits a Q$_y$ band at 610 nm (ε$_{Qy}$=56,000 M$^{-1}$cm$^{-1}$) (Eisner, U.; Linstead, R. P. *J. Chem. Soc.* 1955, 3742-3749). Naturally occurring chlorins typically contain a full complement of substituents at the β-pyrrole positions about the perimeter of the macrocycle, including alkyl groups (2-, 8-, and 12-positions) and auxochromic groups (3-, 7-, and 13-positions). Chlorophyll a and b each bear a 3-vinyl group, an isocyclic ring spanning the 13-15 positions, and a 7-methyl or 7-formyl group, respectively (Scheer, H. In *Chlorophylls*; Scheer, H. Ed.; CRC Press, Inc.: Boca Raton, Fla., USA, 1991; pp 3-30). The isocyclic ring contains a 13$^1$-keto group, which is conjugated with the π-system of the macrocycle.

Studies to probe the effects of substituents on the spectral properties of chlorophylls have generally relied on the preparation of derivatives of the naturally occurring macrocycles. Such studies indicate that the 3-vinyl substituent redshifts the Q$_y$ transition by ~12-14 nm (versus that of a 3-ethyl group) (Boldt, N. J. et al., *J. Am. Chem. Soc.* 1987, 109, 2284-2298; Smith, K. M. et al., *J. Am. Chem. Soc.* 1985, 107, 4946-4954), and the annulated 13-keto substituent imparts a redshift of ~20-30 nm (Boldt, N. J. et al., *J. Am. Chem. Soc.* 1987, 109, 2284-2298; Tamiaki, H. et al., *Tetrahedron Lett.* 1997, 38, 267-270; Abraham, R. J. et al., *J. Chem. Soc. Perkin Trans.* 2 1993, 1047-1059). The 3-vinyl group does not appear to cause any change in the intensity of the transition, whereas the 13-keto substituent has a significant hyperchromic effect (Boldt, N. J. et al., *J. Am. Chem. Soc.* 1987, 109, 2284-2298). Thus, the presence of conjugative substituents is essential for realizing strong absorption in the far-red region with chlorin chromophores.

Over the past decade we have been developing rational routes for preparing chlorins, wherein each chlorin bears a geminal dimethyl group in the reduced, pyrroline ring to lock-in the chlorin (i.e., dihydroporphyrin) hydrogenation level. The ability to construct regiospecifically substituted chlorins from simple precursors should facilitate fundamental studies of the effects of substituents on spectral properties, thereby complementing studies that employ modification of naturally occurring tetrapyrrole macrocycles (Pavlov, V. Y.; Ponomarev, G. V. *Chemistry of Heterocyclic Compounds* 2004, 40, 393-425). The general synthetic route entails reaction of a 1-bromo-dipyrromethane-9-carbinol (Eastern half) and a 2,3-dihydro-1,3,3-trimethyldipyrrin or 2,3,4,5-tetrahydro-1,3,3-trimethyldipyrrin (Western half). Use of substituted analogues of the Eastern and Western halves provided access to chlorins bearing substituents at the 2, 5, 8, 10, 12, and 18-positions (Chart 3) (Strachan, J.-P. et al., *J. Org. Chem.* 2000, 65, 3160-3172; Taniguchi, M. et al., *J. Org. Chem.* 2001, 66, 7342-7354; Balasubramanian, T. et al., *J. Org. Chem.* 2000, 65, 7919-7929). Subsequent oxidation afforded the 17-oxochlorins (Taniguchi, M. et al., *J. Org. Chem.* 2002, 67, 7329-7342). Halogenation of the chlorin or oxochlorin at the 15- or 20-position followed by Pd-mediated coupling reactions enabled introduction of aryl or ethynyl substituents at these meso sites (Taniguchi, M. et al., *J. Org. Chem.* 2005, 70, 275-285). Thus, access has been in hand for all sites with the exception of positions 3, 7, and 13. It is ironic that these latter three sites are perhaps the most important for tuning the spectral properties of the chlorins.

Chart 3

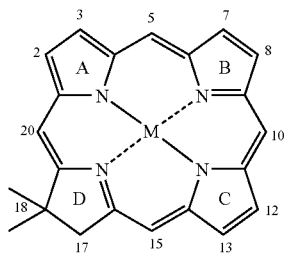

synthetic chlorin
and numbering system

In this paper, we report the synthesis of eight chlorins bearing a variety of groups at the 3- and/or 13-positions (Chart 4). The substituents of particular interest are potential auxochromic groups (vinyl, ethynyl, and acetyl). The chlorins bear a minimum of other substituents so that the effects of the 3- and 13-groups can be clearly delineated. The synthetic work reported herein exploits a new route to chlorins (Laha, J. K. et al., *J. Org. Chem.* 2006, 71, 4092-4102), which entails reaction of a 1-formyl-9-bromodipyrromethane (Eastern half) and a 2,3,4,5-tetrahydro-1,3,3-trimethyldipyrrin (Western half). Taken together, this work provides the foundation for tuning the spectral properties of chlorins in a systematic manner, and provides access to chlorins of potential value in applications ranging from artificial photosynthesis to photomedicine.

CHART 4

| | $R^3$ | $R^{13}$ |
|---|---|---|
| ZnC-V$^3$M$^{10}$ | vinyl | H |
| ZnC-E$^3$M$^{10}$ | ≡—TIPS | H |
| ZnC-M$^{10}$A$^{13}$ | H | COCH$_3$ |
| ZnC-M$^{10}$E$^{13}$ | H | ≡—TIPS |
| ZnC-E$^3$M$^{10}$E$^{13}$ | ≡—TIPS | ≡—TIPS |
| ZnC-E$^3$M$^{10}$A$^{13}$ | ≡—TIPS | COCH$_3$ |

| | $R^3$ | $R^{13}$ |
|---|---|---|
| ZnC-E$^3$E$^{13}$ | ≡—TIPS | ≡—TIPS |
| ZnC-E$^3$A$^{13}$ | ≡—TIPS | COCH$_3$ |

Results and Discussion

I. Synthesis. Our prior synthetic routes to chlorins employed a 1-bromodipyrromethane-9-carbinol as the Eastern half, where the substituent at the 9-position of the Eastern half became the 5-substituent in the chlorin. The reactivity of the Eastern half mandated the presence of an aryl group at the carbinol position; hence, all chlorins prepared in this manner incorporated a 5-aryl substituent. The methodology for chlorin synthesis in the companion paper entails reaction of a 1-formyl-9-bromodipyrromethane (Eastern half) and a 2,3,4,5-tetrahydro-1,3,3-trimethyldipyrrin (Western half), whereupon the chlorin lacks a 5-substituent. Our general strategy was to exploit this approach to chlorins, using an 8-bromo derivative of the Eastern half (i.e., an 8,9-dibromo-1-formyldipyrromethane) and an 8-bromo derivative of the Western half to gain access to chlorins bearing substituents at the 3- and/or 13-positions.

A. Eastern and Western Halves. The syntheses of 8,9-dibromo derivatives of 1-formyldipyrromethanes are shown in Scheme 4. While the 9-bromo derivatives of 1-formyldipyrromethanes are known (Laha, J. K. et al., *J. Org. Chem.* 2006, 71, 4092-4102), 8,9-dibromo derivatives of 1-formyldipyrromethanes have not been previously prepared. In this regard, a number of polyhalogenated pyrroles from marine organisms have been identified and synthesized (Bailey, D. M.; Johnson, R. E. *J. Med. Chem.* 1973, 16, 1300-1302; Bailey, D. M. et al., *J. Med. Chem.* 1973, 16, 1298-1300; Gilow, H. M.; Burton, D. E. *J. Org. Chem.* 1981, 46, 2221-2225; Keifer, P. A. et al., *J. Org. Chem.* 1991, 56, 2965-2975; Matsuki, S. et al., *J. Heterocyclic Chem.* 1997, 34, 87-91; Olofson, A. et al., *J. Org. Chem.* 1998, 63, 1248-2225; He, R. H.-Y.; Jiang, X.-K. *J. Chem. Research (S)* 1998, 786-787; Armitt, D. J. et al., *J. Chem. Soc., Perkin Trans.* 1, 2002, 1743-1745; Hoffmann, H.; Lindel, T. *Synthesis* 2003, 1753-1783; Patel, J. et al., *J. Org. Chem.* 2005, 70, 9081-9084). Treatment of 1-formyldipyrromethane 12 or 13 (Ptaszek, M. et al., *J. Org. Chem.* 2006, 71, 4328-4331) with 2 molar equivalents of NBS at −78° C. gave the 8,9-dibromo derivative 14 or 16 in 56% or 51% yield, respectively. The regiochemistry of the 8,9-vicinal substitution pattern in the dibromo derivatives was established by $^1$H-$^1$H 2D-COSY and 1D-NOE experiments. The regioselective formation of the dibromo-product (14, 16) can be explained by the fact that the α-acyl-substituted pyrrole ring is deactivated. Therefore, the first bromination occurs at the α-position of the adjacent pyrrole ring, and the second bromination occurs at the vicinal β-pyrrole position.

Scheme 4

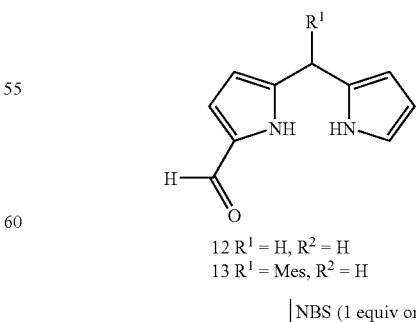

12 R$^1$ = H, R$^2$ = H
13 R$^1$ = Mes, R$^2$ = H

NBS (1 equiv or 2 equiv)
THF, -78° C., 1 h

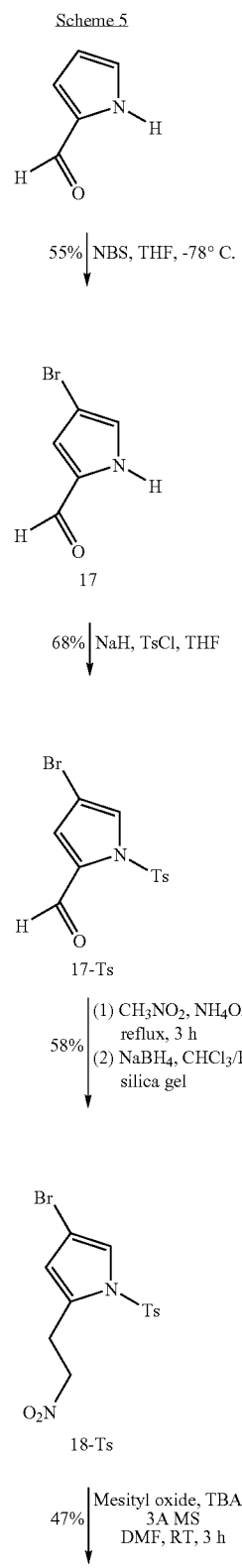

| | R¹ | R² | X | Y | Yield |
|---|---|---|---|---|---|
| 14 | H | H | Br | Br | 56% |
| 15 | Mes | H | Br | H | 67% |
| 16 | Mes | H | Br | Br | 51% |

The synthesis of an 8-bromo-substituted Western half is shown in Scheme 5. Treatment of pyrrole-2-carobxaldehyde with one molar equivalent of NBS at −78° C. gave 4-bromopyrrole-2-carboxaldehyde 17 (Anderson, J. H.; Lee, S.-F. Can. J. Chem. 1965, 43, 409-414) in 55% yield after crystallization. This method of bromination of pyrrole-2-carboxaldehyde is superior to a reported method that uses Br₂ (Anderson, J. H.; Lee, S.-F. Can. J. Chem. 1965, 43, 409-414). It should be mentioned here that careful handing of the crude product is required: the off-white solid often turns reddish (irrespective of preparation using Br₂ or NBS), which complicates crystallization. Following a procedure for the synthesis of 2-(2-nitroethyl)pyrroles (Taniguchi, M. et al., J. Org. Chem. 2001, 66, 7342-7354), treatment of 17 with excess nitromethane, sodium acetate and methylamine hydrochloride at room temperature for 16 h followed by reduction of the reaction mixture with NaBH₄ gave 4-bromo-2-(2-nitroethyl)pyrrole (18) in variable yields (32-48%). However, 18 was found to explode (CAUTION), which caused us to avoid handling this compound. Thus, we considered protection of the pyrrole nitrogen in 4-bromo-pyrrole-2-carboxaldehyde (17) for two purposes: (1) to render 4-bromo-2-(2-nitroethyl)pyrrole (18) as a stable compound, and (2) for efficient palladium-coupling in the latter part of the 8-ethynyl Western half synthesis. Considering the facile conditions for removal of a p-toluenesulfonyl group coupled with the crystalline nature of 2-(2-nitroethyl)-N-p-tosylpyrroles, N-tosylation (Tietze, L. F. et al., Synthesis 1996, 851-857) of compound 17 was carried out. Thus, treatment of 17 with NaH at 0° C. for 1 h followed by quenching with p-toluenesulfonyl chloride gave 17-Ts as a pale yellow crystalline solid in 68% yield. Following a reported procedure for the synthesis of 2-(2-nitrovinyl)-N-p-tosylpyrroles (Hamdan, A.; Wasley, J. W. F. Synth. Commun. 1985, 15, 71-74), a mixture of 17-Ts, excess nitromethane and ammonium acetate was refluxed for 3 h. The crude product was satisfactorily pure as evidenced by NMR spectroscopy and was directly used in the next step. NaBH₄ reduction of the crude product in the presence of Montmorillonite K10 (Bahulayan, D. et al., J. Org. Chem. 2003, 68, 5735-5738), or silica gel (Ptaszek, M. et al., Org. Process Res. Dev. 2005, 9, 651-659) at room temperature afforded 2-(2-nitroethyl)-N-p-tosylpyrrole 18-Ts as a white solid in 40% or 58% yield, respectively. Michael addition of 18-Ts with mesityl oxide in the presence of TBAF (Battersby, A. R. et al., J. Chem. Soc., Perkin Trans. 1 1984, 2725-2732) and 3 Å molecular sieves gave the detosylated pyrrole-hexanone 19 in 47% yield. The p-toluenesulfonyl group is known to be cleaved by TBAF (Yasuhara, A.; Sakamoto, T. Tetrahedron Lett. 1998, 39, 595-596). Reduction (Ptaszek, M. et al., Org. Process Res. Dev. 2005, 9, 651-659) of 19 with excess zinc dust and HCOONH₄ in THF at room temperature gave the 8-bromo Western half 20 in 45% yield.

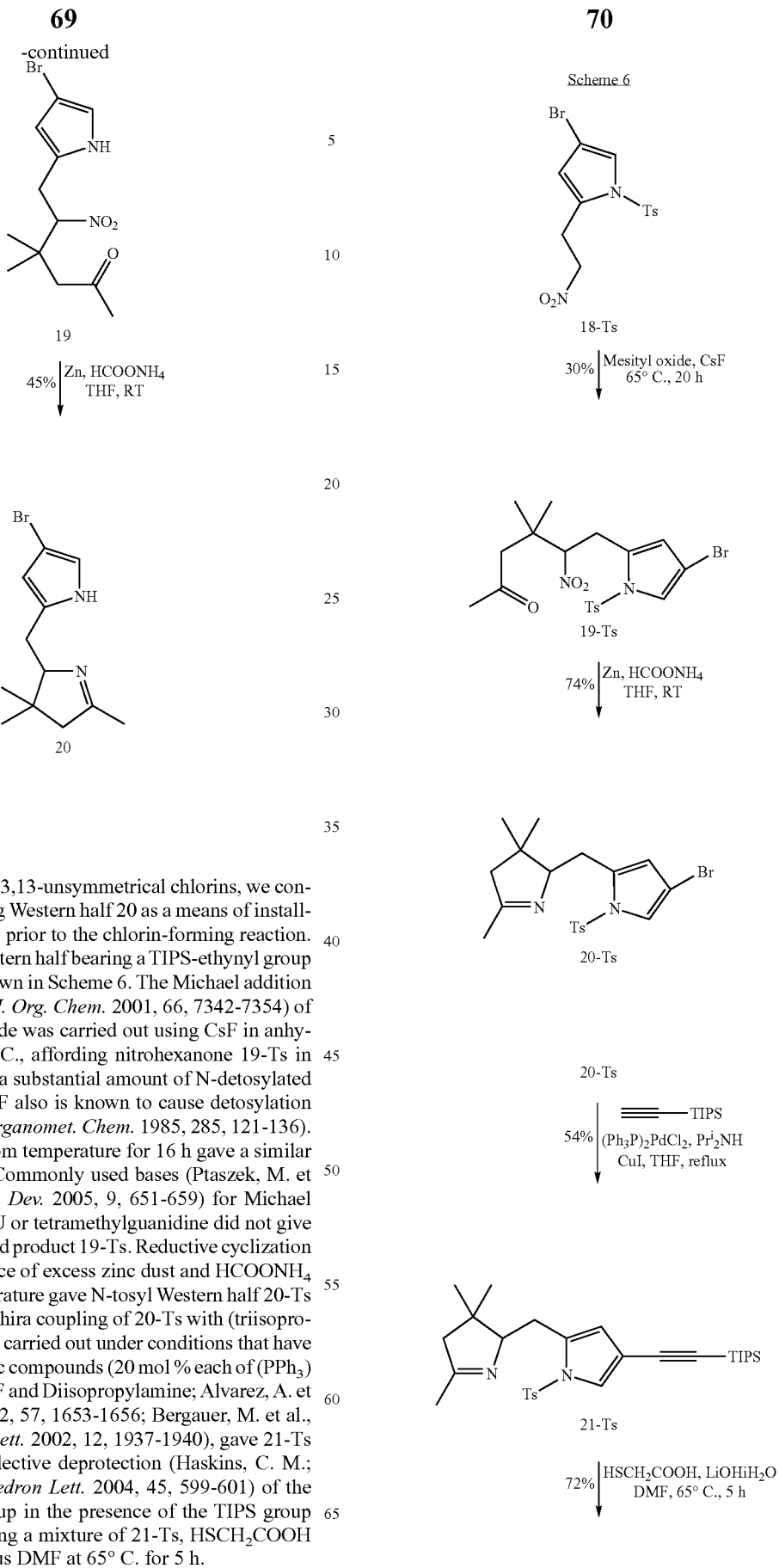

For the synthesis of 3,13-unsymmetrical chlorins, we considered functionalizing Western half 20 as a means of installing the required group prior to the chlorin-forming reaction. The synthesis of a Western half bearing a TIPS-ethynyl group at the 8-position is shown in Scheme 6. The Michael addition (Taniguchi, M. et al., *J. Org. Chem.* 2001, 66, 7342-7354) of 18-Ts and mesityl oxide was carried out using CsF in anhydrous $CH_3CN$ at 65° C., affording nitrohexanone 19-Ts in 30% yield along with a substantial amount of N-detosylated product 19 (30%). CsF also is known to cause detosylation (Eisch, J. J. et al., *J. Organomet. Chem.* 1985, 285, 121-136). Similar reaction at room temperature for 16 h gave a similar product distribution. Commonly used bases (Ptaszek, M. et al., *Org. Process Res. Dev.* 2005, 9, 651-659) for Michael additions such as DBU or tetramethylguanidine did not give any trace of the required product 19-Ts. Reductive cyclization of 19-Ts in the presence of excess zinc dust and $HCOONH_4$ in THF at room temperature gave N-tosyl Western half 20-Ts in 74% yield. Sonogashira coupling of 20-Ts with (triisopropylsilyl)acetylene was carried out under conditions that have been used with pyrrolic compounds (20 mol % each of $(PPh_3)_2PdCl_2$ and CuI in THF and Diisopropylamine; Alvarez, A. et al., *J. Org. Chem.* 1992, 57, 1653-1656; Bergauer, M. et al., *Bioorg. Med. Chem. Lett.* 2002, 12, 1937-1940), gave 21-Ts in 54% yield. The selective deprotection (Haskins, C. M.; Knight, D. W. *Tetrahedron Lett.* 2004, 45, 599-601) of the p-toluenesulfonyl group in the presence of the TIPS group was achieved by stirring a mixture of 21-Ts, $HSCH_2COOH$ and LiOH in anhydrous DMF at 65° C. for 5 h.

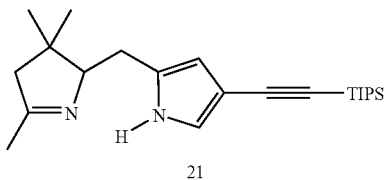

21

B. Chlorin Formation. The general chlorin-forming reaction entails p-TsOH.H$_2$O-catalyzed condensation of a 9-bromo-1-formyldipyrromethane species (Eastern half) and a 2,3,4,5-tetrahydro-1,3,3-trimethyldihydrodipyrrin species (Western half) followed by zinc-mediated oxidative cyclization as shown in eqn 1. Thus, a stirred suspension of an Eastern half (14-16, in slight excess) and a Western half with a substituent at the 8-position (20, 21) or no substituent (5) in anhydrous CH$_2$Cl$_2$ was treated with a solution of p-TsOH.H$_2$O in anhydrous MeOH under argon, affording a clear reddish-brown solution over 30-45 min. Workup afforded a yellow-brown foam-like solid, which was treated with Zn(OAc)$_2$, 2,2,6,6-tetramethylpiperidine (TMP) and AgOTf in CH$_3$CN at reflux exposed to air for 18-24 h. The chlorin was obtained by silica column chromatography. This route provided access to chlorins bearing H, Br, or TIPS-ethynyl at the 3-position, and H or Br at the 13-position, in yields ranging from 7 to 37% (Table 2).

product was the desired chlorin, and the minor chlorin was not identified. Each chlorin was characterized by absorption spectroscopy, $^1$H NMR spectroscopy, LD-MS, and FAB-MS analyses eqn 1

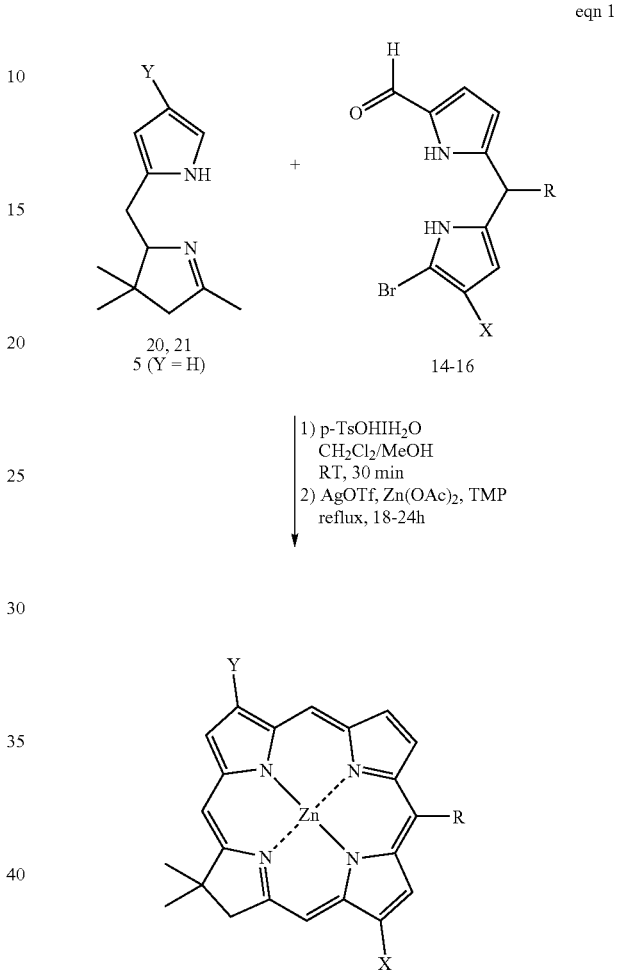

TABLE 2

Effects of Substituents on Chlorin-Forming Reactions.

| Entry | WH[a] | EH[b] | Chlorin substituents[c] | | | Chlorin | Yield %[d] |
|---|---|---|---|---|---|---|---|
| | | | 3 | 13 | 10 | | |
| 1 | 20 | 15 | Br | H | Mes | ZnC—Br$^3$M$^{10}$ | 37 |
| 2 | 5 | 16 | H | Br | Mes | ZnC-M$^{10}$Br$^{13}$ | 26 |
| 3 | 20 | 14 | Br | Br | H | ZnC—Br$^3$Br$^{13}$ | 26 |
| 4 | 20 | 16 | Br | Br | Mes | ZnC—Br$^3$M$^{10}$Br$^{13}$ | 30 |
| 5 | 21 | 14 | ≡—TIPS | Br | H | ZnC-E$^3$Br$^{13}$ | 7 |
| 6 | 21 | 16 | ≡—TIPS | Br | Mes | ZnC-E$^3$M$^{10}$Br$^{13}$ | 11 |

[a]Western half with no substituent (5) or a substituent at the 8-position.
[b]Eastern half.
[c]Numbering of chlorins is shown in Chart 1.
[d]Isolated yield.

In the 3-, 13- or 3,13-dibromochlorin-forming reactions, only one chlorin was isolated. In the 3,13-unsymmetrically substituted chlorin-forming reactions, two chlorins in ~2:1 ratio were isolated from the crude mixture, of which the major (C) Chlorin Derivatization. (i) 3-Substituted Chlorins. The syntheses of 3-vinylchlorin ZnC-V$^3$M$^{10}$ and 3-ethynylchlorin ZnC-E$^3$M$^{10}$ are shown in Scheme 7. Stille coupling of ZnC—Br$^3$M$^{10}$ and tributyl(vinyl)tin was carried out under conditions that have been employed with porphyrin substrates (10 mol % of (PPh$_3$)$_2$PdCl$_2$ in THF at reflux) (DiMagno, S. G. et al., J. Org. Chem. 1993, 58, 5983-5993), afforded 3-vinylchlorin ZnC-V$^3$M$^{10}$ in 66% yield. Sonogashira coupling of ZnC—Br$^3$M$^{10}$ and (triisopropylsilyl)acetylene was carried out under conditions that have been used with chlorins [Pd$_2$(dba)$_3$ and P(o-tol)$_3$ in toluene/TEA (5:1); Taniguchi, M. et al., J. Org. Chem. 2005, 70, 275-285] gave 3-ethynylchlorin ZnC-E$^3$M$^{10}$ in 52% yield. The latter conditions for Sonogashira coupling proceed under mild conditions and avoid the use of copper altogether, which can transmetalate with the zinc chelate.

Scheme 7

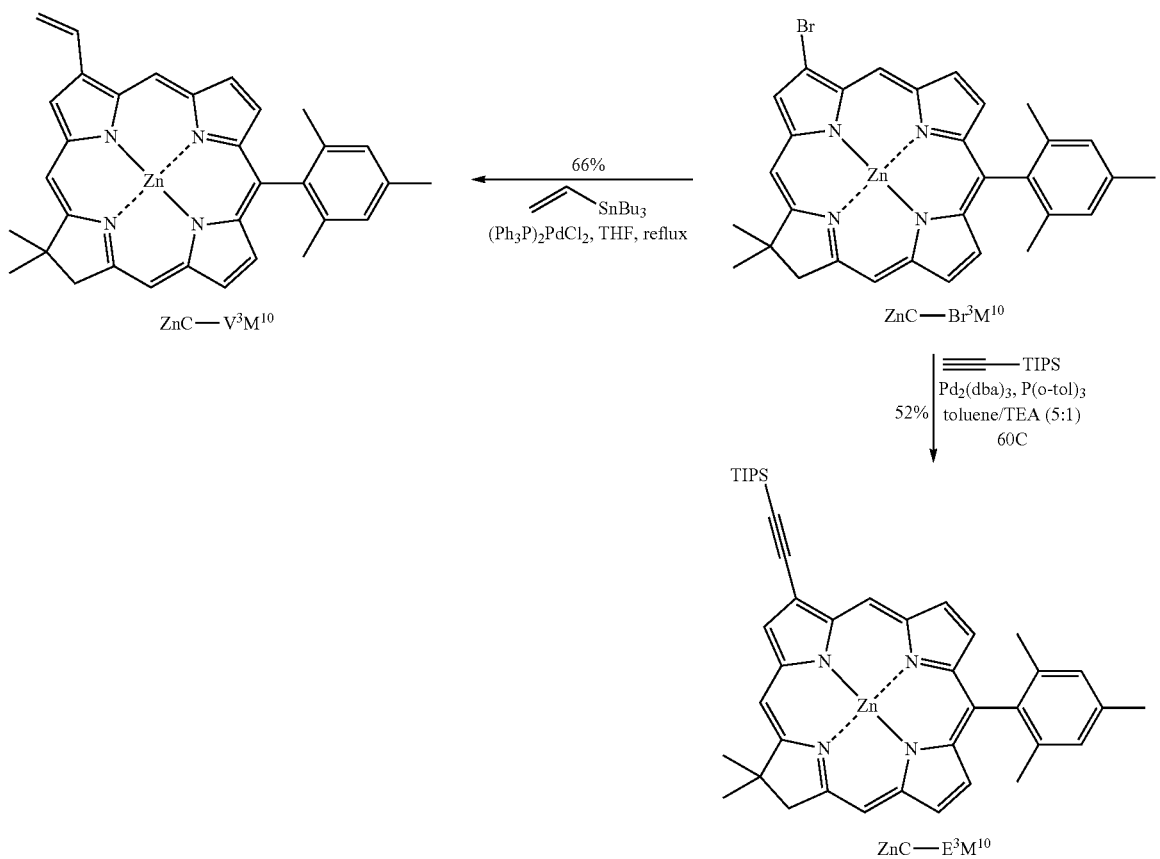

(ii) 13-Substituted Chlorins. The syntheses of 13-acetyl-chlorin ZnC-$M^{10}A^{13}$ and 13-ethynylchlorin ZnC-$M^{10}E^{13}$ are shown in Scheme 8. Chlorin ZnC-$M^{10}Br^{13}$ was demetalated with TFA in $CH_2Cl_2$ at room temperature. The crude free base chlorin was subjected to Stille coupling with tributyl(1-ethoxyvinyl)tin (Kosugi, M. et al., *Bull. Chem. Soc. Jpn.* 1987, 60, 767-768) in the presence of 20 mol % of Pd $(PPh_3)_2Cl_2$ in THF for 20 h. The hydrolysis of the reaction mixture with 10% aqueous HCl gave a crude product that on metalation with $Zn(OAc)_2\cdot 2H_2O$ gave chlorin ZnC-$M^{10}A^{13}$ in 53% overall yield. Sonogashira coupling of ZnC-$M^{10}Br^{13}$ with (triisopropylsilyl)acetylene in the presence of $Pd_2(dba)_3$ and $P(o\text{-tol})_3$ gave 13-ethynylchlorin ZnC-$M^{10}E^{13}$ in 71% yield.

Scheme 8

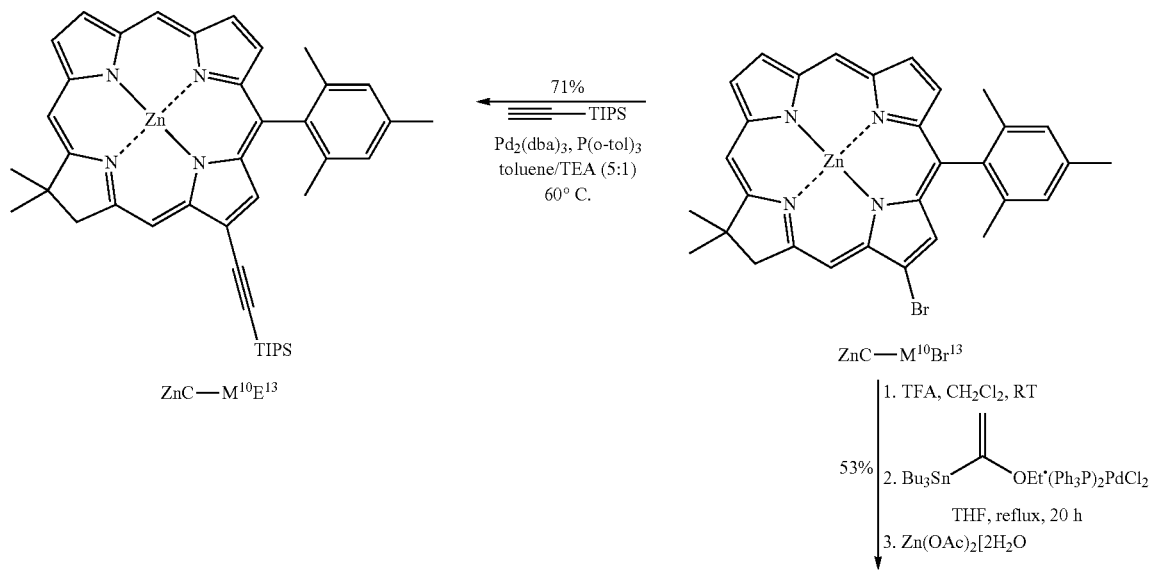

(iii) 3,13-Substituted Chlorins. The syntheses of 3,13-diethynylchlorins ZnC-E³E¹³ and ZnC-E³M¹⁰E¹³ are shown in Scheme 9. Sonogashira coupling of ZnC—Br³M¹⁰Br¹³ with (triisopropylsilyl)acetylene in the presence of 20 mol % of Pd(PPh₃)₂Cl₂ and CuI gave 3,13-diethynylchlorin ZnC-E³M¹⁰E¹³ in 42% yield along with the formation of a monoethynyl chlorin (15% yield) of unknown regiochemistry. The same coupling of ZnC—Br³Br¹³ or ZnC—Br³M¹⁰Br¹³ with (triisopropylsilyl)acetylene using the superior copper-free conditions (Pd₂(dba)₃ and P(o-tol)₃) gave 3,13-diethynylchlorin ZnC-E³E¹³ or ZnC-E³M¹⁰E¹³ in 53% or 75% yield, respectively:

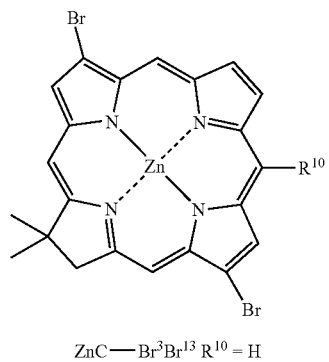

Scheme 9

ZnC—Br³Br¹³ R¹⁰ = H
ZnC—Br³M¹⁰Br¹³ R¹⁰ = Mes

≡—TIPS
Pd₂(dba)₃, P(o-tol)₃
toluene/TEA (5:1)
60 C.

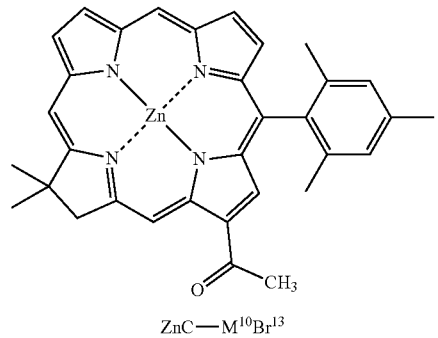

ZnC—M¹⁰Br¹³

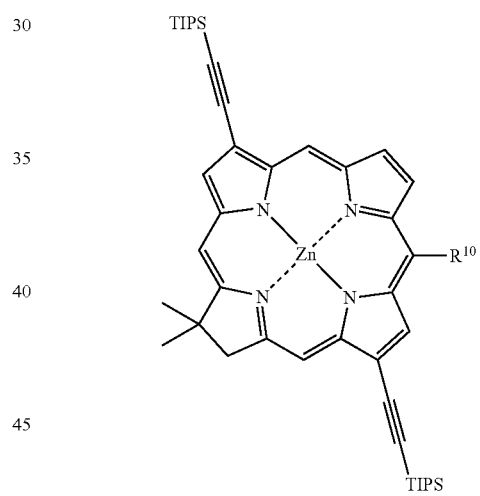

ZnC—E³E¹³ R¹⁰ = H, 53%
ZnC—E³M¹⁰E¹³ R¹⁰ = Mes, 75%

Following the protocol described above for the installation of the 13-acetyl group, the syntheses of 3-ethynyl-13-acetylchlorins ZnC-E³A¹³ and ZnC-E³M¹⁰A¹³ were carried out from their corresponding chlorins ZnC-E³Br¹³ and ZnC-E³M¹⁰Br¹³ as shown in Scheme 10. Thus, demetalation of ZnC-E³Br¹³ or ZnC-E³M¹⁰Br¹³, Stille coupling of the corresponding crude product with tributyl(1-ethoxyvinyl)tin, acidic workup, and zinc-metalation gave ZnC-E³A¹³ or ZnC-E³M¹⁰A¹³ in 53% or 23% overall yield, respectively.

Scheme 10

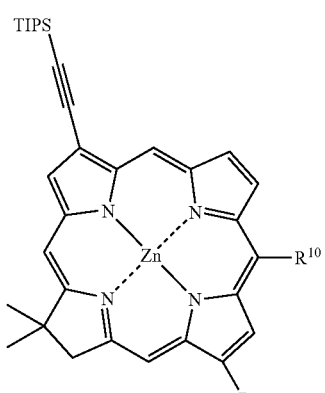

ZnC—Br³Br¹³ R¹⁰ = H
ZnC—E³—M¹⁰Br¹³ R¹⁰ = Mes

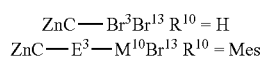

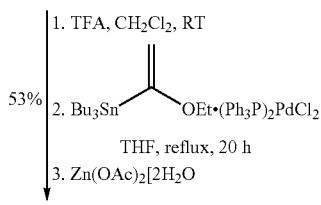

1. TFA, CH₂Cl₂, RT

53% 2. Bu₃Sn⎓OEt•(Ph₃P)₂PdCl₂
THF, reflux, 20 h
3. Zn(OAc)₂[2H₂O]

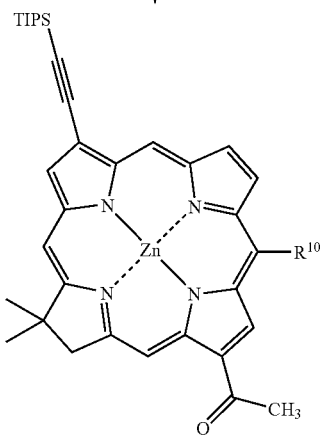

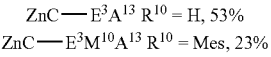

ZnC—E³A¹³ R¹⁰ = H, 53%
ZnC—E³M¹⁰A¹³ R¹⁰ = Mes, 23%

II. Spectroscopy. A. NMR Spectroscopy. $^1$H NMR spectroscopy provides valuable information about the substitution patterns on chlorins. In all 3- and/or 13-substituted chlorins described herein, the following features are observed: (1) the geminal dimethyl groups resonate as a singlet at δ~2.0 ppm; (2) the —CH₂ in the pyrroline ring gives rise to a singlet at δ~4.5 ppm; (3) two meso protons ($H^x$ and $H^y$ in the 10-mesityl substituted chlorin family) or three meso protons ($H^w$, $H^x$ and $H^y$ in the unsubstituted chlorin family) each appear as singlet in the region δ~8.5-8.9 ppm, whereas the remaining meso proton ($H^z$) appears as a singlet in the region δ~9.5-9.9 ppm; and (4) the two β-pyrrole protons ($H^7$, $H^8$) of the B ring each appear as a doublet (J=~4.1 Hz) at δ~8.3-8.9 ppm. In the mono-substituted (3- or 13-substituted) chlorin series, an additional pair of doublets (J=4.1-4.4 Hz) is observed for the two β-pyrrole protons of the remaining unsubstituted pyrrole ring, and the lone β-pyrrole proton in the mono-substituted (3- or 13-substituted) pyrrole ring resonates as a singlet in the region δ~8.2-9.1 ppm. In the 3,13-disubstituted chlorins, $H^2$ and $H^{12}$ each resonate as a singlet, and only one pair of doublets is observed. In the 13-acetylchlorins (ZnC-M¹⁰A¹³ and ZnC-E³M¹⁰A¹³), the vicinal β-pyrrole proton (112) resonates characteristically more downfield at δ9.4-9.6 ppm.

B. Absorption Spectroscopy. The spectral properties of interest in the chlorins include the position of the long-wavelength $Q_y$ transition, the intensity of the $Q_y$ transition, and the fluorescence quantum yield of the chlorin. The intensity of the $Q_y$ transition can be assessed by the measured molar absorption coefficient; however, comparisons of such values are somewhat unreliable given the experimental variability encountered upon handling small quantities of materials. A better comparison is achieved by examination of the ratio of the intensities of the B and $Q_y$ bands for a given compound (B/$Q_y$ ratio), which is determined simply by absorption spectroscopy without requiring determination of the molar absorption coefficient. For a wide variety of applications, bathochromic and hyperchromic shifts of the $Q_y$ band are desired (i.e., shifted to longer wavelength and increased in intensity).

The spectral properties of the zinc chlorins are listed in Table 3. The spectral properties can be compared with those of zinc analogues of chlorophyll a and b, (Jones, I. D. et al., *J. Agric. Food Chem.* 1968, 16, 80-83) as well as benchmark zinc chlorins lacking 3- and 13-substituents. The latter chlorins bear no substituent on the periphery of the macrocycle (ZnC) or a mesityl group at the 10-position (ZnC-M¹⁰) (structure block 1). Each parent chlorin exhibits a B band in the region 399-405 nm, a $Q_y$ band in the region 603-606 nm, and a B/$Q_y$ ratio in the range of 3.2-4.2.

The chlorins (in the 10-mesityl substituted family, FIG. 4) with a single substituent (such as vinyl, ethynyl or acetyl) at the 3- or 13-position each exhibit a B band in the region of 413-418 nm and a $Q_y$ band in the range from 621632 nm.

The 3,13-substituted chlorins (in the 10-mesityl substituted family) each exhibit a B band in the region of 423-428 nm whereas 3,13-substituted chlorins (in the 10-unsubstituted family, FIG. 5) each exhibit a B band in the region of 421-428 nm. The $Q_y$ band of each 3,13-substituted chlorin lies in the range from 621 to 655 nm.

TABLE 3

Absorption Properties of Chlorins[a]

| chlorins | $\lambda_{max}$ (nm), B | $\lambda_{max}$ (nm), $Q_y$ | $\Delta\nu_{Q_y}$ (cm$^{-1}$)[d] | B/$Q_y$ ratio |
|---|---|---|---|---|
| Zn-chlorophyll a[b] | 423 | 653 | NA | 1.4 |
| Zn-chlorophyll b[b] | 446 | 634 | NA | 2.9 |
| [c]ZnC-M¹⁰ | 405 | 606 | benchmark | 4.2 |
| ZnC—V³M¹⁰ | 413 | 621 | 400 | 3.3 |
| ZnC—E³M¹⁰ | 416 | 627 | 550 | 2.3 |
| ZnC—M¹⁰A¹³ | 418 | 632 | 680 | 2.2 |
| ZnC—M¹⁰E¹³ | 412 | 626 | 530 | 2.3 |
| ZnC-E³M¹⁰E¹³ | 10023 | 646 | 1020 | 1.6 |
| ZnC-E³M¹⁰A¹³ | 428 | 652 | 1160 | 1.5 |
| [c]ZnC | 399 | 603 | benchmark | 3.2 |
| ZnC-E³E¹³ | 421 | 645 | 1080 | 1.4 |
| ZnC-E³A¹³ | 428 | 655 | 1320 | 1.2 |

[a]In toluene at room temperature unless noted otherwise.
[b]Ref Jones, I. D. et al., J. Agric. Food Chem. 1968, 16, 80-83 (in diethyl ether).
[c]Ref Laha, J. K. et al., J. Org. Chem. 2006, 71, 4092-4102.
[d]The redshift caused by the substituent pattern for a given compound relative to that of the parent chlorin (ZnC or Zn—M¹⁰).

The magnitude of the shift is given in energy units in Table 2. A single ethynyl group, acetyl group, or bromine atom altered the B/$Q_y$ ratio to ~3.3-2.2 (from 4.2 in the unsubstituted parent compound). The largest effect of a single substituent was observed with the 13-acetyl group. The enhancement in relative intensity and shift in wavelength of the $Q_y$ band in 13-acetylchlorins is explained as follows. The 13-acetyl group can adopt a planar conformation and thus conjugate with the π-electrons of the macrocycle. In this regard, it has been shown that the acetyl group of 13-acetylporphyrins in an unhindered β-pyrrolic position can adopt a planar conformation and thus comes in conjugation with the π-electron of the macrocycle (Balaban, T. S. et al., *Eur. J. Org. Chem.* 2004, 3919-3930).

Structure block 1

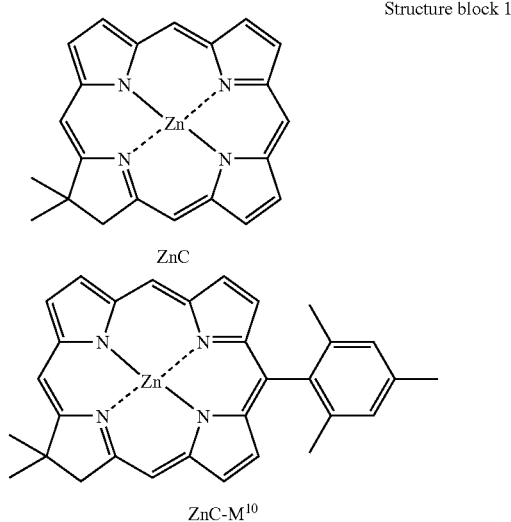

ZnC

ZnC-M[10]

In chlorins, the $Q_y$ band is polarized along the N—N axis containing two pyrrole rings (not intersecting the pyrroline ring). A chlorin nominally has $C_{2v}$ symmetry (Gouterman, M. In *The Porphyrins*; Dolphin, D., Ed.; Academic Press: New York, 1978; Vol. III, pp 1-165), in which case the 2- and 13-positions are symmetry equivalent, and the 3- and 12-positions are symmetry equivalent (Scheme 8). In practice, the presence of the geminal dimethyl group in the pyrroline ring of the synthetic chlorins prepared herein should have little effect on spectral properties. Although the 3- and 13-positions are not symmetry equivalent, each position resides in a pyrrole ring aligned along the $Q_y$ axis. In one case where a comparison could be made, the magnitude of the effect caused by a substituent at the 3-position was found to be quite similar to that at the 13-position: ZnC-E$^3$M$^{10}$ and ZnC-M$^{10}$E$^{13}$ exhibited nearly identical $Q_y$ band maxima (627 nm, 626 nm). Additional comparisons are required to more fully understand the effects of pyrrolic substituents at the two locations proximal (2 and 13) versus distal (3 and 12) to the pyrroline ring. Such comparisons are now possible with the synthetic methodology we have developed for preparing substituted chlorins.

Conclusions

Chlorins with different functional groups at 3- and 13-positions have been synthesized. In a zinc chlorin, the redshift of the $Q_y$ band caused by a 3-vinyl, 3-ethynyl, or 13-acetyl group is 15, 21, or 26 nm, respectively, from the benchmark at 606 nm. The redshift is comparable for the ethynyl group at the 3- or 13-position. The presence of an acetyl or ethynyl group at the 3- or 13-position also has a dramatic influence on the B/$Q_y$ band ratio. For example, the B/$Q_y$ band ratio (2.2) in chlorin ZnC-M$^{10}$A$^{13}$ is much lower than that (4.2) of a chlorin lacking a 13-acetyl group. The presence of two ethynyl groups at the 3- and 13-positions redshifts the $Q_y$ band by 40-42 nm and increases the relative intensity of the $Q_y$ band dramatically (the B/$Q_y$ band ratio is 1.4-1.6 versus 3.2-4.2 for that of the parent chlorins. Similarly, the presence of a 3-ethynyl group and a 13-acetyl group redshifts the $Q_y$ band by 46-52 nm and increases the relative intensity of the $Q_y$ band dramatically (the B/$Q_y$ band ratio is 1.2-1.5).

This work complements studies of derivatives of naturally occurring chlorins that contain more extensive conjugative groups (Tamiaki, H.; Kouroba, M. *Tetrahedron* 1997, 53, 10677-10688). Ethynes do not occur in the natural compounds; however, ethynes are particularly attractive in ease of introduction, extending the conjugation, and providing a synthetic handle for further elaboration. Ethynes have been employed to good effect in porphyrin chemistry (DiMagno, S. G. et al., *J. Org. Chem.* 1993, 58, 5983-5993; Lin, V. S.-Y. et al., *Science* 1994, 264, 1105-1111), but have been relatively little examined with hydroporphyrins (Taniguchi, M. et al., *J. Org. Chem.* 2005, 70, 275-285; Hindin, E. et al., *J. Phys. Chem. B* 2004, 108, 8190-8200). The synthetic approaches described herein should enable a much broader examination of the use of substituents to tune the spectra of chlorins.

Experimental Section

General. $^1$H NMR (400 MHz) and $^{13}$C NMR (75 MHz) spectra were collected at room temperature in CDCl$_3$ unless noted otherwise. Absorption spectra were obtained in toluene at room temperature. Chlorins were analyzed by laser desorption mass spectrometry (LD-MS) in the absence of a matrix. Metalation of free base chlorins was monitored by fluorescence spectroscopy. Melting points are uncorrected. All commercially available materials were used as received.

All the operations of chlorin forming reactions were performed on the same day starting from the preparation of 8,9-dibromo-1-formyldipyrromethanes. The condensation of Eastern half and Western half was carried out at room temperature under argon. The reaction mixture of the condensation reaction was quenched with ice-cold aqueous NaHCO$_3$. An ice-cold solution of the crude mixture in CH$_3$CN was treated with 2,2,6,6-tetramethylpiperidine followed by Zn(OAc)$_2$ and AgOTf. The reaction mixture was stirred at room temperature for 10-15 min before set it to gentle reflux.

All palladium-coupling reactions were performed using a Schlenk line. The Schlenk flask was attached, via thick-walled Tygon tubing, to a dual manifold. The flask containing all solid materials was evacuated via a vacuum pump for 3 min and after the evacuation period the flask was back-flushed with argon for 3 min. The process of evacuation and flushing was performed for a total of 3 times. At this time point the argon flow was turned up and the threaded stopcock was removed. Deaerated solvents were introduced by syringe. The threaded stopcock was replaced, and the argon flow rate was reduced. For Sonogashira couplings the flask was heated at 60-65° C., whereas for Stille couplings the reaction mixture was refluxed.

Noncommercial Compounds. Compounds 12, 13, and 15 were prepared following literature procedures (Ptaszek, M. et al., *J. Org. Chem.* 2006, 71, 4328-4331; Laha, J. K. et al., *J. Org. Chem.* 2006, 71, 4092-4102).

8,9-Dibromo-1-formyldipyrromethane (14). A solution of 12 (270 mg, 1.55 mmol) in dry THF (15.5 mL) at −78° C. under argon was treated with NBS (552 mg, 3.17 mmol). The reaction mixture was stirred for 1 h at −78° C. Hexanes and water were added at −20° C. and the mixture was allowed to warm to 0° C. The organic layer was separated, dried (K$_2$CO$_3$) and concentrated at ambient temperature. The resulting brown solid was purified by column chromatography [silica, hexanes/CH$_2$Cl$_2$/ethyl acetate (7:2:1)], affording a purple solid (290 mg, 56%): mp 109-111° C. (dec.); $^1$H NMR (THF-d$_8$) δ 3.93 (s, 2H), 5.89 (s, 1H), 6.05-6.07 (m, 1H), 6.78-6.79 (m, 1H), 9.37 (s, 1H), 10.81 (br s, 1H), 11.16 (br s, 1H); $^{13}$C NMR (THF-d$_8$) δ 26.0, 96.3, 98.0, 110.1, 112.7, 121.7, 128.9, 134.3, 139.0, 178.5; FAB-MS calcd 329.9003 (C$_{10}$H$_8$Br$_2$N$_2$O). Note: A significant amount (~30%) of the starting 1-formyldipyrromethane 12 was recovered in this reaction. Compound 14 in solution changes color from pale yellow to purple without any evidence of decomposition. The powdered solid 14 can be stored in the refrigerator for 2-3 weeks without decomposition.

8,9-Dibromo-1-formyl-5-mesityldipyrromethane (16). A solution of 13 (557 mg, 1.90 mmol) in dry THF (19 mL) at −78° C. under argon was treated with NBS (712 mg, 4.00 mmol). The reaction mixture was stirred for 1 h at −78° C. Hexanes and water were added at −20° C. and the mixture was allowed to warm to 0° C. The organic layer was separated, dried (K$_2$CO$_3$) and concentrated at ambient temperature. The resulting brown solid was purified by column chromatography [silica, hexanes/CH$_2$Cl$_2$/ethyl acetate (7:2:1)], affording a yellow solid (438 mg, 51%): mp 123-125° C. (dec.); $^1$H NMR (300 MHz, THF-d$_8$) δ 2.05 (s, 6H), 2.23 (s, 3H), 5.58-5.62 (m, 1H), 5.74 (s, 1H), 5.83-5.86 (m, 1H), 6.78-6.83 (m, 3H), 9.39 (s, 1H), 10.86 (br s, 1H), 11.16 (br s, 1H); $^{13}$C NMR (THF-d$_8$) δ 21.0, 21.1, 40.4, 98.3, 99.5, 111.3, 111.8, 131.1, 134.4, 134.5, 134.7, 137.4, 138.3, 141.9, 178.5; Anal. Calcd for C$_{19}$H$_{18}$Br$_2$N$_2$O: C, 50.69; H, 4.03; N, 6.22. Found: C, 50.70; H, 4.18; N, 6.03. Note: Careful handling of the solution of compound 16 is required. While it decomposes almost completely in solution (such as in ethyl acetate or chlorinated solvents) within 18-20 h even at 0° C., powdered solid 16 can be stored in the refrigerator for 5-7 days without decomposition. Evaporation of the solvent during workup or column chromatography should be done without heating. Compound 16 decomposed several times during NMR measurements (regardless of solvent such as CDCl$_3$ or THF-d$_8$) or attempted crystallization.

4-Bromopyrrole-2-carboxaldehyde (17). A solution of pyrrole-2-carboxaldehyde (4.75 g, 50.0 mmol) in dry THF (200 mL) was cooled to −78° C. under argon. NBS (8.90 g, 50.0 mmol) was added and the reaction mixture was stirred for 1 h at −78° C. Hexanes and water were added and the reaction mixture was allowed to warm to 0° C. The organic phase was extracted with hexanes and dried (Na$_2$SO$_4$). Crystallization of the crude mixture using hexanes/THF afforded white crystals (4.83 g, 55%): mp 120-121° C. [lit. 122-123° C. (Anderson, J. H.; Lee, S.-F. *Can. J. Chem.* 1965, 43, 409-414)]; $^1$H NMR δ 6.95 (m, 1H), 7.12 (m, 1H), 9.45 (s, 1H), 9.65-9.85 (br s, 1H); $^{13}$C NMR δ 99.0, 123.0, 127.0, 132.8, 179.3. Anal. Calcd for C$_5$H$_4$BrNO: C, 34.51; H, 2.32; N, 8.05; Found: C, 34.50; H, 2.26; N, 7.75. Note: Careful handling of the crude mixture is required. Evaporation of the solvent during, workup should be done without heating. The use of ethyl acetate or any chlorinated solvent was avoided during workup or crystallization. The crystallization of the crude mixture was carried out by dissolving the off-white solid in THF by warming (40-50° C.) followed by addition of hexanes. The crude off-white solid very often turns reddish color which subsequently prevents crystallization. In that case, a small silica-pad filtration of the crude mixture is required before crystallization.

4-Bromo-2-formyl-N-p-tosylpyrrole (17-Ts). Following a reported procedure (Tietze, L. F. et al., *Synthesis* 1996, 851-857), a stirred suspension of NaH (865 mg, 36.0 mmol) in THF (200 mL) was treated with 17 (5.22 g, 30.0 mmol) at room temperature. When the evolution of gas had ceased, the mixture was stirred for 1 h before treating with p-toluenesulfonyl chloride (6.30 g, 33.0 mmol). After 16 h, the conversion was complete as monitored by TLC. The reaction mixture was quenched by adding aqueous NH$_4$Cl. Ethyl acetate was added and the organic layer was separated. The organic layer was washed with water, brine and dried (Na$_2$SO$_4$). Concentration followed by crystallization (ethyl acetate/hexanes) afforded pale yellow crystals (6.75 g, 68%): mp 83-85° C.; $^1$H NMR δ 2.43 (s, 3H), 7.09 (d, J=2.0 Hz, 1H), 7.35 (d, J=8.3 Hz, 2H), 7.57 (d, J=2.0 Hz, 1H), 7.81 (d, J=8.3 Hz, 2H), 9.94 (s, 1H); $^{13}$C NMR δ 22.0, 101.8, 125.4, 127.8, 127.9, 130.6, 133.5, 134.7, 146.7, 178.5. Anal. Calcd or C$_{12}$H$_{10}$BrNO$_3$S: C, 43.92; H, 3.07; N, 4.27; S, 9.77. Found: C, 43.92; H, 3.02; N, 4.26; S, 9.84.

4-Bromo-2-(2-nitroethyl)-N-p-tosylpyrrole (18-Ts). Following a reported procedure (Kosugi, M.; Sumiya, T. et al., *Bull. Chem. Soc. Jpn.* 1987, 60, 767-768), a mixture of 17-Ts (1.64 g, 5.00 mmol), nitromethane (5.00 mL, 92-4 mmol) and ammonium acetate (270 mg, 3.50 mmol) was refluxed for 3 h. The reaction mixture was concentrated under reduced pressure. The residue was dissolved in ethyl acetate and the solution was washed (aqueous NaHCO$_3$, water and brine) and then dried (Na$_2$SO$_4$). Removal of the solvent gave a brown solid that was used directly in the next step. A stirred suspension of the crude product and Montmorillonite K10 in THF/methanol (3:2, 50 mL) was treated portionwise with NaBH$_4$ (284 mg, 7.50 mmol) at 0° C. The reaction mixture was stirred at room temperature for 1 h. Ethyl acetate was added and the reaction mixture was quenched by addition of saturated aqueous NH$_4$Cl. The organic layer was washed with water, dried (Na$_2$SO$_4$), and concentrated. The residue was chromatographed [silica, hexanes/CH$_2$Cl$_2$/ethyl acetate (8:1:1)] to give a white solid (760 mg, 40%): mp 125-127° C.; $^1$H NMR δ 2.44 (s, 3H), 3.81 (t, J=7.0 Hz, 2H), 4.60 (t, J=7.0 Hz, 2H), 6.09 (d, J=2.0 Hz, 1H), 7.31 (d, J=2.0 Hz, 1H), 7.35 (d, J=8.3 Hz, 2H), 7.68 (d, J=8.3 Hz, 2H); $^{13}$C NMR δ 21.9, 25.3, 74.3, 100.9, 117.3, 122.5, 127.0, 129.5, 130.7, 135.4, 146.2. Anal. Calcd for C$_{13}$H$_{13}$BrN$_2$O$_4$S: C, 41.84; H, 3.51; N, 7.51; S, 8.59. Found: C, 41.99; H, 3.43; N, 7.33; S, 8.80.

Alternative procedure: Following a reported procedure (Kosugi, M. et al., *Bull. Chem. Soc. Jpn.* 1987, 60, 767-768), a mixture of 17-Ts (7.50 g, 22.8 mmol), nitromethane (21.6 mL, 405 mmol) and ammonium acetate (1.18 g, 15.3 mmol) was refluxed for 3 h. The reaction mixture was concentrated under reduced pressure. The residue was dissolved in ethyl acetate and the solution was washed with aqueous NaHCO$_3$, water and brine and then dried (Na$_2$SO$_4$). Removal of the solvent gave a brown solid that was used directly in the next step. Following a published procedure (Ptaszek, M. et al., *Org. Process Res. Dev.* 2005, 9, 651-659), a solution of the crude product in CHCl$_3$ (195 mL) and 2-propanol (65 mL) was treated with silica (26.3 g). The resulting suspension was treated in three portions with NaBH$_4$ (1.65 g, 45.6 mmol) under vigorous stirring at room temperature. The reaction mixture was stirred for ~1.5 h and monitored by TLC. The reaction mixture was filtered. The filter cake was washed several times with CH$_2$Cl$_2$. The organic solution was washed with water and brine. The organic layer was dried (NaSO$_4$), concentrated, and subjected to high vacuum to remove traces of 2-propanol. The resulting residue was subjected to column chromatography [silica, hexanes/CH$_2$Cl$_2$/ethyl acetate (8:1:1)] to afford a pale yellow solid (4.95 g, 58%): mp 126-128° C.; $^1$H NMR (300 MHz) δ 2.44 (s, 3H), 3.38 (t, J=7.0 Hz, 2H), 4.60 (t, J=7.0 Hz, 2H), 6.09 (d, J=2.0 Hz, 1H), 7.31 (d, J=2.0 Hz, 1H), 7.35 (d, J=8.3 Hz, 2H), 7.68 (d, J=8.3 Hz, 2H); $^{13}$C NMR δ 21.9, 25.3, 74.3, 100.9, 117.3, 122.5, 127.0, 129.5, 130.7, 135.4, 146.2. Anal. Calcd for $C_{13}H_{13}BrN_2O_4S$: C, 41.84; H, 3.51; N, 7.51; S, 8.59.

4,4-Dimethyl-5-nitro-6-(1H-pyrrol-2-yl)hexan-2-one (19). Following a procedure (Battersby, A. R. et al., *J. Chem. Soc., Perkin Trans.* 1 1984, 2725-2732), a solution of TBAF.$3H_2O$ (2.64 g, 8.36 mmol) in anhydrous DMF (25 mL) was stirred in the presence of 3 Å molecular sieves for 30 min at room temperature under argon. The stirred suspension was treated with a solution of 18-Ts (1.56 g, 4.18 mmol) and mesityl oxide (4.80 mL, 42.0 mmol) in anhydrous DMF (15 mL). The mixture was stirred at room temperature for 3 h. The reaction mixture was filtered through filter paper. The filtrate was concentrated under reduced pressure. The resulting residue was dissolved in ethyl acetate. The organic solution was washed with water, dried ($Na_2SO_4$), and chromatographed [silica, $CH_2Cl_2$] to give a viscous liquid (623 mg, 47%): $^1H$ NMR (300 MHz) δ 1.09 (s, 3H), 1.22 (s, 3H), 2.14 (s, 3H), 2.40 (d, J=17.6 Hz, 1H), 2.58 (d, J=17.6 Hz, 1H), 2.97 (AB, J=15.2 Hz, 1H), 3.28 (ABX, $^2J$=15.2 Hz, $^3J$=11.6 Hz, 1H), 5.11 (ABX, $^2J$=11.6 Hz, $^3J$=3.5 Hz, 1H), 5.97-5.99 (m, 1H), 6.62-6.64 (m, 1H), 8.10-8.18 (br s, 1H); $^{13}C$ NMR δ 24.3, 24.5, 26.8, 32.0, 36.9, 51.6, 94.4, 96.2, 110.0, 117.8, 127.3, 207.7; FAB-MS calcd 316.0423 ($C_{12}H_{17}BrN_2O_3$). Anal. Calcd for $C_{12}H_{17}BrN_2O_3$: C, 45.44; H, 5.40; N, 8.83. Found: C, 46.10; H, 5.30; N, 8.27. Note: Compound 19 (neat or in solution) changes color from yellow to black overtime (1-2 days) at room temperature indicating partial decomposition.

4,4-Dimethyl-5-nitro-6-(N-p-tosylpyrrol-2-yl)hexan-2-one (19-Ts). Following a literature procedure (Taniguchi, M. et al., *J. Org. Chem.* 2001, 66, 7342-7354), CsF (3.17 g, 20.9 mmol) was freshly dried by heating at 100° C. under vacuum for 1 h and then cooling to room temperature under argon. A solution of 18-Ts (2.60 g, 6.96 mmol) and mesityl oxide (8.16 mL, 71.0 mmol, 10 molar equiv) in dry acetonitrile (61 mL) was transferred by cannula to the flask containing CsF. The mixture was stirred at 65° C. for 18 h. The reaction mixture was filtered through a pad of silica and the filter cake was washed with ethyl acetate. The filtrate was concentrated under reduced pressure. Column chromatography [silica, hexanes/$CH_2Cl_2$/ethyl acetate (7:2:1)] of the crude product afforded a brown solid (0.980 g, 30%): mp 103-104° C.; $^1H$ NMR δ 1.11 (s, 3H), 1.24 (s, 3H), 2.13 (s, 3H), 2.40 (AB, J=17.8 Hz, 1H), 2.43 (s, 3H), 2.55 (AB, J=17.8 Hz, 1H), 3.18 (AB, J=16.2 Hz, 1H), 3.36 (ABX, $^3J$=16.2 Hz, $^2J$=11.8 Hz, 1H), 5.14 (AB, J=11.8 Hz, 1H), 6.00-6.02 (m, 1H), 7.22-7.24 (m, 1H), 7.34 (AB, J=8.2 Hz, 2H), 7.64 (AB, J=8.2 Hz, 2H); $^{13}C$ NMR δ 21.9, 23.7, 24.4, 26.4, 31.8, 36.9, 51.0, 93.5, 101.0, 117.0, 122.4, 126.8, 130.2, 130.6, 135.6, 146.0, 206.3; FAB-MS obsd 471.0596, calcd 471.0589 ($cl_9H_{23}BrN_2O_5$).

8-Bromo-2,3,4,5-tetrahydro-1,3,3-trimethyldipyrrin (20). Following a refined procedure (Ptaszek, M. et al., *Org. Process Res. Dev.* 2005, 9, 651-659), a stirred suspension of 19 (350 mg, 1.10 mmol) and $HCOONH_4$ (1.04 g, 16.5 mmol) in THF (4.4 mL) was treated portionwise with Zn dust (1.07 g, 16.5 mmol) for 15 min. The reaction mixture was stirred vigorously for 3 h at room temperature. Ethyl acetate was added and the reaction mixture was filtered through filter paper. The filtrate was washed (half saturated aqueous $NaHCO_3$, water, brine), dried ($Na_2SO_4$), and chromatographed (silica, ethyl acetate), affording a yellow solid (135 mg, 45%): mp 83-84° C.; $^1H$ NMR δ 0.92 (s, 3H), 1.11 (s, 3H), 2.03 (s, 3H), 2.28 (AB, J=16.8 Hz, 1H), 2.38 (AB, J=16.8 Hz, 1H), 2.54 (ABX, $^2J$=14.9 Hz, $^3J$=11.8 Hz, 1H), 2.69 (ABX, $^2J$=11.8 Hz, $^3J$=2.5 Hz, 1H), 3.56-3.62 (m, 1H), 5.85-5.94 (m, 1H), 6.63-6.69 (m, 1H), 9.72-10.01 (br s, 1H); $^{13}C$ NMR δ 20.7, 23.0, 27.3, 27.8, 42.0, 54.4, 80.2, 95.2, 108.2, 116.5, 132.8, 175.1. Anal. Calcd for $C_{12}H_{17}BrN_2$: C, 53.54; H, 6.37; N, 10.41. Found: C, 53.15; H, 6.32; N, 10.11. Note: Stirring the reaction for prolonged time may cause the formation of side product.

9-Bromo-2,3,4,5-tetrahydro-1,3,3-trimethyl-N-p-tosyl-dipyrrin (20-Ts). A stirred suspension of 19-Ts (640 mg, 1.36 mmol) and $HCOONH_4$ (1.72 g, 27.2 mmol) in THF (6.0 mL) was treated portionwise with Zn dust (1.78 g, 27.2 mmol) for 5 min. The reaction mixture was stirred vigorously for 4 h at room temperature. Ethyl acetate was added and the reaction mixture was filtered through filter paper. The filtrate was washed (half-saturated aqueous $NaHCO_3$, water, brine), dried ($Na_2SO_4$), and chromatographed [silica, hexanes/ethyl acetate (1:1)], affording a viscous liquid (0.425 g, 74%): $^1H$ NMR (300 MHz) δ 0.88 (s, 3H), 1.07 (s, 21H), 1.97 (s, 3H), 2.28 (AB, J=16.8 Hz, 1H), 2.36 (AB, J=16.8 Hz, 1H), 2.41 (s, 3H), 2.63 (ABX, $^2J$=16.1 Hz, $^3J$=10.2 Hz, 1H), 2.92 (ABX, $^2J$=16.1 Hz, $^3J$=3.8 Hz, 1H), 3.67-3.70 (m, 1H), 6.25-6.28 (m, 1H), 7.28-7.30 (m, 3H), 7.68 (AB, J=8.2 Hz, 2H); $^{13}C$ NMR δ 20.6, 21.8, 22.9, 27.0, 28.0, 42.4, 54.4, 77.8, 101.0, 116.1, 121.0, 127.2, 130.2, 135.0, 135.9, 145.4, 175.0. FAB-MS obsd 423.0768, calcd 423.0742 ($C_{19}H_{23}BrN_2O_2S$).

9-[2-(Triisopropylsilyl)ethynyl]-2,3,4,5-tetrahydro-1,3,3-trimethyldipyrrin 21). Following a reported procedure (Haskins, C. M.; Knight, D. W. *Tetrahedron Lett.* 2004, 45, 599-601), a stirred suspension of 21-Ts (230 mg, 0.438 mmol) and LiOH (53.0 mg, 2.20 mmol) in anhydrous DMF (2 mL) was treated with $HSCH_2COOH$ (77.0 µL, 1.10 mmol) at room temperature. The reaction mixture was stirred for 5 h at 65° C. under argon. Ethyl acetate was added and the resulting mixture was washed (water, brine), dried ($Na_2SO_4$), concentrated, and chromatographed [silica, hexanes/ethyl acetate (1:1)], affording a white solid (118 mg, 72%): mp 110-112° C.; $^1H$ NMR (300 MHz) δ 0.92 (s, 3H), 1.12 (s, 21H), 2.03 (s, 3H), 2.28 (AB, J=16.8 Hz, 1H), 2.37 (AB, J=16.8 Hz, 1H), 2.51 (ABX, $^2J$=14.9 Hz, $^3J$=11.8 Hz, 1H), 2.68 (ABX, $^2J$=14.9 Hz, $^3J$=2.8 Hz, 1H), 3.56-3.59 (m, 1H), 6.01-6.03 (m, 1H), 6.90-6.92 (m, 1H), 9.90-9.93 (br s, 1H); $^{13}C$ NMR δ 11.6, 18.9, 20.6, 23.0, 27.3, 27.7, 42.0, 54.4, 80.1, 87.2, 103.7, 104.0, 109.4, 121.9, 131.8, 175.6. Anal. Calcd for $C_{23}H_{38}N_2Si$: C, 74.53; H, 10.33; N, 7.56. Found: C, 74.25; H, 10.29; N, 7.49.

N-p-Tosyl-3-[2-(triisopropylsilyl)ethynyl]-2,3,4,5-tetrahydro-1,3,3-trimethyldipyrrin (21-Ts). A mixture of 20-Ts (0.560 g, 1.32 mmol), (triisopropylsilyl)acetylene (0.590 mL, 2.65 mmol), $(PPh_3)_2PdCl_2$ (186 mg, 0.265 mmol), diisopropylamine (0.930 mL, 6.63 mmol) and CuI (50.0 mg, 0.262 mmol) was refluxed in THF (6 mL) for 20 h in a Schlenk line. The reaction mixture was concentrated and chromatographed [silica, hexanes/ethyl acetate (1:1)] affording a viscous liquid (375 mg, 54%): $^1H$ NMR (300 MHz) δ 0.87 (s, 3H), 1.07 (s, 21H), 1.97 (s, 3H), 2.26 (AB, J=16.8 Hz, 1H), 2.35 (AB, J=16.8 Hz, 1H), 2.40 (s, 3H), 2.60 (ABX, $^2J$=16.2 Hz, $^3J$=10.1 Hz, 1H), 2.86 (ABX, $^2J$=16.2 Hz, $^3J$=3.8 Hz, 1H), 3.68-3.70 (m, 1H), 6.28-6.30 (m, 1H), 7.28 (d, J=8.1 Hz, 2H), 7.46-7.47 (m, 1H), 7.68 (d, J=8.1 Hz, 2H); $^{13}C$ NMR δ 11.5, 18.8, 20.7, 21.8, 23.0, 27.2, 28.0, 42.4, 54.6, 77.9, 91.1, 100.5, 108.6, 116.2, 125.9, 127.3, 130.3, 134.1, 136.0, 145.4, 175.2. FAB-MS obsd 525.2966 (M+H)$^+$, calcd 524.2893 ($C_{30}H_{44}N_2O_2SSi$).

Zn(II)-3-Bromo-17,18-dihydro-10-mesityl-18,18-dimethylporphyrin (ZnC—Br$^3$M$^{10}$). Following a standard procedure (Laha, J. K. et al., *J. Org. Chem.* 2006, 71, 4092-4102), a solution of 15 (75 mg, 0.20 mmol) and 20 (54 mg, 0.20 mmol) in distilled $CH_2Cl_2$ (6 mL) was treated with a solution of p-TsOH.$H_2O$ (0.19 g, 1.0 mmol) in distilled methanol (2 mL) under argon. The red reaction mixture was stirred at room temperature for 30 min. The reaction mixture was washed (10% NaHCO$_3$, water, brine), dried (Na$_2$SO$_4$), and concentrated, yielding a brown solid. The solid was dissolved in CH$_3$CN (20 mL) and subsequently treated with 2,2,6,6-tetramethylpiperidine (0.340 mL, 2.00 mmol), Zn(OAc)$_2$ (370 mg, 2.00 mmol) and AgOTf (154 mg, 0.600 mmol). The resulting suspension was refluxed for 14 h exposed to air. The crude mixture was concentrated and chromatographed [silica, CH$_2$Cl$_2$], affording a green solid (45 mg, 37%): $^1$H NMR δ 1.85 (s, 6H), 2.01 (s, 6H), 2.60 (s, 3H), 4.50 (s, 2H), 7.23 (s, 2H), 8.37 (d, J=4.1 Hz, 1H), 8.50 (s, 1H), 8.55 (d, J=4.4 Hz, 1H), 8.60 (d, J=4.4 Hz, 1H), 8.68 (s, 1H), 8.77 (s, 1H), 8.88 (d, J=4.1 Hz, 1H), 9.73 (s, 1H); LD-MS obsd 598.3; FAB-MS obsd 598.0750, calcd 598.0711 (C$_{31}$H$_{27}$BrN$_4$Zn); λ$_{abs}$ 408, 614 nm.

Zn (II)-13-Bromo-17,18-dihydro-10-mesityl-18,18-dimethylporphyrin (ZnC-M$^{10}$Br$^{13}$). Following a standard procedure (Laha, J. K. et al., *J. Org. Chem.* 2006, 71, 4092-4102), a solution of 16 (245 mg, 0.544 mmol) and 5 (86.4 mg, 0.452 mmol) in distilled CH$_2$Cl$_2$ (13 mL) was treated with a solution of p-TsOH.H$_2$O (0.430 g, 2.26 mmol) in distilled methanol (5 mL) under argon. The reaction mixture was stirred at room temperature for 30 min. Workup followed by concentration of the crude mixture afforded a yellow foam-like solid. The solid was dissolved in CH$_3$CN (45 mL) and subsequently treated with 2,2,6,6-tetramethylpiperidine (1.15 mL, 6.81 mmol), Zn(OAc)$_2$ (829 mg, 4.52 mmol) and AgOTf (348 mg, 1.35 mmol). The resulting suspension was refluxed for 18 h exposed to air. The crude mixture was concentrated and chromatographed [silica, hexanes/CH$_2$Cl$_2$ (2:1)], affording a purple solid (72 mg, 26%): $^1$H NMR δ 1.86 (s, 6H), 2.03 (s, 6H), 2.60 (s, 3H), 4.52 (s, 2H), 7.23 (s, 2H), 8.37 (d, J=4.4 Hz, 1H), 8.57 (s, 1H), 8.61 (s, 1H), 8.72 (d, J=3.5 Hz, 1H), 8.80 (d, J=3.5 Hz, 1H), 8.85 (s, 1H), 9.01 (d, J=4.4 Hz, 1H), 9.54 (s, 1H); LD-MS obsd 598.5 (M$^+$), 518.8 [(M-Br)$^+$]; FAB-MS obsd 598.0737, calcd 598.0711 (C$_{31}$H$_{27}$BrN$_4$Zn); λ$_{abs}$ 406, 613 nm.

Zn(II)-3,13-Dibromo-17,18-dihydro-18,18-dimethylporphyrin (ZnC—Br$^3$Br$^{13}$). Following a standard procedure (Laha, J. K. et al., *J. Org. Chem.* 2006, 71, 4092-4102), a solution of 14 (68.0 mg, 0.205 mmol) and 20 (56.0 mg, 0.205 mmol) in distilled CH$_2$Cl$_2$ (4 mL) was treated with a solution of p-TsOH.H$_2$O (195 mg, 1.03 mmol) in distilled methanol (1 mL) under argon. The red reaction mixture was stirred at room temperature for 50 min. The reaction mixture was washed (10% NaHCO$_3$, water, brine), dried (Na$_2$SO$_4$), and concentrated, which yielded a brown solid. The solid was dissolved in CH$_3$CN (20.5 mL) and subsequently treated with 2,2,6,6-tetramethylpiperidine (0.523 mL, 3.07 mmol), Zn(OAc)$_2$ (790 mg, 3.07 mmol), and AgOTf (113 mg, 0.615 mmol). The resulting suspension was refluxed for 19 h exposed to air. The crude mixture was concentrated and chromatographed [silica, CH$_2$Cl$_2$/hexanes, (2:1)], affording a green solid (30.0 mg, 26%): $^1$H NMR (THF-d$_8$) δ 2.03 (s, 6H), 4.57 (s, 2H), 8.65 (s, 1H), 8.67 (s, 1H), 8.82 (s, 1H), 8.87 (s, 1H), 9.03 (s, 2H), 9.73 (s, 1H), 9.75 (s, 1H); LD-MS obsd 562.8; FAB-MS obsd 557.9050, calcd 557.9033 (C$_{22}$H$_{16}$Br$_2$N$_4$Zn); λ$_{abs}$ 405, 620 nm.

Zn(II)-3,13-Dibromo-17,18-dihydro-10-mesityl-18,18-dimethylporphyrin (ZnC—Br$^3$M$^{10}$Br$^{13}$). A stirred suspension of 16 (360 mg, 0.800 mmol) and 20 (108 mg, 0.400 mmol) in distilled CH$_2$Cl$_2$ (10 mL) was treated with a solution of p-TsOH.H$_2$O (380 mg, 2.00 mmol) in distilled methanol (6 mL) under argon. The reaction mixture was stirred at room temperature for 30 min. Workup followed by concentration of the crude mixture afforded a brown solid. The solid was dissolved in CH$_3$CN (40 mL) and subsequently treated with 2,2,6,6-tetramethylpiperidine (1.00 mL, 6.00 mmol), Zn(OAc)$_2$ (734 mg, 4.00 mmol), and AgOTf (308 mg, 1.20 mmol). The resulting suspension was refluxed for 14 h exposed to air. The crude mixture was concentrated and chromatographed [silica, hexanes/CH$_2$Cl$_2$ (2:1)], affording a blue solid (83.0 mg, 30%): $^1$H NMR (300 MHz, THF-d$_8$) δ 1.84 (s, 6H), 2.03 (s, 6H), 2.58 (s, 3H), 4.56 (s, 2H), 7.24 (s, 2H), 8.26 (d, J=4.4 Hz, 1H), 8.41 (s, 1H), 8.57 (s, 1H), 8.78 (s, 1H), 8.81 (s, 1H), 8.84 (d, J=4.4 Hz, 1H), 9.62 (s, 1H); LD-MS obsd 679.6; FAB-MS obsd 675.9827, calcd 675.9816 (C$_{31}$H$_{26}$Br$_2$N$_4$Zn); λ$_{abs}$ 411, 622 nm.

Zn(II)-3-[2-(Triisopropylsilyl)ethynyl]-13-bromo-17,18-dihydro-18,18-dimethyl-porphyrin (ZnC-E$^3$Br$^{13}$). A solution of 14 (90.0 mg, 0.270 mmol) and 21 (91.0 mg, 0.245 mmol) in distilled CH$_2$Cl$_2$ (8 mL) was treated with a solution of p-TsOH.H$_2$O (233 mg, 1.22 mmol) in distilled methanol (2 mL) under argon. The reaction mixture was stirred at room temperature for 45 min. Workup followed by concentration of the crude mixture afforded a yellow solid. The crude yellow solid was dissolved in CH$_3$CN (24.5 mL) and subsequently treated with 2,2,6,6-tetramethylpiperidine (624 μL, 3.67 mmol), Zn(OAc)$_2$ (944 mg, 3.67 mmol), and AgOTf (135 mg, 0.735 mmol). The resulting suspension was refluxed for 18 h exposed to air. The crude mixture was concentrated and chromatographed [silica, hexanes/CH$_2$Cl$_2$ (6:4)], affording a purple solid (12.0 mg, 7%): $^1$H NMR (THF-d$_8$) δ 1.43-1.44 (m, 21H), 2.03 (s, 6H), 4.57 (s, 2H), 8.66 (s, 2H), 8.82 (s, 1H), 8.90 (s, 1H), 8.95 (d, J=4.0 Hz, 1H), 9.01 (d, J=4.0 Hz, 1H), 9.71 (s, 1H), 9.88 (s, 1H); LD-MS obsd 661.9.0; FAB-MS obsd 660.1266, calcd 660.1262 (C$_{33}$H$_{37}$BrN$_4$SiZn); λ$_{abs}$ 418, 634 nm.

Zn(II)-13-Bromo-17,18-dihydro-10-mesityl-18,18-dimethyl-3-[2-(triisopropylsilyl)ethynyl]porphyrin (ZnC-E$^3$M$^{10}$Br$^{13}$). A stirred suspension of 16 (160 mg, 0.355 mmol) and 21 (110 mg, 0.300 mmol) in distilled CH$_2$Cl$_2$ (8.5 mL) was treated with a solution of p-TsOH.H$_2$O (283 mg, 1.50 mmol) in distilled methanol (3.5 mL) under argon. The reaction mixture was stirred at room temperature for 30 min. Workup followed by concentration of the crude mixture afforded a yellow viscous liquid. The viscous liquid was dissolved in CH$_3$CN (30 mL) and subsequently treated with 2,2,6,6-tetramethylpiperidine (0.750 mL, 4.50 mmol), Zn(OAc)$_2$ (545 mg, 3.00 mmol), and AgOTf (228 mg, 0.890 mmol). The resulting suspension was refluxed for 16 h exposed to air. The crude mixture was concentrated and chromatographed [silica, hexanes/CH$_2$Cl$_2$ (2:1)], affording a purple solid (26.0 mg, 11%): $^1$H NMR δ (300 MHz, THF-d$_8$) 1.30 (s, 3H), 1.43 (m, 18H), 1.85 (s, 6H), 2.03 (s, 6H), 2.60 (s, 3H), 4.57 (s, 2H), 7.25 (s, 2H), 8.26 (d, J=4.0 Hz, 1H), 8.41 (d, J=4.0 Hz, 1H), 8.58-8.60 (m, 1H), 8.77 (d, J=4.0 Hz, 2H), 8.84-8.87 (m, 1H), 9.76-9.78 (m, 1H); LD-MS obsd 779.0; FAB-MS obsd 778.2038, calcd 778.2045 (C$_{42}$H$_{47}$BrN$_4$SiZn); tabs 418, 634 nm.

Zn(II)-17,18-Dihydro-10-mesityl-18,18-dimethyl-3-vinylporphyrin (ZnC-V$^3$M$^{10}$). Following a procedure for Stille coupling with porphyrins (DiMagno, S. G. et al., *J. Org. Chem.* 1993, 58, 5983-5993), a mixture of ZnC—Br$^3$M$^{10}$ (20 mg, 33 μmol), Bu$_3$SnCH=CH$_2$ (20 μL, 68 μmol) and (PPh$_3$)$_2$PdCl$_2$ (3.0 mg, 4.0 μmol) was refluxed in THF (2 mL) for 14 h in a Schlenk line. The reaction mixture was concentrated and chromatographed [silica, CH$_2$Cl$_2$], affording a blue solid (12 mg, 66%): $^1$H NMR δ 1.86 (s, 6H), 2.02 (s, 6H), 2.60 (s, 3H), 4.50 (s, 2H), 5.85 (d, J=10.8 Hz, 1H), 6.47 (d, J=17.5 Hz, 1H), 7.23 (s, 2H), 8.19 (dd, J=17.5, 10.8 Hz, 1H), 8.33 (d, J=4.1 Hz, 1H), 8.50 (d, J=4.4 Hz, 1H), 8.52 (s, 1H), 8.55 (d, J=4.4 Hz, 1H), 8.59 (s, 1H), 8.81 (d, J=4.1 Hz, 1H), 8.83 (s, 1H), 9.68 (s, 1H); LD-MS obsd 546.7; FAB-MS obsd 546.1739, calcd 546.1762 (C$_{33}$H$_{30}$N$_4$Zn); λ$_{abs}$ 414, 621 nm.

Zn(II)-3-(2-(Triisopropylsilyl)ethynyl)-17,18-dihydro-10-mesityl-18,18-dimethylporphyrin (ZnC-E³M¹⁰). Following a procedure for Sonogashira coupling with chlorins (Taniguchi, M. et al., *J. Org. Chem.* 2005, 70, 275-285), a mixture of ZnC—Br³M¹⁰ (18 mg, 0.030 mmol), (triisopropylsilyl)acetylene (14 µL, 0.060 mmol), Pd₂(dba)₃ (4.2 mg, 0.0045 mmol), and P(o-tol)₃ (11 mg, 0.036 mmol) was heated at 60° C. in toluene/triethylamine (5:1, 12 mL) in a Schlenk line. After 7 h, (triisopropylsilyl)acetylene (14 µL, 0.060 mmol), Pd₂(dba)₃ (4.2 mg, 0.0045 mmol), and P(o-tol)₃ (11 mg, 0.036 mmol) were added to the reaction mixture. After 18 h, the reaction mixture was concentrated and chromatographed [silica, hexanes/CH₂Cl₂ (2:1)], affording a green solid (11 mg, 52%): ¹H NMR δ 1.38 (s, 18H), 1.40 (m, 3H), 1.85 (s, 6H), 2.01 (s, 6H), 2.60 (s, 3H), 4.51 (s, 2H), 7.22 (s, 2H), 8.36 (d, J=4.1 Hz, 1H), 8.50-8.54 (m, 2H), 8.60 (d, J=4.1 Hz, 1H), 8.67 (s, 1H), 8.80-8.85 (m, 2H), 9.88 (s, 1H); LD-MS obsd 700.5; FAB-MS obsd 700.2930, calcd 700.2940 ($C_{42}H_{49}N_4SiZn$); $\lambda_{abs}$ 416, 627 nm.

Zn(II)-13-Acetyl-17,18-dihydro-10-mesityl-18,18-dimethylporphyrin (ZnC-M¹⁰A¹³). A solution of ZnC-M¹⁰Br¹³ (50 mg, 0.083 mmol) in CH₂Cl₂ (1.0 mL) was treated dropwise with TFA (0.13 mL, 1.6 mmol) over 2 min. The solution was stirred at room temperature for 2 h. CH₂Cl₂ was added and the organic layer was washed (saturated aqueous NaHCO₃, water, brine) and then dried (Na₂SO₄). The crude mixture was concentrated and used in the next step. Following a procedure for replacement of a bromo group with an acetyl group on an aromatic substrate,[28] a mixture of the crude product, tributyl(1-ethoxyvinyl)tin (49 µL, 0.14 mmol) and (PPh₃)₂PdCl₂ (10 mg, 0.014 mmol) was refluxed in THF (7 mL) for 20 h in a Schlenk line. The reaction mixture was treated with 10% aqueous HCl (4 mL) at room temperature for 2 h. CH₂Cl₂ was added and the organic layer was separated. The organic layer was washed (saturated aqueous NaHCO₃, water, brine), dried (Na₂SO₄), and concentrated. The resulting residue was dissolved in CHCl₃ (5 mL). The solution was treated with Zn(OAc)₂·2H₂O (320 mg, 1.45 mmol) in MeOH (2 mL) and the reaction mixture was stirred overnight at room temperature. Concentration followed by chromatography of the crude mixture [silica, CH₂Cl₂/hexanes (1:1)] gave a green solid (25 mg, 53%): ¹H NMR δ 1.82 (s, 6H), 2.00 (s, 6H), 2.60 (s, 3H), 2.72 (s, 3H), 4.47 (s, 2H), 7.20 (s, 2H), 8.30 (d, J=4.4 Hz, 1H), 8.48 (s, 1H), 8.68 (d, J=4.4 Hz, 2H), 8.81 (s, 1H), 8.96 (d, J=4.4 Hz, 1H), 9.38 (s, 1H), 9.55 (s, 1H); LD-MS obsd 560.7; FAB-MS obsd 562.1745, calcd 562.1711 ($C_{33}H_{30}N_4OZn$); $\lambda_{abs}$ 418, 587, 632 mm.

Zn(II)-13-[2-(Triisopropylsilyl)ethynyl]-17,18-dihydro-10-mesityl-18,18-dimethylporphyrin (ZnC-M¹⁰E¹³). A mixture of ZnC-M¹⁰Br¹³ (18 mg, 0.030 mmol), (triisopropylsilyl)acetylene (14 µL, 0.060 mmol), Pd₂(dba)₃ (4.2 mg, 0.0045 mmol), and P(o-tol)₃ (11 mg, 0.036 mmol) was heated at 60° C. in toluene/triethylamine (5:1, 12 mL) in a Schlenk line. After 7 h, (triisopropylsilyl)acetylene (14 µL, 0.060 mmol), Pd₂(dba)₃ (4.2 mg, 0.0045 mmol), and P(o-tol)₃ (11 mg, 0.036 mmol) were added to the reaction mixture. After 18 h, the reaction mixture was concentrated and chromatographed [silica, hexanes/CH₂Cl₂ (2:1)], affording a green solid (15 mg, 71% yield): ¹H NMR δ 1.38 (s, 18H), 1.40 (m, 3H), 1.85 (s, 6H), 2.02 (s, 6H), 2.60 (s, 3H), 4.51 (s, 2H), 7.24 (s, 2H), 8.35 (d, J=4.1 Hz, 1H), 8.55 (s, 1H), 8.59 (s, 1H), 8.66 (d, J=4.1 Hz, 1H), 8.76 (d, J=4.1 Hz, 1H), 9.00-9.02 (m, 2H), 9.51 (s, 1H); LD-MS obsd 698.5; FAB-MS obsd 562.1745, calcd 700.2940 ($C_{42}H_{48}N_4SiZn$); $\lambda_{abs}$ 412, 577, 626 nm.

Zn(II)-3,13-Bis[2-(triisopropylsilyl)ethynyl]-17,18-dihydro-18,18-dimethyl-porphyrin (ZnC-E³E¹³). Following a reported procedure (Taniguchi, M. et al., *J. Org. Chem.* 2005, 70, 275-285), samples of ZnC—Br³Br¹³ (12.0 mg, 0.0214 mmol) and (triisopropylsilyl)acetylene (28.5 µL, 0.128 mmol) were coupled using Pd₂(dba)₃ (2.90 mg, 0.00321 mmol) and P(o-tol)₃ (8.50 mg, 0.0256 mmol) in toluene/triethylamine (5:1, 9 mL) at 60° C. under argon. After 5 h, (triisopropylsilyl)acetylene (28.5 µL, 0.128 mmol), Pd₂(dba)₃ (2.90 mg, 0.00321 mmol), and P(o-tol)₃ (8.50 mg, 0.0256 mmol) were added to the reaction mixture. After 24 h, the reaction mixture was concentrated under reduced pressure. The resulting residue was chromatographed [silica, hexanes/CH₂Cl₂ (8:2)], affording a greenish purple solid (8.6 mg, 53%): ¹H NMR (THF-d₈) δ 1.42-1.45 (m, 42H), 2.03 (s, 6H), 4.57 (s, 2H), 8.65 (s, 1H), 8.69 (s, 1H), 8.86 (s, 1H), 8.90 (s, 1H), 8.95 (s, 2H), 9.85 (s, 1H), 9.87 (s, 1H); LD-MS obsd 763.9; FAB-MS obsd 762.3492, calcd 762.3492 ($C_{44}H_{58}N_4Si_2Zn$); $\lambda_{abs}$ 421, 645 nm.

Zn(II)-3,13-Bis[2-(triisopropylsilyl)ethynyl]-17,18-dihydro-10-mesityl-18,18-dimethylporphyrin (ZnC-E³M¹⁰E¹³). Samples of ZnC—Br³M¹⁰Br¹³ (25 mg, 0.036 mmol) and (triisopropylsilyl)acetylene (16 µL, 0.072 mmol) were coupled using Pd₂(dba)₃ (5.0 mg, 0.0055 mmol), and P(o-tol)₃ (14 mg, 0.046 mmol) in toluene/triethylamine (5:1, 9 mL) at 60° C. under argon. After 20 h, (triisopropylsilyl)acetylene (16 µL, 0.072 mmol), Pd₂(dba)₃ (5.0 mg, 0.0055 mmol), and P(o-tol)₃ (14 mg, 0.046 mmol) were added to the reaction mixture. After 32 h, the reaction mixture was concentrated under reduced pressure. The resulting residue was chromatographed [silica, hexanes/CH₂Cl₂ (2:1)], affording a green solid (24 mg, 75%): ¹H NMR δ 1.38 (s, 18H), 1.40 (s, 24H), 1.86 (s, 6H), 2.03 (s, 6H), 2.61 (s, 3H), 4.52 (s, 2H), 7.24 (s, 2H), 8.34 (d, J=3.9 Hz, 1H), 8.50 (s, 1H), 8.56 (s, 1H), 8.80 (d, J=3.9 Hz, 1H), 8.83 (s, 1H), 8.99 (s, 1H), 9.81 (s, 1H), LD-MS obsd 880.4; FAB-MS obsd 880.4321, calcd 880.4274 ($C_{53}H_{68}N_4Si_2Zn$); $\lambda_{abs}$ 423, 646 nm.

Zn(II)-13-Acetyl-3-[2-(triisopropylsilyl)ethynyl]-17,18-dihydro-18,18-dimethyl-porphyrin (ZnC-E³A¹³). A solution of ZnC-E³Br¹³ (8.0 mg, 0.012 mmol) in CH₂Cl₂ (0.2 mL) was treated dropwise with TFA (29 µL, 0.36 mmol) over 2 min. The solution was stirred at room temperature for 2 h. CH₂Cl₂ was added and the organic layer was washed (saturated aqueous NaHCO₃, water, brine) and then dried (Na₂SO₄). The crude mixture was concentrated and used in the next step. A mixture of the crude product, tributyl(1-ethoxyvinyl)tin (17 µL, 0.048 mmol) and (PPh₃)₂PdCl₂ (1.3 mg, 0.0018 mmol) was refluxed in THF (1.2 mL) for 20 h in a Schlenk line. The reaction mixture was treated with 10% aqueous HCl (0.5 mL) at room temperature for 2 h. CH₂Cl₂ was added and the organic layer was separated. The organic layer was washed (saturated aqueous NaHCO₃, water, brine), dried (Na₂SO₄), and concentrated. The resulting residue was dissolved in CHCl₃ (0.8 mL). The solution was treated with Zn(OAc)₂·2H₂O (40 mg, 0.18 mmol) in MeOH (0.2 mL) and the reaction mixture was stirred for 4 h at room temperature. Concentration followed by chromatography of the crude mixture [silica, CH₂Cl₂] gave a green solid (4.0 mg, 53%): ¹H NMR (THF-d₈) δ 1.42 (s, 21H), 2.04 (s, 6H), 3.13 (s, 3H), 4.57 (s, 2H), 8.67 (s, 1H), 8.78 (s, 1H), 8.92 (s, 2H), 8.94 (d, J=4.4 Hz, 1H), 9.06 (d, J=4.4 Hz, 1H), 9.32 (s, 1H), 9.84 (s, 1H); LD-MS obsd 624.3; FAB-MS obsd 624.2256, calcd 624.2263 ($C_{35}H_{40}N_4OSiZn$); $\lambda_{abs}$ 428, 655 nm.

Zn(II)-13-Acetyl-3-[2-(triisopropylsilyl)ethynyl]-17,18-dihydro-10-mesityl-18,18-dimethylporphyrin (ZnC-E³M¹⁰A¹³). A solution of ZnC-E³M¹⁰Br¹³ (19 mg, 0.024 mmol) in CH₂Cl₂ (0.25 mL) was treated dropwise with TFA (38 µL, 0.49 mmol) over 2 min. The solution was stirred at room temperature for 3 h. CH₂Cl₂ was added and the organic layer was washed (saturated aqueous NaHCO$_3$, water, brine) and then dried (Na$_2$SO$_4$). The crude mixture was concentrated and used in the next step. A mixture of the crude product, tributyl(1-ethoxyvinyl)tin (17 μL, 0.050 mmol) and (PPh$_3$)$_2$PdCl$_2$ (2.5 mg, 0.0036 mmol) was refluxed in THF (2.5 mL) for 20 h in a Schlenk line. The reaction mixture was treated with 10% aqueous HCl (1 mL) at room temperature for 2 h. CH$_2$Cl$_2$ was added and the organic layer was separated. The organic layer was washed (saturated aqueous NaHCO$_3$, water, brine), dried (Na$_2$SO$_4$), and concentrated. The resulting residue was dissolved in CHCl$_3$ (2 mL). The solution was treated with Zn(OAc)$_2$·2H$_2$O (53 mg, 0.24 mmol) in (0.5 mL) MeOH and the reaction mixture was stirred for 4 h at room temperature. Concentration followed by chromatography of the crude mixture [silica, CH$_2$Cl$_2$] gave a green solid (4.2 mg, 23%): $^1$H NMR δ 1.38 (s, 21H), 1.83 (s, 6H), 1.98 (s, 6H), 2.60 (s, 3H), 2.82 (s, 3H), 4.47 (s, 2H), 7.22 (s, 2H), 8.30 (d, J=4.4 Hz, 1H), 8.43 (s, 1H), 8.72 (d, J=4.4 Hz, 1H), 8.79 (s, 1H), 8.84 (s, 1H), 9.64 (s, 1H), 9.70 (s, 1H); LD-MS obsd 742.6; FAB-MS obsd 742.3022, calcd 742.3045 (C$_{45}$H$_{50}$N$_4$OSiZn); λ$_{abs}$ 428, 652 nm.

tography. Treatment of 24 with TosMIC in the presence of NaH furnished swallowtail-substituted pyrrole 25. Hydrolysis of the ethyl ester with powdered NaOH in hot ethylene glycol resulted in decarboxylation to give 26. Formylation of 26 yielded two isomeric products (27a, 27b). Unlike the analogous 2-formyl-3-p-tolylpyrrole (Kim, H.-J. and Lindsey, J. S. J. Org. Chem. 2005, 70, 5475-5486), 27a/b was an oil, and thus not purifiable through crystallization. The products also were not easily separated by column chromatography. Accordingly, the mixture of 27a/b was subjected first to Henry reaction with nitromethane in methanol containing propylamine and acetic acid, and the crude product obtained therefrom was reduced with NaBH$_4$. Column chromatography gave 28 as a single isomer. Treatment of 28 with mesityl oxide dimethyl acetal (29, 1.1 equiv) and DBU in acetonitrile followed by chromatography on neutral alumina yielded hexanone 30 as a yellow oil. Cyclization of 30 in THF with excess NaOMe followed by deoxygenation with TiCl$_3$ gave dihydrodipyrrin 31. Swallowtail dihydrodipyrrin 31 was obtained in 26% yield from 30 (1.2% over seven steps from aldehyde 23). Yields throughout were comparable to those reported for the p-tolyl substituted analogues.

Example 3

Water-soluble Bacteriochlorins By Incorporation of Polar-Terminated Swallowtail Motifs Results and Discussion. The incorporation of one or more polar-terminated swallowtail motifs at the periphery of a chlorin or bacteriochlorin is expected to impart solubility in water. Current methodology for the de novo synthesis of bacteriochlorins conceivably can be exploited for the introduction of a swallowtail unit at three distinct types of positions: (1) at the α-pyrrolic positions (e.g., 2, 3, 12, 13), (2) as an integral part of the reduced, pyrroline ring in place of the geminal dimethyl groups, or (3) at the 15-position.

The three distinct locations in turn entail distinct synthetic methods. Substitution at the β-pyrrolic positions is best achieved by introduction of the swallowtail substituent at the outset of the synthesis, most likely via van Leusen pyrrole synthesis followed by the established dihydrodipyrrin-acetal synthesis (Kim, H.-J. and Lindsey, J. S. J. Org. Chem. 2005, 70, 5475-5486). Incorporation of the swallowtail substituent as an integral component of the pyrroline ring necessitates the construction of a suitable analogue of mesityl oxide to be used in the synthesis of the dihydrodipyrrin-acetal. Substitution at the 15-position requires site-specific bromination of 5-methoxybacteriochlorin at the 15-position with NBS (Fan, D. and Lindsey, J. S. unpublished results), followed by Suzuki- or Sonogashira coupling. Herein we describe investigation of the first two routes, which correspond to designs (1) and (2).

A. Design 1. Design 1 incorporates the swallowtail unit at the 2- and 12-positions (β-pyrrolic positions) of the bacteriochlorin. The synthetic strategy entails incorporation of the swallowtail unit at the stage of the pyrrole synthesis, prior to forming the dihydrodipyrrin-acetal. The dihydrodipyrrin-acetal incorporating the swallowtail substituent at the 5-position was synthesized from aldehyde 23 (Scheme 11). Aldehyde 23 in turn was prepared from commercially available 2-bromoethyl methyl ether (22) analogously to the previously reported swallowtail aldehyde (23a) (Borbas, K. E. et al. Bioconjugate Chem. 2006, 17, 638-653). Reaction of 23 with (carbethoxymethylene)triphenylphosphorane yielded the unsaturated ester 24 in excellent yield after column chroma-

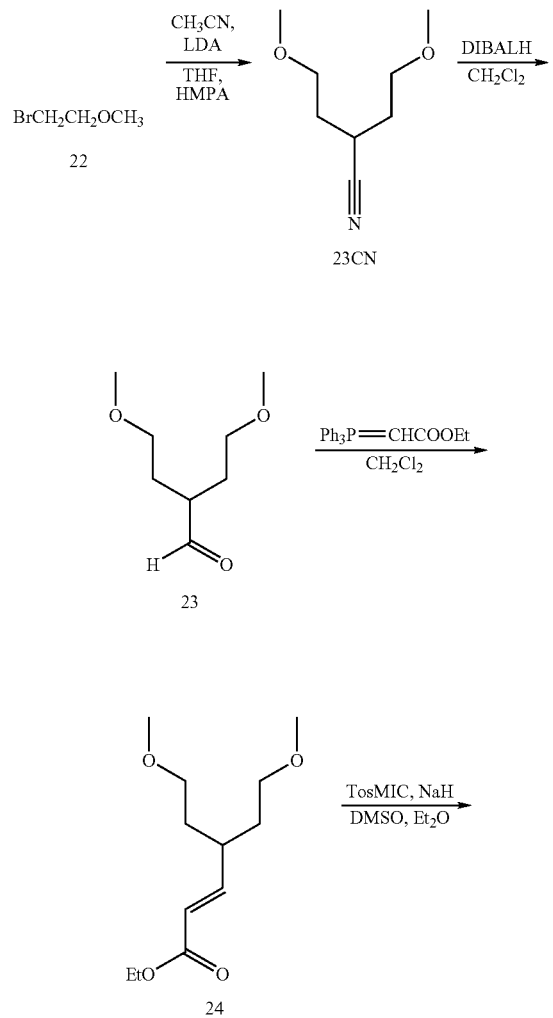

Scheme 11

-continued

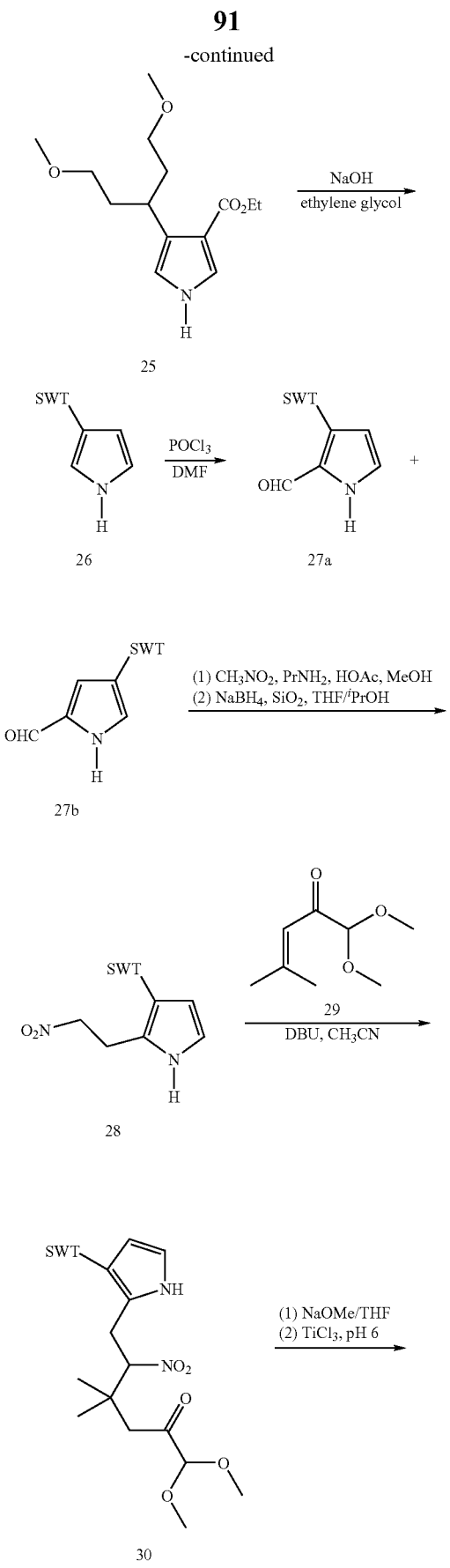

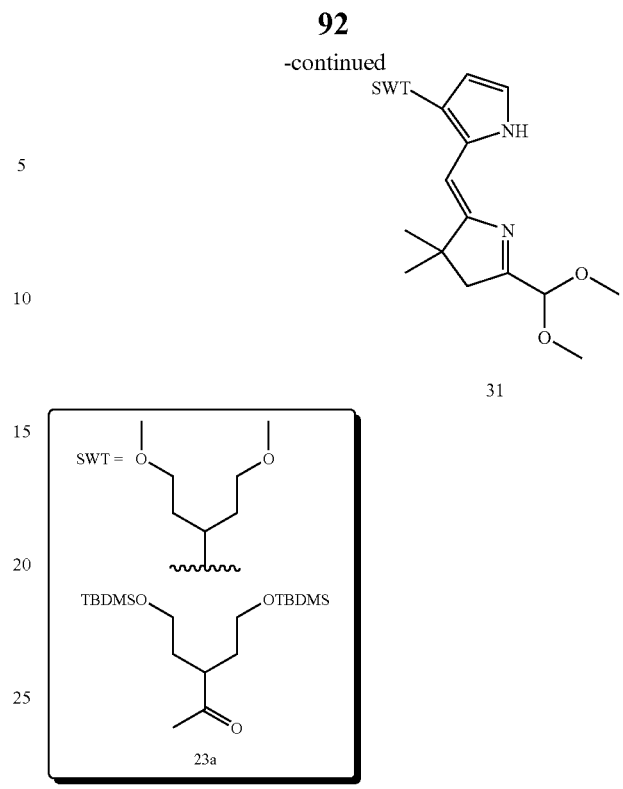

Self-condensation of dihydrodipyrrin 31 in the presence of BF$_3$.OEt$_2$ yielded two bacteriochlorins: 32 (major) and 33 (trace) (Scheme 12). The two bacteriochlorins were observed by TLC analysis and LD-MS analysis. The two bacteriochlorins differ in the nature of a single substituent, with 32 bearing a proton and 33 bearing a methoxy group at the respective 5-position. Column chromatography afforded bacteriochlorin 32 in 13% yield, while 33 was obtained in quantities that only permitted LD-MS (m/z 660.7) and absorption spectroscopy but not NMR analysis. Bacteriochlorin 32 is an excellent model compound for refining conditions for the manipulation of the terminal groups of the swallowtail unit. Also, the successful synthesis of 32 helped identify the methoxy protecting groups as sufficiently robust to withstand the reaction conditions that were employed. Nevertheless, there are a number of drawbacks to Design 1, which are as follows:

(1) the low yield of the macrocyclization, possibly due to the instability of the alkyl-substituted dihydrodipyrrin, as opposed to the previously reported p-tolyl-substituted analogue.

(2) swallowtail aldehyde 23 is not commercially available, and has to be synthesized in a two-step procedure, both of which require chromatographic purification (3) introduction of the bioconjugatable site has to be carried out post-macrocyclization, further increasing the number of steps.

(4) even though there are a number of methods for cleaving methyl ethers, none is particularly mild, thereby limiting the choice of bioconjugatable groups that ultimately also are desired in the bacteriochlorin.

It was hypothesized that the introduction of an aromatic group bearing a bioconjugatable functionality into the dihydrodipyrrin unit would help overcome both problems (1) and (3). Therefore, the synthesis of bacteriochlorins of Design 2 was attempted.

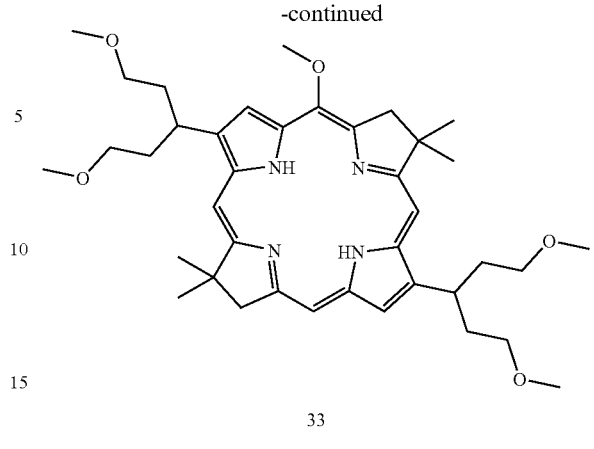

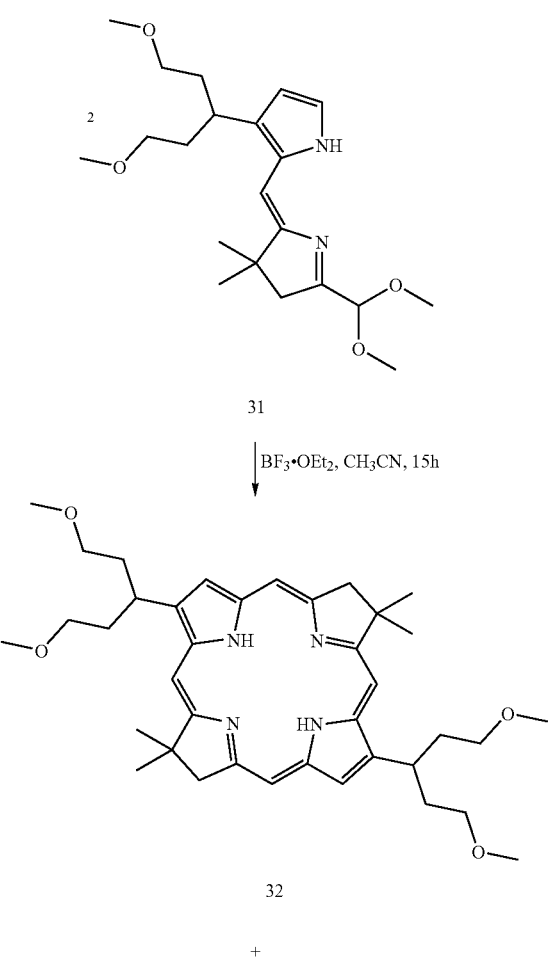

B. Design 2. Design 2 incorporates the swallowtail motif as an integral component of the reduced, pyrroline ring. The success of Design 2 depends on the synthesis of an analogue of mesityl oxide such as 34. There are a number of conceivable ways to prepare this compound, three of which are shown in Scheme 13. It is possible to engage ketone 35 in a Wittig or Wadsworth-Emmons reaction with phosphorous reagents P1 or P2 to furnish 34, although 35 was expected to react rather sluggishly with P1, if at all. Aldol condensation of 35 with acetone or a silyl enol ether thereof could produce either a tertiary alcohol or even α,β-unsaturated ketone 34 directly, if dehydration occurs during the reaction. Alternatively, treatment of 35 with iodoform in the presence of anhydrous CrCl$_2$ would yield vinyl iodide 36, which could participate in a Nozaki-Kishi coupling with acetaldehyde to furnish a secondary alcohol. This secondary alcohol could then be oxidized to ketone 34 via established methods.

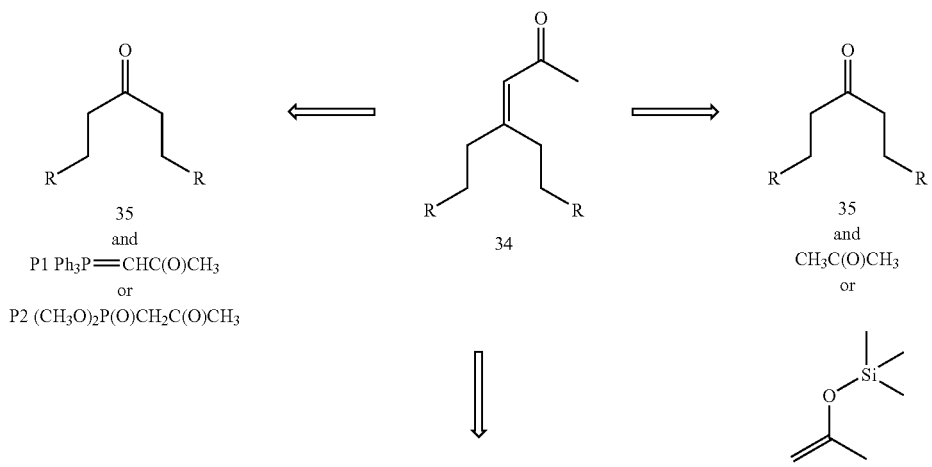

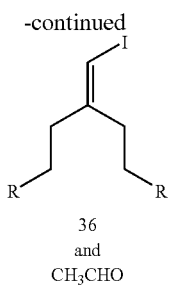

36
and
CH₃CHO

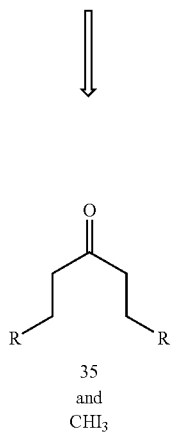

35
and
CHI₃

R = OTBDMS (too labile), OTBDPS (50), Br (35Br₂), OCH₃ (35)

The synthesis of ketone 35 (R=OCH₃) and attempts at the preparation of mesityl oxide analogue 34 (R=OCH₃) are depicted in Scheme 14. Ketone 35 was synthesized via the two-step dialkylation of 1,3-dithiane (37) with bromoethyl methyl ether. The carbonyl group was revealed by oxidative cleavage of the 1,3-dithiane functionality by NBS or NCS/AgNO₃ (Corey, E. J. and Erickson, B. W. *J. Org. Chem.* 1971, 36, 3553-3560). The latter method gave better (>95%) yields in our hands, while other literature procedures (Stutz, P. and Stadler, P. A. *Org. Synth.* 1988, *Coll. Vol.* 6. 109) resulted in complete decomposition of 39. It is worth mentioning that the dibromo analogue of 35 (35Br₂) was also prepared following a reported procedure (Sviridov, S. V. et al. *Zh. Org. Khim.* 1991, 27, 1431-1433), but proved unstable to a number of reaction conditions. Another reported method (Devasagayaraj, A. and Knochel, P. *Tetrahedron Lett.* 1995, 36, 8411-8414), based on the insertion of zinc into the halogen-carbon bond of an alkyl iodide or bromide, followed by carbonylation with in situ-generated cobalt octacarbonyl gave a bis-OTBDMS-substituted symmetrical ketone in <10% yield.

Scheme 14

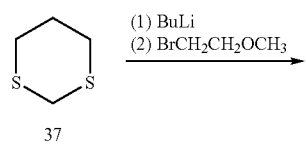

-continued

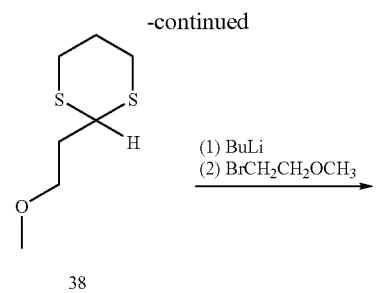

38

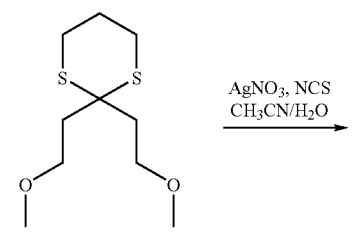

39

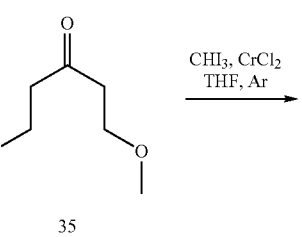

35

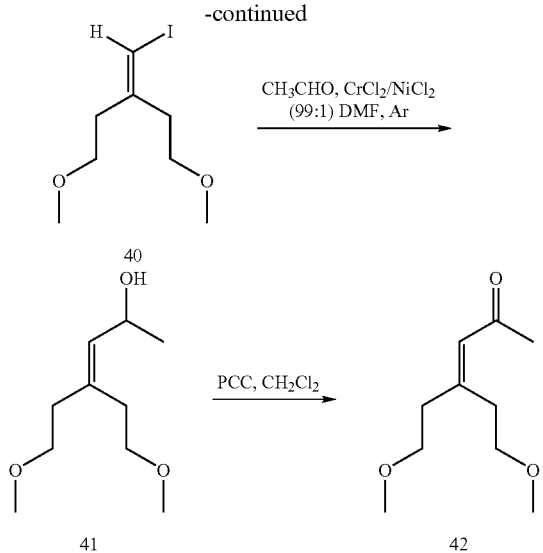

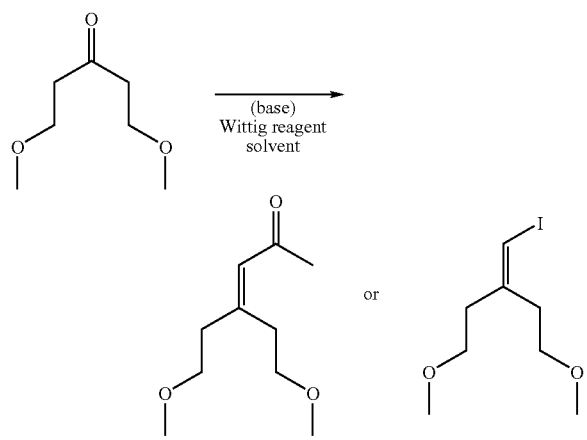

TABLE 4

Reaction conditions for the Wittig reactions of ketone 35

| | base | reagent | T | solvent |
|---|---|---|---|---|
| 1 | KOH | 2 | r.t. | EtOH/H$_2$O |
| 2 | KOH | 2 | reflux | EtOH/H$_2$O |
| 3 | NaH | 2 | 0 | THF |
| 4 | NaH | 2 | r.t. | THF |
| 5 | NaH | 2 | reflux | THF |
| 6 | NaH | 2 | reflux | CH$_3$OCH$_2$CH$_2$OCH$_3$ |
| 7 | BuLi | 2 | 0 | THF |
| 8 | BuLi | 2 | −78 | THF |
| 9 | BuLi | 3 | 0->r.t | THF |
| 10 | LiHMDS | 3 | −78 | THF |

TABLE 4-continued

Reaction conditions for the Wittig reactions of ketone 35

| | base | reagent | T | solvent |
|---|---|---|---|---|
| 11 | LiHDMS | 3 | r.t | THF |
| 12 | none | 1 | reflux | CH$_2$Cl$_2$ |
| 13 | none | 1 | reflux | THF |
| 14 | none* | 1 | reflux | toluene |

*Excellent yield in one instance, not reproducible
**Reagent 1: Ph$_3$=CHC(O)CH$_3$; reagent 2: (CH$_3$O)$_2$P(O)CH$_2$C(O)CH$_3$; reagent 3: Ph$_3$CH$_2$I$^+$I$^-$ Ketone 35 was not reactive towards phosphorous reagents P1 or P2 under a variety of conditions (Table 4). The desired α,β-unsaturated ketone was isolated in good yield in one instance (toluene, Ar atmosphere, excess P1, reflux, 24 h), but the reaction was not reproducible, and, after extensive attempts at optimization, was abandoned. Reactions with phosphonate P2 resulted in either rapid decomposition of 35, or its recovery even after 24 h of reaction. Therefore, despite the apparent simplicity, this route was abandoned.

Treatment of 35 with iodoform in the presence of CrCl$_2$ in anhydrous THF (Takai, K. et al. J. Am. Chem. Soc. 2003, 125, 12990-12991; Yakelis, N. A. and Roush, W. R. J. Org. Chem. 2003, 68, 3838-3843; Aoyagi, S. et al. J. Org. Chem. 2002, 67, 5517-5526; Takai, K. and Utimoto, K. J. Am. Chem. Soc. 1986, 108, 7408-7410) yielded the desired vinyl iodide 40 in near-quantitative yield after aqueous-organic work-up and chromatography on silica (Scheme 14). Chromium(II)-mediated (Kishi-Nozaki) coupling (Drouet, K. E. and Theodorakis, E. A. J. Am. Chem. Soc. 1999, 121, 456-457; Harried, S. S. et al. J. Org. Chem., 1997, 62, 6098-6099) of 40 with acetaldehyde yielded secondary alcohol 41 as a yellow oil, which was oxidized in crude form with PCC in CH$_2$Cl$_2$ (Corey, E. J. and Suggs, W. J. Tetrahedron Lett. 1975, 2647-2650). Although 42 was obtained in this manner, this route is not ideal for a variety of reasons. The number of linear synthetic steps is high (6), some of which are sensitive to scaling-up. A major problem is the use of a large excess of the expensive, toxic and environmentally problematic chromium (II) chloride in two of the synthetic steps. We attempted the synthesis of vinyl iodide 40 from the reaction of 35 and the triphenylphosphonium ylide of iodoform (Conway, J. C. et al. Tetrahedron, 2005, 61, 11910-11923) in the presence of BuLi, (Barker, M. et al. J. Med. Chem. 2006, 49, 4216-4231) but the formation of 40 was not observed, and 35 was not recovered.

An alternative synthesis of intermediate 34 can be envisaged via the mixed aldol reaction between ketone 35 (or a suitably modified derivative) and acetone or a surrogate thereof. Attempts at engaging 35 in a Mukaiyama aldol reaction with 2-(trimethylsilyloxy)propene were unsuccessful. A number of Lewis acid catalysts, known to promote Mukaiyama aldol reactions, were tested. No reaction was observed in the presence of BF$_3$—OEt$_2$ or Ti(O$^1$Pr)$_4$, even after 24 h at room temperature. Replacement of the catalyst with TiBr$_4$ resulted in the appearance of a new product, as observed by TLC, albeit only in trace amounts. The use of TiCl$_4$ gave complete conversion of the starting material, but the major component was identified as a chlorinated derivative of 35 upon ESI-MS and $^1$H NMR analysis of the crude product. It was likely that the ether oxygens in ketone 35 were more basic than the carbonyl oxygen and were preferentially coordinating to the metal, which explains both the lack of the aldol reaction and the Meow Cl substitution. Therefore, the methyl ether protection was replaced by a non-coordinating silyl-based protecting group. The tert-butyldiphenylsilyl (TBDPS) group was chosen over the TBDMS (tert-butyldimethylsilyl) group given that the former is quite stable under acidic conditions (notably p-TsOH and BF$_3$.OEt$_2$) and is inert to BuLi (vide infra).

The synthesis of intermediate 52 is shown in Scheme 15. The known TBDPS-protected aldehyde 45b (n=2) was synthesized in two steps from 1,4-butanediol (Freeman, F. and Kim, D. S. H. L. J. Org. Chem. 1992, 57, 1722-1727). Iodide 46b was prepared from TBDPS-protected 1,3-propanediol 44b by treatment with a mixture of $I_2$/PPh$_3$/imidazole (Ryu, K. et al. *Org. Lett.* 2006, 8, 3343-3345), followed by column chromatography. Negishi-coupling of aldehyde 45b and lithiated 46b gave secondary alcohol 49 in an unoptimized 49% yield (Negishi, E.-i. et al. *J. Org. Chem.* 1990, 55, 5406-5409; Negishi, E.-i. et al. *Org. Lett.* 2002, 4, 261-264; Iriondo-Alberdi, J. et al. *Org. Lett.* 2005, 7, 3969-3971). It is worth noting that the short-chain analogue of 49 was not synthesizable via this route. Aldehyde 45a (n=1) was prepared analogously to 45b, and iodide 46a was synthesized from 2-bromoethanol by O-protection with TBDPS-Cl followed by Finkelstein reaction. As 2-alkoxyhalides are known to undergo β-elimination under Grignard conditions (Smith, M. B. and March, J. March's advanced organic chemistry: reactions, mechanisms, and structure. 5$^{th}$ Ed. 2001, John Wiley & Sons, Inc., New York, N.Y.), it is possible that a similar side-reaction was decreasing the stability of the lithiated species formed from 46a. PCC-oxidation (Corey, E. J. and Suggs, W. J. *Tetrahedron Lett.* 1975, 2647-2650) of 49 furnished bis-TBDMS-protected 4-heptanone as a colorless oil after column chromatography. Treatment of heptanone 50 with 1.1 equiv of TiCl$_4$ in anhydrous CH$_2$Cl$_2$ (Mukaiyama, T. and Narasaka, K. *Org. Synth.* 1993, *Coll. Vol.* 8. 6), followed by 2-(trimethylsilyloxy)propene gave a mixture of 50 and secondary alcohol 51 in an approximate 3:1 mixture after 20 min. Optimization of this procedure is currently underway. As the decomposition of 51 was not observed, it is expected that longer reaction times will allow for the complete conversion of 50 to 51.

Scheme 15a

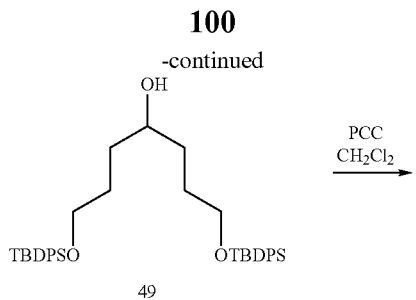

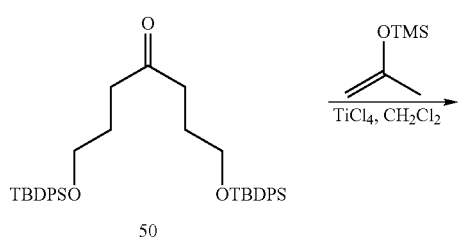

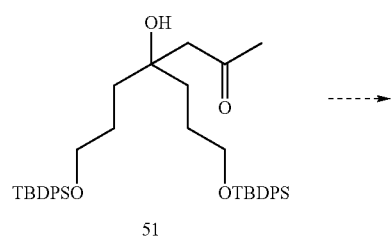

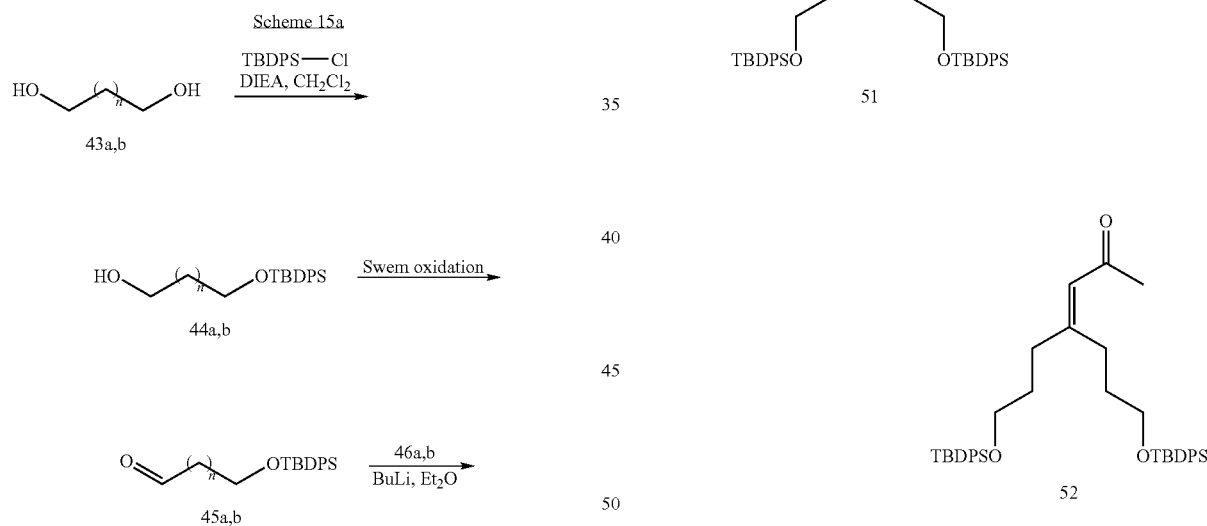

Scheme 15b

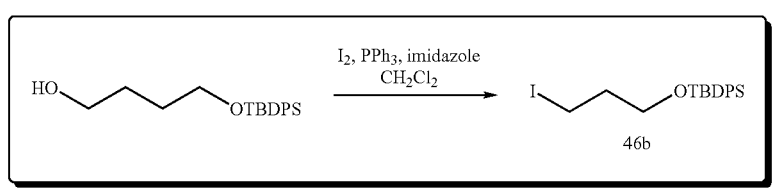

Scheme 15c

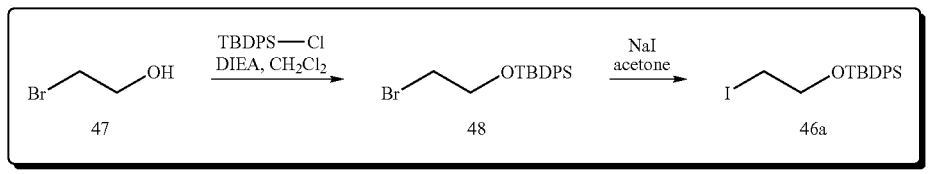

C. Introduction of the bioconjugatable site. We attempted the introduction of a bioconjugatable group at one of the β-pyrrole positions by replacing the p-tolyl group by a 4-nitrophenyl substituent (Scheme 16).

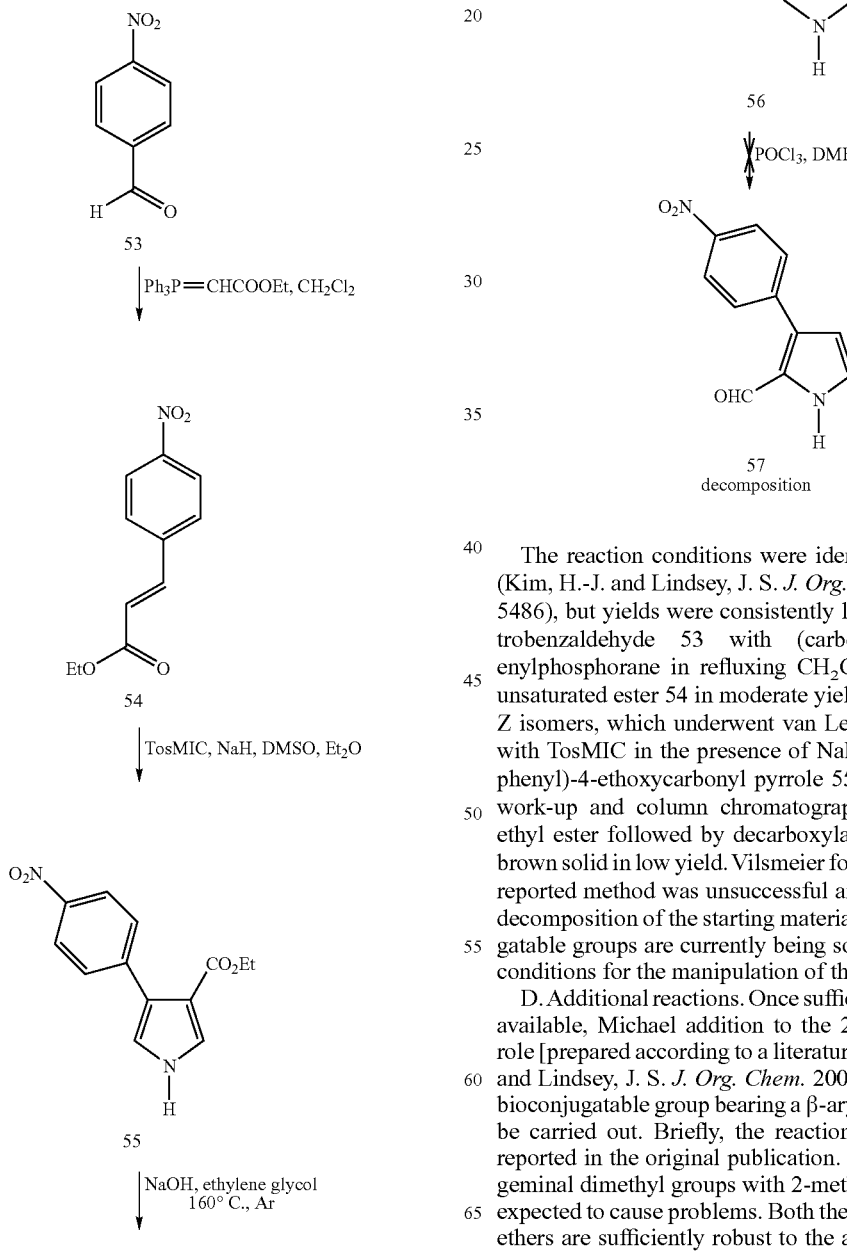

The reaction conditions were identical to those reported (Kim, H.-J. and Lindsey, J. S. *J. Org. Chem.* 2005, 70, 5475-5486), but yields were consistently lower. Reaction of 4-nitrobenzaldehyde 53 with (carbethoxymethylene)triphenylphosphorane in refluxing $CH_2Cl_2$ yielded the desired unsaturated ester 54 in moderate yield as a mixture of E and Z isomers, which underwent van Leusen pyrrole formation with TosMIC in the presence of NaH to furnish 3-(4-nitrophenyl)-4-ethoxycarbonyl pyrrole 55 after aqueous-organic work-up and column chromatography. Hydrolysis of the ethyl ester followed by decarboxylation gave 56 as a dark brown solid in low yield. Vilsmeier formylation following the reported method was unsuccessful and resulted in complete decomposition of the starting material. Alternative bioconjugatable groups are currently being sought, as well as milder conditions for the manipulation of this sensitive substituent.

D. Additional reactions. Once sufficient quantities of 52 are available, Michael addition to the 2-p-tolyl-nitroethyl-pyrrole [prepared according to a literature procedure (Kim, H.-J. and Lindsey, J. S. *J. Org. Chem.* 2005, 70, 5475-5486)] or a bioconjugatable group bearing a β-aryl nitroethyl pyrrole can be carried out. Briefly, the reactions closely mimic those reported in the original publication. The replacement of the geminal dimethyl groups with 2-methoxyethyl groups is not expected to cause problems. Both the methyl and the TBDPS ethers are sufficiently robust to the acid-catalyzed bacteriochlorin formation, and the swallowtail substituents are located at sites sufficiently removed from the reaction centers as to not introduce deleterious steric hindrance into the molecule.

A similar set of reactions is carried out for 32 (Scheme 17). Cleavage of the methyl groups can either be carried out at low temperatures with BBr$_3$ (Gleiter, R. and Müller, G. *J. Org. Chem.* 1988, 53, 3912-3917) to yield the tetraol derivative of 32, or in hot acetonitrile with TMS-I (Jung, M. E. and Lyster, M. A. *J. Org. Chem.* 1977, 42, 3761-3764) to furnish the tetraiodoalkyl bacteriochlorin 58. If TBDPS ethers are utilized, cleavage can be effected with a fluoride source, the most convenient being TBAF to reveal the unprotected hydroxy substituents in the swallowtail units. Compound 58 can undergo the Arbuzov reaction to furnish the tetrakis(dimethylphosphonate) 59, which can be hydrolyzed with TMS-I or TMS-Br to yield the water soluble bacteriochlorin-phosphonate 60. Reactions analogous to these have been carried out on porphyrins (Borbas, K. E. et al. *Bioconjugate Chem.* 2006, 17, 638-653) and are expected to be applicable without significant modifications for bacteriochlorins.

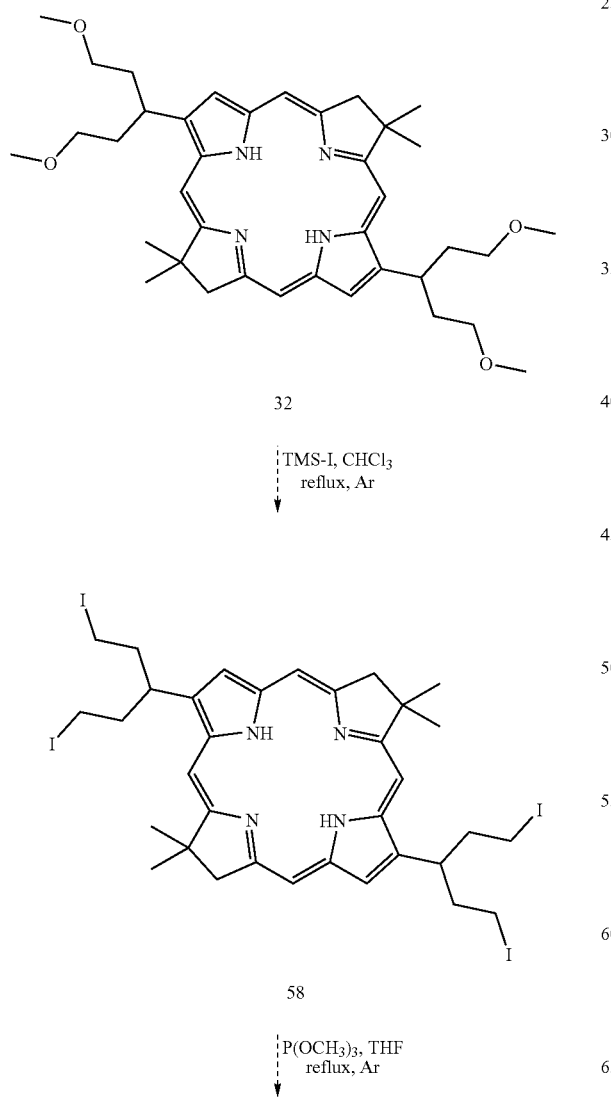

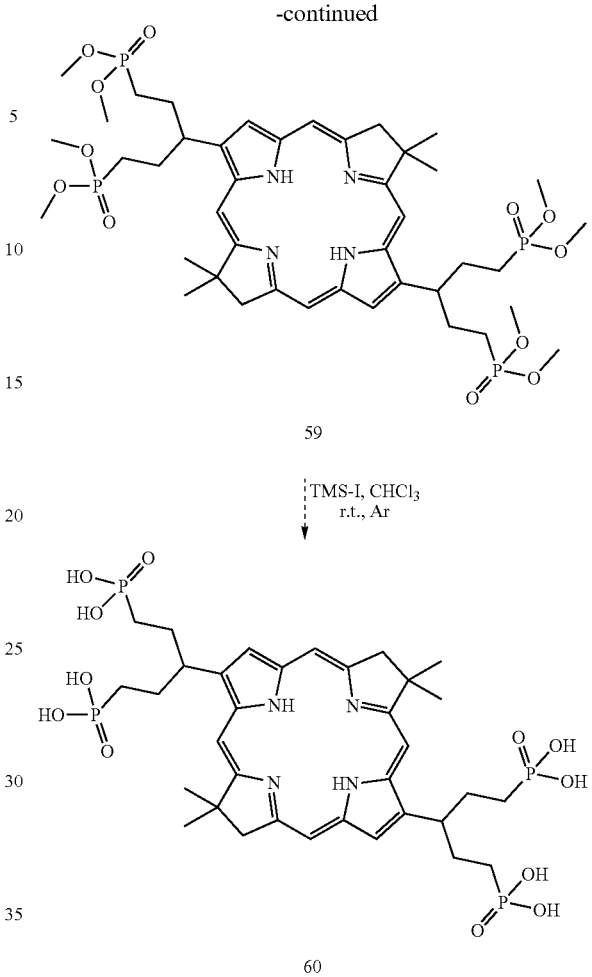

Experimental Section

General Procedures. $^1$H NMR (300 MHz) and $^{13}$C NMR (75 MHz) spectra were recorded in CDCl$_3$ unless noted otherwise. Absorption spectra and fluorescence spectra were collected at room temperature in CH$_2$Cl$_2$ unless noted otherwise. Infrared absorption spectra were recorded as thin films. Hydrophobic hydroporphyrins were analyzed in neat form by laser desorption mass spectrometry (LD-MS). The water-soluble hydroporphyrins were analyzed by direct infusion of water/methanol (30:70) solutions by atmospheric pressure electrospray mass spectrometry (ESI-MS). In both LD-MS and ESI-MS analyses, positive ions were detected unless noted otherwise. Solvents were dried according to standard procedures. All chemicals were used as received from commercial sources.

Chromatography. Preparative chromatography was performed using silica or alumina (80-200 mesh). Thin layer chromatography was performed on silica or alumina. Samples were visualized by UV-light (254 nm and 365 nm), Br$_2$-vapor or KMnO$_4$/K$_2$CO$_3$. Reversed phase preparative column chromatography was carried out using C-18-coated silica and eluants based on water admixed with methanol. Analytical RP-HPLC was carried out using an HPLC system [Hypersil C-18 column (5 μm, 125 mm×4 mm); A=water (0.1% TFA), B=acetonitrile (0.1% TFA); detection @ 254, 410 and 417 nm].

3-Cyano-1,5-dimethoxypentane (23CN). A solution of HMPA (12.0 mL) and LDA (16.4 mL of a 2.0 M solution in THF/hexanes/benzene) in dry THF (25 mL) at −78° C. under argon was treated with acetonitrile (1.75 mL, 33.5 mmol). The solution was stirred for 30 min, whereupon bromoethyl methyl ether (5.33 mL, 56.7 mmol) in THF (25 mL) was added dropwise. Stirring was continued for 2 h, after which a second portion of LDA (16.4 mL) was added. The solution was stirred for 30 min, whereupon bromoethyl methyl ether (5.33 mL, 56.7 mmol) in THF (25 mL) was added dropwise. The reaction was allowed to proceed for 2 h. Saturated aqueous $NH_4Cl$ was added, and the mixture was allowed to reach room temperature. Diethyl ether was added, the phases were separated, and the aqueous layer was extracted with diethyl ether. The organic extract was washed with water and brine, dried over $Na_2SO_4$, and concentrated. Column chromatography [silica, hexanes/diethyl ether (3:2)] afforded a colorless liquid (3.58 g, 81%): $^1$H NMR δ 1.83-1.96 (m, 4H), 2.97-3.02 (m, 1H), 3.35 (s, 6H), 3.43-3.58 (m, 4H).

3-Formyl-1,5-dimethoxypentane (23). A solution of 23CN (3.58 g, 22.8 mmol) in dry $CH_2Cl_2$ (181 mL) at −78° C. under argon was treated with DIBALH (27 mmol, 1.2 equiv, 27 mL of a 1.0 M solution in $CH_2Cl_2$), and the reaction was allowed to proceed for 1 h. Water (8 mL) was added, and the mixture was allowed to reach room temperature. Aqueous NaOH (8 mL, 2.5 M solution) was added, and stirring was continued for 15 min. Water (16 mL) was added, and the suspension was stirred for a further 15 min. The sample was dried ($Na_2SO_4$), concentrated at reduced pressure, and chromatographed [silica, hexanes/diethyl ether (3:2)], affording a colorless liquid (2.66 g, 73%): $^1$H NMR δ1.67-1.78 (m, 2H), 1.90-1.99 (m, 2H), 2.52-2.55 (m, 1H), 3.29-3.50 (m, 10H), 9.60 (d, J=2.1 Hz, 1H).

Ethyl 6-methoxy-4-(2-methoxyethyl)-hex-2-enoate (24). A solution of 23 (1.10 g, 6.88 mmol) and (carbethoxymethylene)triphenylphosphorane (2.63 g, 7.56 mmol, 1.1 equiv) was refluxed in $CH_2Cl_2$ (8.2 mL) for 24 h. The solvent was removed at reduced pressure. The oily residue was chromatographed [silica, hexanes/diethyl ether (1:1)] to yield a pale yellow oil (1.31 g, 88%): $^1$H NMR δ 1.50-1.62 (m, 2H), 1.69-1.85 (m, 2H), 2.45-2.51 (m, 1H), 3.23-3.33 (m, 10H), 5.79 (d, J=16.1 Hz, 1H), 6.71 (dd, J=9.5 Hz, $J_2$=16.1 Hz, 1H); $^{13}$C NMR δ 14.46, 34.42, 36.40, 58.79, 60.48, 70.42, 122.03, 152.01, 166.73; FAB-MS obsd 231.1596, calcd 231.1598 $[(M+H)^+, M=C_{12}H_{22}O_4]$.

3-(Ethoxycarbonyl)-4-(1,5-dimethoxypent-3-yl)pyrrole (25). A solution of 24 (3.00 g, 13.03 mmol) and TosMIC (2.54 g, 13.02 mmol) in DMSO/$Et_2O$ (1:2, 25 mL) was added via cannula to a vigorously stirred suspension of NaH (649 mg, 27.04 mmol) in $Et_2O$ (11.3 mL) under argon. Stirring was continued for 3 h. Brine and $CH_2Cl_2$ were added in small portions. The aqueous layer was extracted with $CH_2Cl_2$. The organic extract was washed with brine. The solvent was removed at reduced pressure. The oily residue was chromatographed [silica, $CH_2Cl_2$/ethyl acetate (9:1)] to yield a pale yellow oil (2.59 g, 74%): $^1$H NMR δ 1.32 (t, J=7.2 Hz, 3H), 1.88-1.95 (m, 4H), 3.26-3.33 (m, 10H), 4.24 (q, J=7.2 Hz, 2H), 6.54 (s, 1H), 7.37 (s, 1H), 8.74 (br, 1H); $^{13}$C NMR δ 14.59, 30.35, 36.04, 58.50, 59.47, 71.65, 114.69, 116.66, 124.92, 129.05, 165.28; FAB-MS obsd 270.1703, calcd 270.1705 $[(M+H)^+, M=C_{14}H_{23}NO_4]$.

3-(1,5-Dimethoxypent-3-yl)pyrrole (26). A solution of 25 (2.59 g, 9.63 mmol) in ethylene glycol (24 mL) was flushed with argon for 20 min. The mixture was immersed in an oil bath pre-heated to 160° C., and powdered NaOH (4.14 g, 103.5 mmol) was added. Stirring was continued for 1.5 h. The reaction mixture was allowed to cool to room temperature, whereupon water and $CH_2Cl_2$ were added. The aqueous layer was extracted with $CH_2Cl_2$. The combined organic layer was washed with water and brine. The organic layer was dried ($Na_2SO_4$). The solvent was removed at reduced pressure to yield a pale brown oil (1.01 g, 53%): $^1$H NMR δ 1.71-1.80 (m, 2H), 1.83-1.94 (m, 2H), 3.21-3.36 (m, 10H), 6.05-6.07 (m, 1H), 6.55-6.57 (m, 1H), 6.72-6.74 (m, 1H), 8.02 (br, 1H); $^{13}$C NMR δ 31.34, 36.98, 71.44, 107.06, 115.30, 117.99, 126.86; FAB-MS obsd 198.1488, calcd 198.1494 $[(M+H)^+, M=C_{11}H_{19}NO_2]$ Attempted Synthesis of 2-Formyl-3-(1,5-dimethoxypent-3-yl)pyrrole (27a). A solution of 26 (1.01 g, 5.13 mmol) in $CH_2Cl_2$ (51 mL) and DMF (1.64 mL) was cooled in an ice-water bath, and the solution was flushed with argon for 10 min. $POCl_3$ (583 μL, 6.40 mmol) was added. Stirring was continued for 1 h at 0° C. and 18 h at room temperature. The reaction mixture was cooled in an ice-water bath as aqueous NaOH (2.5 M) was added. The layers were separated. The aqueous layer was extracted with $CH_2Cl_2$. The organic extract was washed with water and brine. The organic layer was dried ($Na_2SO_4$). The solvent was removed at reduced pressure. The residue was chromatographed [silica, $CH_2Cl_2$/ethyl acetate (1:9)] to yield a pale yellow oil (609 mg). Upon $^1$H NMR analysis the sample was found to be a mixture of two isomers (27a/b). The mixture was carried on to the next step without further purification.

3-(1,5-Dimethoxypent-3-yl)-2-(2-nitroethyl)pyrrole (28). A mixture of crude 27a/b (1.41 g, 5.53 mmol) and nitromethane (3.67 mL) in THF (6.6 mL) was cooled in an ice-water bath and was treated with an ice-cold mixture of AcOH (414 μL) and propylamine (525 μL). Stirring was continued at 0° C. for 10 min and 2.5 h at room temperature. Water and $CH_2Cl_2$ were added to the reaction mixture. The aqueous layer was extracted with $CH_2Cl_2$. The combined organic layer was washed with water and brine. The organic layer was dried ($Na_2SO_4$). The solvent was removed at reduced pressure to yield a pale brown oil, which was dissolved in a mixture of $CHCl_3$ (15.4 mL) and 2-propanol (44 mL). This solution was treated with $SiO_2$ (10.22 g) and $NaBH_4$ (661 mg). After 1 h, TLC analysis of the reaction mixture showed the disappearance of the unsaturated intermediate. The reaction mixture was filtered, and the solid was washed with ethyl acetate. The filtrate was concentrated at reduced pressure, and the resulting oil was purified by column chromatography [silica, ethyl acetate/hexanes (1:3)] to yield a yellow oil (568 mg, 38%): $^1$H NMR δ 1.57-1.79 (m, 2H), 1.81-1.97 (m, 2H), 2.77-2.87 (m, 1H), 3.10-3.33 (m, 10H), 4.12 (q, J=6.9 Hz, 2H), 4.55 (q, J=6.9 Hz, 2H), 5.92-5.94 (m, 1H), 6.64-6.66 (m, 1H), 8.01 (br, 1H); $^{13}$C NMR δ 21.24, 29.03, 37.18, 60.61, 70.73, 106.11, 111.18, 117.70, 122.92.

1,1-Dimethoxy-4,4-dimethyl-6-[3-(1,5-dimethoxypent-3-yl)pyrrol-2-yl]-5-nitro-2-hexanone (30). A solution of 28 (568 mg, 2.10 mmol) and DBU (552 μL, 3.70 mmol) in anhydrous acetonitrile (5.9 mL) was treated with acetal 29 (500 mg, 3.16 mmol). The reaction mixture was stirred at room temperature for 7 h. The solvent was removed at reduced pressure. The dark brown residue was chromatographed [alumina, hexanes/ethyl acetate (1:3)] to yield a light brown oil (405.2 mg, 45%): $^1$H NMR δ 1.18 (s, 3H), 1.23 (s, 3H), 1.55-1.75 (m, 4H), 2.62-2.78 (m, 3H), 3.14-3.42 (m, 18H), 4.36 (s, 1H), 4.95 (dd, J=10.7 Hz, $J_2$=3.9 Hz, 1H), 5.90-5.92 (m, 1H), 6.58-6.60 (m, 1H), 7.80 (br, 1H).

1-(1,1-Dimethoxymethyl)-3,3-dimethyl-7-(1,5-dimethoxypent-3-yl)-2,3-dihydrodipyrrin (31). A stock solution of $TiCl_3$ was prepared from solid $TiCl_3$ (1 g), 38 wt % HCl (7.2 mL) and water (2 mL). A sample of this stock solution (7.06 mL) was diluted with water (37 mL), buffered to pH=6 with $NH_4$OAc (approximately 64.6 g), and flushed with Ar for at least 45 min. In a separate flask, a solution of 30 (405.2 g, 0.946 mmol) in THF (4.7 mL) was treated with NaOMe (264 mg, 4.89 mmol) under argon. After 1 h the second solution was cannulated into the first solution. The reaction mixture was stirred at room temperature for 6 h. Ethyl acetate was added, and the phases were separated. The aqueous layer was extracted with ethyl acetate. The organic extract was washed with water, dried ($Na_2SO_4$), and concentrated without heating. The residue was purified by column chromatography [alumina, ethyl acetate/hexanes (1:2)] to yield a pale yellow oil that was used immediately in the self-condensation reaction (96 mg, 26%): $^1$H NMR δ 1.21 (s, 6H), 1.68-1.97 (m, 4H), 2.61 (s, 2H), 2.93-3.50 (m, 17H), 5.01 (s, 1H), 5.92 (s, 1H), 5.97-5.99 (m, 2H), 6.80-6.82 (m, 1H), 10.54 (br, 1H).

2,12-Bis(1,5-dimethoxypent-3-yl)-8,8,18,18-tetramethylbacteriochlorin (32). A solution of 31 (96 mg, 0.127 mmol) in acetonitrile (14 mL) was divided into two equal batches. The solutions were separately treated with $BF_3$—$OEt_2$ (127 μL each). Stirring was continued for 18 h. The reactions were quenched with TEA (129 μL each). The two reaction batches were combined. The mixture was concentrated at reduced pressure. The residue was chromatographed to yield the title compound as a bright green solid (10.3 mg, 13%) and a trace of the 5-methoxybacteriochlorin analogue. Data for the title compound: $^1$H NMR δ −2.35 (s, 2H), 1.99 (s, 12H), 2.45-2.60 (m, 8H), 3.15 (s, 12H), 3.23-3.42 (m, 8H), 4.52-4.57 (m, 2H), 8.53 (m, 2H), 8.78-8.79 (m, 4H); LD-MS obsd 630.6, calcd 630.4145 ($C_{38}H_{54}N_4O_4$).

1,5-Dimethoxy-3-pentanone (35). A solution of 39 (2.22 g, 9.41 mmol) in acetonitrile (5 mL) was added to a homogeneous solution of NCS (4.94 g, 48.7 mmol, 5 equiv) and $AgNO_3$ (7.14 g, 42.2 mmol, 4.4 equiv) in acetonitrile/$H_2O$ (4:1, 90 mL). The reaction was allowed to proceed for 5-10 min, and was quenched by addition of saturated $Na_2SO_3$, followed by saturated $Na_2CO_3$ and brine at 1-min intervals (5 mL each). The mixture was filtered through a pad of celite. The solid was washed thoroughly with hexanes/$CH_2Cl_2$ (1:1). The layers were separated, and the aqueous layer was extracted with hexanes/$CH_2Cl_2$ (1:1). The organic extract was washed with water and brine. The organic layer was dried over $Na_2SO_4$. The mixture was filtered. The filtrate was concentrated at reduced pressure. The yellow oil thus obtained was 95% pure as determined by $^1$H NMR analysis. Further purification by chromatography (silica, diethyl ether) afforded a viscous, pale yellow liquid (1.36 g, 99%): $^1$H NMR δ 2.67 (t, J=6.3 Hz, 4H), 3.30 (s, 6H), 3.61 (t, J=6.3 Hz, 4H); $^{13}$C NMR δ 43.46, 58.84, 67.60, 207.36.

2-(2-Methoxyethyl)-1,3-dithiane (38). A solution of 1,3-dithiane (15.12 g, 126.0 mmol) in dry THF (150 mL) was treated at 0° C. with BuLi (53.0 mL of a 2.5 M solution, 132.5 mmol, 1.05 eqiuv) for 1.5 h. The reaction mixture was cooled to −78° C., and 2-bromoethyl methyl ether was added (11.3 mL, 16.7 g, 120.2 mmol). The reaction mixture was allowed to warm overnight to room temperature. The reaction was quenched by addition of saturated aqueous NH Cl. The mixture was extracted with $Et_2O$. The combined organic extracts were washed with water. The mixture was dried over $Na_2SO_4$. The mixture was filtered. The filtrate was concentrated at reduced pressure. The residue was chromatographed [silica, ethyl acetate/hexanes (1:19)] affording a viscous, colorless liquid (21.53 g, 96%): $^1$H NMR δ 1.84-1.93 (m, 1H), 1.96-2.03 (m, 2H), 2.07-2.15 (m, 1H), 2.78-2.93 (m, 4H), 3.34 (s, 3H), 3.51-3.55 (m, 4H), 4.19 (t, J=6.9 Hz, 1H); $^{13}$C NMR δ 26.16, 30.40, 35.58, 44.16, 58.84, 68.92; EI-MS: 178 (M$^+$), 146, 133, 119/121, 71/73, 45.

2,2-Bis(2-methoxyethyl)-1,3-dithiane (39). Following a standard procedure, a solution of 28 (3.45 g, 19.4 mmol) in dry THF (50 mL) was treated at 0° C. with BuLi (10.4 mL of a 2.5 M solution, 26.0 μmol, 1.3 eqiuv) for 1.5 h. The reaction mixture was cooled to −78° C., and 2-bromoethyl methyl ether (2.44 mL, 3.61 g, 25.95 mmol) was added. The reaction mixture was allowed to warm overnight to room temperature. The reaction was quenched by addition of saturated aqueous $NH_4Cl$. The mixture was extracted with $Et_2O$. The organic extract was washed with water. The mixture was dried over $Na_2SO_4$. The mixture was filtered. The filtrate was concentrated at reduced pressure. The residue was chromatographed [silica, ethyl acetate/hexanes (1:19)], then ethyl acetate/hexanes (1:9)] affording a viscous, pale yellow liquid (3.42 g, 76%): $^1$H NMR δ 1.93-1.96 (m, 2H), 2.20 (t, J=6.9 Hz, 4H), 2.83 (t, J=5.7 Hz, 4H), 3.30 (s, 6H), 3.57 (t, J=6.9 Hz, 4H); $^{13}$C NMR δ 25.28, 26.39, 38.85, 50.55, 58.75, 69.24; EI-MS 236 (M$^+$), 177, 161/162, 129/130, 97, 45.

1-Iodo-4-methoxy-2-(2-methoxyethyl)-but-1-ene (40). A solution of 35 (307 mg, 2.1 mmol) and iodoform (2.52 g, 6.4 mmol, 3 equiv) in dry, argon-flushed THF (20 mL) was cannulated to a slurry of $CrCl_2$ (2.10 g, 17.1 mmol, 8 equiv) in THF (20 mL). The reaction mixture was stirred at room temperature for 15 h. Water and ether were added. The layers were separated. The aqueous layer was extracted twice with ether. The organic extract was washed with water and brine. The organic layer was dried over $Na_2SO_4$. The mixture was filtered. The filtrate was concentrated at reduced pressure. Chromatography [silica, hexanes/diethyl ether, (1:1)] furnished an orange oil (560 mg, 98%): $^1$H NMR δ 2.47-2.55 (m, 4H), 3.32 (s, 3H), 3.34 (s, 3H), 3.44-3.49 (m, 4H), 6.06 (s, 1H).

2-Hydroxy-4-(2-methoxyethyl)-6-methoxybut-3-ene (41). A mixture of $CrCl_2$ (777 mg, 6.42 mmol) and $NiCl_2$ (3.97 mg, 0.0307 mmol) was added to a solution of 40 (560 mg, 2.07 mmol) and acetaldehyde (360 mg, 456 μL, mmol, 4 equiv) in anhydrous DMF (8.5 mL) under argon. The reaction was stirred at room temperature for 15 h. Water and ether were added. The layers were separated. The aqueous layer was extracted twice with ether. The organic extract was washed with water and brine. The organic layer was dried over $Na_2SO_4$. The mixture was filtered. The filtrate was concentrated at reduced pressure. The sample was employed in the subsequent oxidation procedure without further purification. $^1$H NMR δ 1.37-1.42 (m, 4H), 1.38 (d, J=5.1 Hz, 3H), 3.33 (s, 6H), 3.44-3.47 (m, 4H), 5.04 (q, J=5.1 Hz, 1H).

3-(tert-Butyldiphenylsilyloxy)propan-1-ol (44a). A solution of 1,3-propanediol (4.22 g, 55 mmol) in anhydrous $CH_2Cl_2$ (10 mL) under argon was treated with diisopropylethyl amine (10 mL) and tert-butyldiphenylsilyl chloride (5.00 mL, 5.29 g, 19.23 mmol). Stirring was continued for 2 h. The sample was concentrated, and the residue was purified by column chromatography (silica, hexanes/ethyl acetate (10:1)] affording a colorless oil (4.74 g, 78%): $^1$H NMR δ 1.07 (s, 9H), 1.78-1.86 (m, 2H), 2.46-2.50 (m, 1H), 3.83-3.88 (m, 4H), 7.37-7.48 (m, 6H), 7.68-7.75 (m, 4H); $^{13}$C NMR δ 19.33, 27.08, 34.52, 62.11, 63.46, 128.01, 130.03, 133.50, 135.80; FAB-MS obsd 315.1779, calcd 315.1780 [(M+H)$^+$, M=$C_{19}H_{26}O_2Si$].

3-(tert-Butyldiphenylsilyloxy)propan-1-al (45a). A solution of oxalyl chloride (1.0 mL, 11.0 mmol) in $CH_2Cl_2$ (25 mL) was cooled to 60° C. DMSO (1.7 mL, 22.0 mmol) was added, and the mixture was stirred for 2 min. A sample of 24a (3.14 g, 10.0 mmol) in $CH_2Cl_2$ was added to the first solution, and the reaction was allowed to proceed for 15 min. Triethylamine (7 mL) was added, and stirring was continued for 5 min at 60° C. The reaction mixture was allowed to warm to room temperature. Water and $Et_2O$ were added, and the phases were separated. The aqueous layer was extracted with $Et_2O$. The organic extract was washed with water and dried.

The sample was concentrated at reduced pressure, and the residue was purified by column chromatography [silica, hexanes/ethyl acetate (10:1)] to yield a colorless oil (2.55 g, 82%): $^1$H NMR δ 1.09 (s, 9H), 2.59-2.63 (m, 2H), 4.04 (t, J=6.0 Hz, 2H), 7.38-7.46 (m, 6H), 7.66-7.75 (m, 4H), 9.82-9.83 (m, 1H); $^{13}$C NMR δ 19.39, 27.88, 46.61, 58.53, 128.02, 130.07, 135.05, 135.79, 202.22.

2-(tert-Butyldiphenylsilyloxy)ethyl iodide (46a). A solution of 48 (1.82 g, 5.00 mmol) in acetone (50 mL) was treated with NaI (3.73 g, 25 mmol). Stirring was continued for 24 h. The sample was concentrated. The residue was taken up in a mixture of water and Et$_2$O. The phases were separated. The aqueous layer was extracted twice with Et$_2$O. The organic extract was washed with water and dried. The sample was concentrated. The oily residue was purified by column chromatography [silica, hexanes/ethyl acetate (10:1)] to yield a pale yellow oil (1.80 g, 88%): $^1$H NMR δ 1.10 (s, 9H), 3.24 (t, J=6.9 Hz), 3.89 (t, J=6.9 Hz), 7.39-7.49 (m, 6H), 7.69-7.73 (m, 6H); $^{13}$C NMR δ 7.05, 19.52, 27.05, 64.87, 128.03, 128.03, 130.10, 135.83.

3-(tert-Butyldiphenylsilyloxy)propyl iodide (46b). A solution of 44a (1.52 g, 4.84 mmol) in CH$_2$Cl$_2$ (16 mL) was treated consecutively with 12 (3.78 g, 14.52 mmol), PPh$_3$ (3.79 g, 14.52 mmol) and imidazole (1.01 g, 14.52 mmol). Stirring was continued for 24 h. The reaction was quenched by addition of aqueous sodium thiosulfate. The mixture was diluted with Et$_2$O. The phases were separated. The aqueous layer was extracted twice with Et$_2$O. The organic extract was washed with water and dried. The sample was concentrated. The oily residue was purified by column chromatography [silica, hexanes/ethyl acetate (10:1)] to yield a pale yellow oil (1.78 g, 87%): $^1$H NMR δ 2.03-2.07 (m, 2H), 3.36 (t, J=6.6 Hz, 2H), 3.73 (t, J=5.6 Hz, 2H), 7.38-7.45 (m, 6H), 7.67-7.70 (m, 4H); $^{13}$C NMR δ 3.72, 27.09, 36.37, 63.44, 127.95, 129.94, 133.81, 135.82.

2-(tert-Butyldiphenylsilyloxy)ethyl bromide (48). A mixture of tert-butyldiphenylsilyl chloride (20.32 g, 74.03 mmol) and imidazole (6.25 g, 91.9 mmol) was treated dropwise with 2-bromoethanol (47, 5 mL, 8.87 g, 70.8 mmol). Stirring was continued for 12 h. The mixture was diluted with Et$_2$O and water. The phases were separated, and the aqueous layer was extracted Et$_2$O. The organic extract was washed with water and dried over Na$_2$SO$_4$. Concentration of the sample yielded a pale brown oil (26.01 g, 97%): $^1$H NMR δ 1.11 (s, 9H), 3.45 (t, J=6.3 Hz, 2H), 3.96 (t, J=6.3 Hz, 2H), 7.42-7.47 (m, 6H), 7.70-7.73 (m, 4H); $^{13}$C NMR δ 19.52, 27.03, 33.43, 64.24, 128.04, 130.10, 133.49, 135.84.

4-Hydroxy-1,7-bis(tert-butyldiphenylsilyloxy)heptane (49). A solution of 46b (657 mg, 1.50 mmol) in anhydrous diethyl ether (2.7 mL) was cooled to −78° C. under argon for 10 min. This solution was treated with BuLi (2.06 mL, 3.00 mmol, 1.5 equiv), and the resulting mixture was stirred for 30 min. Meanwhile, a solution of 45b (243 mg, 0.745 mmol) in ether (1.3 mL) was cooled to −78° C. under argon. The lithiated-46b was added dropwise via cannula to the second solution, and the resulting mixture was stirred for a further 30 min. The reaction was quenched by addition of aqueous NH$_4$Cl. Water and ether were added, and the phases were separated. The aqueous layer was extracted with twice ether. The organic extract was washed with water and dried (Na$_2$SO$_4$). The solution was concentrated, and the oily residue was purified by column chromatography [silica, hexanes/ethyl acetate (10:1)] to yield a colorless film (233 mg, 49%): $^1$H NMR δ 1.51-1.66 (m, 8H), 2.05 (br, 1H), 3.65-3.72 (m, 5H), 7.39-7.41 (m, 12H), 7.67-7.74 (m, 8H).

1,7-Bis(tert-butyldiphenylsilyloxy)heptan-4-one (50). A solution of 49 (233 mg, 0.374 mmol) in CH$_2$Cl$_2$ (1 mL) was treated with PCC (121 mg, 0.561 mmol) at room temperature. Stirring was continued for 2 h. The mixture was diluted with Et$_2$O, and the mixture was applied onto a plug of silica. The solid was washed with Et$_2$O. The sample was concentrated, and the oily residue was chromatographed [silica, hexanes/ethyl acetate (10:1) to yield a colorless oil (166 mg, 71%): $^1$H NMR δ 1.82-1.88 (m, 4H), 2.55-2.58 (m, 4H), 3.65-3.72 (m, 4H), 7.43-7.45 (m, 12), 7.69-7.71 (m, 8H).

7-(tert-Butyldiphenylsilyloxy)$_4$-[3-(tert-butyldiphenylsilyloxy)propyl]-4-hydroxyheptan-2-one (51). A solution of 50 (160 mg, 0.257 mmol) in anhydrous CH$_2$Cl$_2$ (0.3 mL) was cooled in an ice bath under argon for 10 min. TiCl$_4$ (25 μL) was added, and the resulting mixture was stirred for 10 min. 2-(Trimethylsilyloxy)prop-1-ene (33.4 mg, 0.257 mmol, 0.43 μL) was added. Stirring was continued for 20 min. The reaction mixture was diluted with ice-cold water. CH$_2$Cl$_2$ was added, and the phases were separated. The aqueous layer was extracted with CH$_2$Cl$_2$. The combined organic layers were dried (Na$_2$SO$_4$). Concentration of the sample under reduced pressure yielded a pale yellow oil, which was purified by column chromatography [silica, hexanes/ethyl acetate (10:1→3:1)] affording a colorless oil (18 mg, 10%): $^1$H NMR δ 1.04 (s, 18H), 1.85-1.89 (m, 4H), 2.18 (s, 3H), 2.61 (s, 2H), 3.65 (m, 4H), 7.37-6.42 (m, 12H), 7.65-7.67 (m, 8H).

Ethyl-3-(4-nitrophenyl)prop-2-enoate (54). A solution of 4-nitrobenzaldehyde (53, 10.00 g, 66.23 mmol) and (carbethoxymethylene)triphenylphosphorane (27.92 g, 72.85 mmol, 1.1 equiv) was refluxed in CH$_2$Cl$_2$ (74 mL) for 24 h. The solvent was removed at reduced pressure. The oily residue was chromatographed (silica, hexanes/diethyl ether, 1:1) to give a pale yellow solid, which was shown by $^1$H NMR and TLC analysis to contain triphenylphosphine oxide. This sample was further purified by short-path Kugelrohr distillation (0.05 mmHg, up to 180° C.) to yield a pale yellow solid (3.74 g, 26%, mixture of E and Z isomers): $^1$H NMR δ 1.33 (t, J=7.5 Hz, 3H), 4.27 (q, J=7.5 Hz, 2H), 6.54 (d, J=15.6 Hz, 1H), 7.62-7.71 (m, 3H), 8.17-8.24 (m, 2H); $^{13}$C NMR δ 14.48, 61.22, 122.81, 123.54, 124.38, 130.43, 132.24, 140.76, 141.82, 166.24.

3-(Ethoxycarbonyl)-4-(4-nitrophenyl)pyrrole (55). A solution of 54 (3.74 g, 16.91 mmol) and TosMIC (3.30 g, 16.92 mmol) in DMSO/Et$_2$O (1:2, 33 mL) was added via cannula to a vigorously stirred suspension of NaH (842 mg, 35.1 mmol) in Et$_2$O (15 mL) under argon. Stirring was continued for 3 h. Brine and CH$_2$Cl$_2$ were added in small portions. The aqueous layer was extracted with CH$_2$Cl$_2$. The organic extract was washed with brine. The solvent was removed at reduced pressure, and the oily residue was chromatographed [silica, CH$_2$Cl$_2$/ethyl acetate (9:1)] to yield a brown solid (3.23 g, 84%): $^1$H NMR δ 1.23-1.29 (m, 3H), 4.20-4.27 (m, 2H), 6.88-6.90 (m, 1H), 7.53-7.55 (m, 1H), 7.64-7.67 (m, 2H), 8.18-8.21 (m, 2H), 8.78 (br, 1H).

3-(4-Nitrophenyl)pyrrole (56). A solution of 55 (2.44 g, 9.92 mmol) in ethylene glycol (25 mL) was flushed with argon for 20 min. The mixture was immersed in an oil bath pre-heated to 160° C., and powdered NaOH (4.22 g, 105 mmol) was added. Stirring was continued for 1.5 h. The reaction mixture was allowed to cool to room temperature, and water and CH$_2$Cl$_2$ were added. The aqueous layer was extracted with CH$_2$Cl$_2$. The organic extract was washed with water and brine. The organic layer was dried (Na$_2$SO$_4$). The solvent was removed at reduced pressure to yield a pale brown oil (502 mg, 25%): $^1$H NMR δ 6.36-6.48 (m, 1H), 6.69-6.73 (m, 2H), 6.79-6.81 (m, 1H), 6.96-6.98 (m, 1H), 7.33-7.38 (m, 1H), 8.21 (br, 1H).

The foregoing is illustrative of the present invention, and is not to be construed as limiting thereof. The invention is defined by the following claims, with equivalents of the claims to be included therein.

That which is claimed is:

1. A compound of Formula DII:

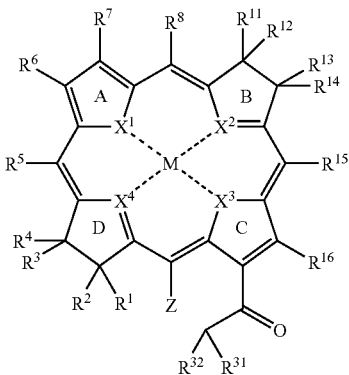

(DII)

wherein:
M is a metal or is absent;
$X^1, X^2, X^3$ and $X^4$ are each independently selected from the group consisting of Se, NH, $CH_2$, O and S;
Z is halo;
$R^1, R^2, R^3, R^4, R^5, R^6, R^7, R^8, R^{11}, R^{12}, R^{13}, R^{14}, R^{15}, R^{16}, R^{21}, R^{22}, R^{31}$ and $R^{32}$ are each independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, acyl, formyl, carboxylic acid, acylamino, ester, amide, hydroxyl, nitro, alkylthio, amino, alkylamino, arylalkylamino, disubstituted amino, acyloxy, sulfoxyl, sulfonyl, sulfonate, sulfonic acid, sulfonamide, urea, alkoxylacylamino, aminoacyloxy, protein, peptide, antibody, nucleic acid, and polyalkylene oxide;
wherein each pair of $R^1$ and $R^2$, $R^3$ and $R^4$, $R^{11}$ and $R^{12}$, $R^{13}$ and $R^{14}$, $R^{21}$ and $R^{22}$, or $R^{31}$ and $R^{32}$, can together form =O;
wherein $R^2$ and $R^3$ can together form a double bond; and $R^{12}$ and $R^{13}$ can together form a double bond;
and wherein each of $R^1$ and $R^2$, $R^3$ and $R^4$, $R^{11}$ and $R^{12}$, or $R^{13}$ and $R^{14}$, can together form spiroalkyl.

2. The compound of claim 1, wherein $R^{31}$ and $R^{32}$ are each independently H, alkyl, or aryl;
or one of $R^{31}$ and $R^{32}$ is H and the other is cyano;
or one of $R^{31}$ and $R^{32}$ is H and the other is ester.

3. The compound of claim 1, wherein $R^{31}$ and $R^{32}$ are each independently H or alkyl.

4. A compound of Formula DII:

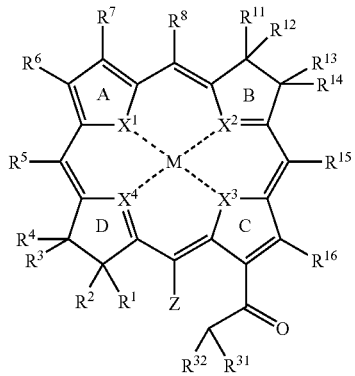

(DII)

wherein:
M is a metal or is absent;
$X^1, X^2, X^3$ and $X^4$ are each independently selected from the group consisting of Se, NH, $CH_2$, O and S;
Z is halo;
$R^1, R^2, R^3, R^4, R^5, R^6, R^7, R^8, R^{11}, R^{12}, R^{13}, R^{14}, R^{15}, R^{16}, R^{21}, R^{22}, R^{31}$ and $R^{32}$ are each independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, acyl, formyl, carboxylic acid, acylamino, ester, amide, hydroxyl, nitro, alkylthio, amino, alkylamino, arylalkylamino, disubstituted amino, acyloxy, sulfoxyl, sulfonyl, sulfonate, sulfonic acid, sulfonamide, urea, alkoxylacylamino, aminoacyloxy, groups, bioconjugatable groups, targeting groups, and water soluble groups protein, peptide, antibody, nucleic acid, and polyalkylene oxide;
wherein each pair of $R^1$ and $R^2$, $R^3$ and $R^4$, $R^{11}$ and $R^{12}$, $R^{13}$ and $R^{14}$, $R^{21}$ and $R^{22}$, or $R^{31}$ and $R^{32}$, can together form =O;
wherein $R^2$ and $R^3$ can together form a double bond; and $R^{12}$ and $R^{13}$ can together form a double bond;
and wherein each of $R^1$ and $R^2$, $R^3$ and $R^4$, $R^{11}$ and $R^{12}$, or $R^{13}$ and $R^{14}$, can together form spiroalkyl;
and subject to the proviso that: (i) at least one of $R^1, R^2, R^3, R^4, R^5, R^6, R^7, R^8, R^{11}, R^{12}, R^{13}, R^{14}, R^{15}, R^{16}, R^{21}, R^{22}, R^{31}$ and $R^{32}$ is a group of the Formula:

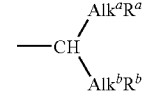

wherein $R^a$ and $R^b$ are each an independently selected ionic group, polar group, bioconjugatable group, or targeting group, and $Alk^a$ and $Alk^b$ are each an independently selected C1-C50 alkylidene chain; or (ii) at least one pair of $R^{11}$ and $R^{12}$, $R^{13}$ and $R^{14}$, $R^{21}$ and $R^{22}$, and $R^{23}$ and $R^{24}$ are both independently selected Alk'R', wherein Alk' is a C1-C50 alkylidene chain, and R is protein, peptide, antibody, nucleic acid, or polyalkylene oxide.

5. The compound of claim 1, wherein each said cycloalkyl, aryl, heterocyclo, aryl, and heteroaryl, independently or as a part of another group, is independently selected from the group consisting of:
azulenyl, indanyl, indenyl, naphthyl, phenyl, tetrahydronaphthyl, cyclopropyl, cyclobutyl, cyclopentyl, cyclohexyl, cycloheptyl, cyclooctyl, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, purine, pyranopyridine, quinoline, quinolizine, quinoxaline, quinazoline, tetrahydroisoquinoline, tetrahydroquinoline, and thiopyranopyridine.

6. The compound of claim 4, wherein each said cycloalkyl, aryl, heterocyclo, aryl, and heteroaryl, independently or as a part of another group, is independently selected from the group consisting of:

azulenyl, indanyl, indenyl, naphthyl, phenyl, tetrahydronaphthyl, cyclopropyl, cyclobutyl, cyclopentyl, cyclohexyl, cycloheptyl, cyclooctyl, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, purine, pyranopyridine, quinoline, quinolizine, quinoxaline, quinazoline, tetrahydroisoquinoline, tetrahydroquinoline, and thiopyranopyridine.

* * * * *

UNITED STATES PATENT AND TRADEMARK OFFICE
CERTIFICATE OF CORRECTION

Page 1 of 4

PATENT NO.     : 8,207,329 B2
APPLICATION NO. : 12/095435
DATED          : June 26, 2012
INVENTOR(S)    : Lindsey et al.

It is certified that error appears in the above-identified patent and that said Letters Patent is hereby corrected as shown below:

In The Specifications:
Column 13, Line 57: Please add a -- . -- after "chelates)" so it reads -- chelates). --
and
start a new paragraph at ""Ionic group" as used herein"

Column 58, Line 32: Please correct "with the 1-electrons"
to read -- with the π-electrons --

Column 62, Lines 35-36: Please correct "(logs ϵ=4.67)" to read -- (log ε=4.67) --
Line 52: Please correct "(log s=4.75)" to read -- (log ε=4.75) --

Column 63, Line 35: Please correct "nm n." to read -- nm. --

Column 65, Chart 4, 1st Figure, Lines 19-30: Please correct

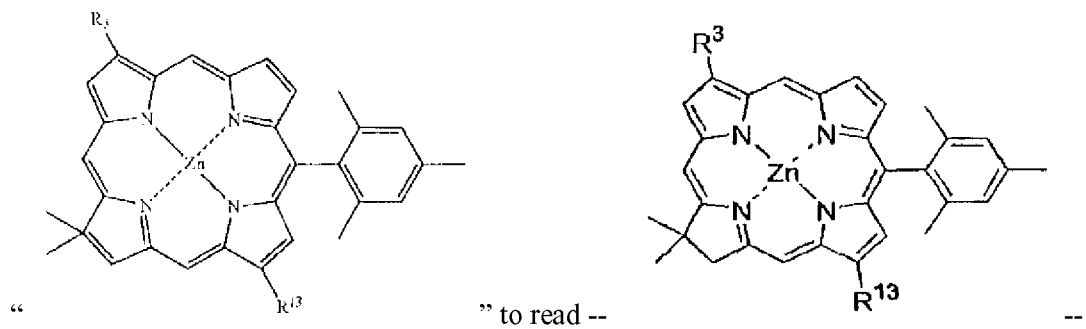

Signed and Sealed this
Twenty-first Day of May, 2013

Teresa Stanek Rea
*Acting Director of the United States Patent and Trademark Office*

Column 65, Chart 4, 2nd Figure, Lines 46-57: Please correct

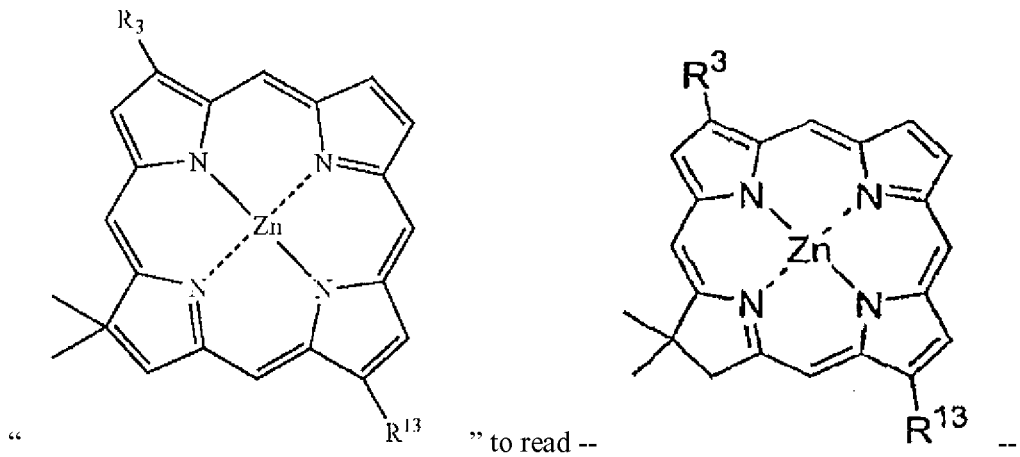

" to read --

Column 69, Line 47: Please correct "19 (30%)." to read -- 19 (~30%). --

Column 74, Scheme 7: Please correct

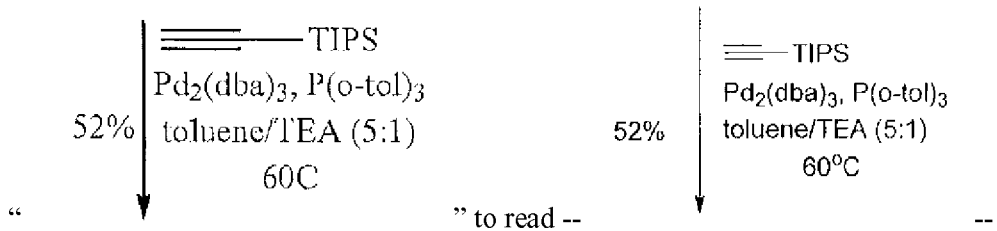

" to read --

Column 74, Scheme 8: Please correct

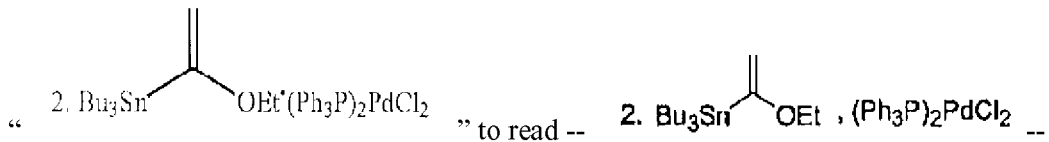

" to read --

Column 75, Scheme 9: Please correct

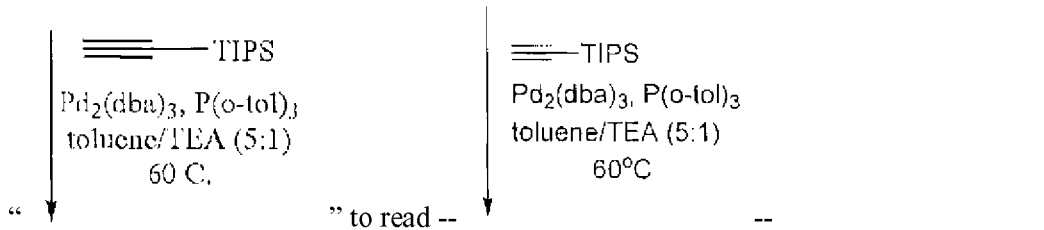

" to read --

Column 76, Scheme 8 continued, Line 15: Please correct "ZnC–M$^{10}$Br$^{13}$"
to read -- ZnC–M$^{10}$A$^{13}$ --

Column 77, Scheme 10, Line 18: Please correct: "ZnC–Br$^3$Br$^{13}$ R$^{10}$ = H"
to read -- ZnC–E$^3$Br$^{13}$ R$^{10}$ = H --

CERTIFICATE OF CORRECTION (continued)
U.S. Pat. No. 8,207,329 B2

Column 77, Scheme 10, Lines 22-30: Please correct:

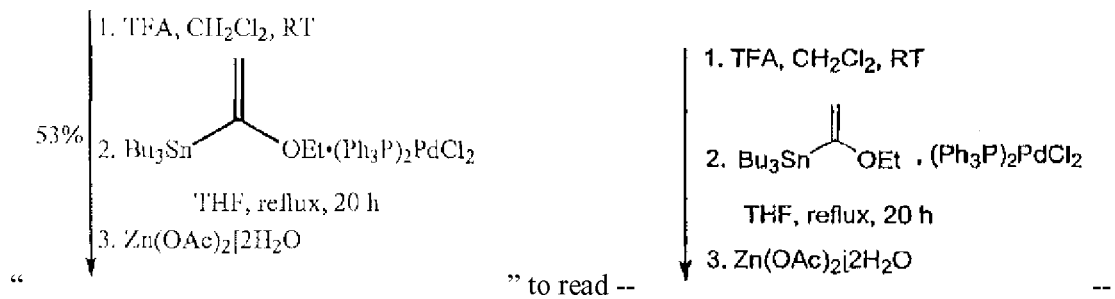

Column 83, Line 49: Please correct "(cl$_9$H$_{23}$BrN$_2$O$_5$)."
to read -- (C$_{19}$H$_{23}$BrN$_2$O$_5$S). --

Column 86, Line 52: Please correct "(C$_{42}$H$_{47}$BrN$_4$SiZn); tabs 418, 634 nm."
to read -- (C$_{42}$H$_{47}$BrN$_4$SiZn); λabs 418, 634 nm. --

Column 87, Line 19: Please correct "(C$_{42}$H$_{49}$N$_4$SiZn);" to read -- (C$_{42}$H$_{48}$N$_4$SiZn); --
Line 38: Please correct "Zn(OAc)$_{2\text{-}2}$H$_2$O" to read -- Zn(OAc)$_2$·2H$_2$O --
Line 65: Please correct "(C$_{42}$H$_{48}$N4SiZn);" to read -- (C$_{42}$H$_{48}$N$_4$SiZn); --

Column 88, Lines 52-53: Please correct "Zn(OAc)$_{2\text{-}2}$H$_2$O (40 mg, 0.18 mmol)"
to read -- Zn(OAc)$_2$·2H$_2$O (40mg, 0.18 mmol) --

Column 89, Line 12: Please correct "Zn(OAc)$_{2\text{-}2}$H$_2$O" to read -- Zn(OAc)$_2$·2H$_2$O --
Line 37: Please correct "(1) at the α-pyrrolic positions"
to read -- (1) at the β-pyrrolic positions --
Line 60: Please correct "swallowtail substituent at the 5-posi-"
to read -- swallowtail substituent at the β-posi- --

Column 92, Scheme 11, boxed figures: Please correct

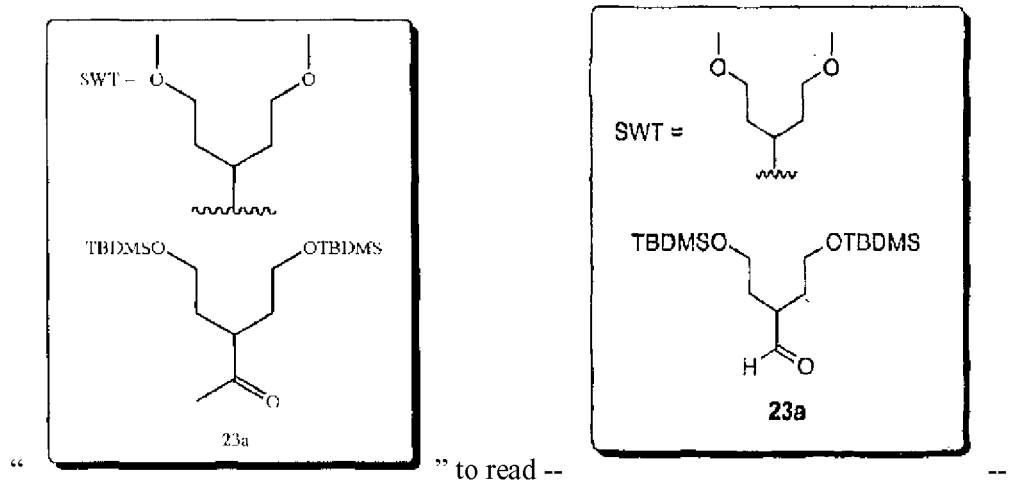

Column 93, Line 1: Please insert -- <u>Scheme 12</u> -- immediately before first compound Column 98, Line 46: Please correct "BF$_3$–OEt$_2$ or Ti(O$^1$Pr)$_4$,"
to read -- BF$_3$·OEt$_2$ or Ti(O$^i$Pr)$_4$ --
Line 56: Please correct "the Meow Cl" to read -- the MeO→ Cl --

Column 104, Scheme 17, Lines 19-21: Please correct

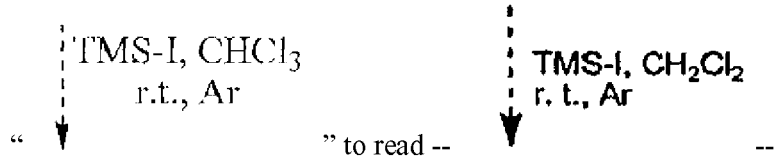

Column 107, Line 17: Please correct "with BF$_3$–OEt$_2$" to read -- with BF$_3$·OEt$_2$ --

Column 108, Line 1: Please correct "26.0 µmol," to read -- 26.0 mmol, --
Line 59: Please correct "cooled to 60°C." to read -- cooled to –60°C. --
Line 64: Please correct "min at 60°C." to read min at -- –60°C. --

Column 109, Line 23: Please correct "with 12 (3.78 g," to read -- with I$_2$ (3.78 g, --

In the Claims:
Column 112, Claim 4, Lines 35-36: Please delete "groups, bioconjugatable groups, targeting groups, and water soluble groups"